(12) United States Patent
Lundtveit et al.

(10) Patent No.: US 8,298,170 B2
(45) Date of Patent: Oct. 30, 2012

(54) METHOD OF MAKING A PERITONEAL DIALYSIS THERAPY MACHINE

(75) Inventors: Loren M. Lundtveit, Wadsworth, IL (US); Jose Alvaro, Vernon Hills, IL (US); Joseph H. Bowman, Jr., Lake Villa, IL (US); Dan O'Sullivan, Billerica, MA (US); Stan Thompson, New Boston, NH (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1435 days.

(21) Appl. No.: 11/617,536

(22) Filed: Dec. 28, 2006

(65) Prior Publication Data

US 2007/0213654 A1    Sep. 13, 2007

Related U.S. Application Data

(63) Continuation of application No. 10/155,384, filed on May 24, 2002, now Pat. No. 7,175,606.

(51) Int. Cl.
*A61M 1/00* (2006.01)

(52) U.S. Cl. .......... 604/29

(58) Field of Classification Search ........ 604/28, 604/29, 199, 533–538
See application file for complete search history.

(56) References Cited

U.S. PATENT DOCUMENTS

| | | |
|---|---|---|
| 3,809,241 A | 5/1974 | Alvine |
| 4,150,673 A | 4/1979 | Watt |
| 4,212,738 A | 7/1980 | Henne |
| 4,269,708 A | 5/1981 | Bonomini et al. |
| 4,381,003 A | 4/1983 | Buoncristiani |
| 4,396,382 A | 8/1983 | Goldhaber |
| 4,479,760 A | 10/1984 | Bilstad et al. |
| 4,479,761 A | 10/1984 | Bilstad et al. |
| 4,498,900 A | 2/1985 | Buoncristiani |
| 4,559,036 A | 12/1985 | Wunsch |
| 4,560,472 A | 12/1985 | Granzow et al. |
| 4,678,460 A | 7/1987 | Rosner |
| 4,844,074 A | 7/1989 | Kurucz |
| 5,053,003 A | 10/1991 | Dadson et al. |

(Continued)

FOREIGN PATENT DOCUMENTS

DE        1964735       7/1971

(Continued)

OTHER PUBLICATIONS

Defendants' Preliminary Invalidity Contentions for U.S. Patent No. 5,421,823, *Baxter Healthcare Corporation v. Fresenius Medical Care Holdings*, Case No. C 07-01359 PJH (JL), filed Aug. 24, 2007.

(Continued)

*Primary Examiner* — Nicholas Lucchesi
*Assistant Examiner* — Pritesh Patel
(74) *Attorney, Agent, or Firm* — K&L Gates LLP

(57) ABSTRACT

A method for making a peritoneal dialysis therapy machine having a tubing set includes: packaging an end of each of a plurality of the tubes of the set in a body; arranging the tubes according to a sequence of steps of a dialysis treatment set-up so that a user is urged to remove the tubes from the single body in a desired order; and configuring the body to plug connectors attached to each of the ends of the tubes.

20 Claims, 37 Drawing Sheets

U.S. PATENT DOCUMENTS

| | | | |
|---|---|---|---|
| 5,108,367 | A | 4/1992 | Epstein et al. |
| 5,141,492 | A | 8/1992 | Dadson et al. |
| 5,163,900 | A | 11/1992 | Wortrich |
| 5,324,422 | A * | 6/1994 | Colleran et al. ............... 210/85 |
| 5,334,139 | A | 8/1994 | Jeppsson et al. |
| 5,338,293 | A | 8/1994 | Jeppsson et al. |
| 5,350,357 | A | 9/1994 | Kamen et al. |
| 5,364,342 | A | 11/1994 | Beuchat et al. |
| 5,421,823 | A | 6/1995 | Kamen et al. |
| 5,429,485 | A | 7/1995 | Dodge |
| 5,474,683 | A | 12/1995 | Bryant et al. |
| 5,538,405 | A | 7/1996 | Patno et al. |
| 5,628,908 | A | 5/1997 | Kamen et al. |
| 5,634,896 | A | 6/1997 | Bryant et al. |
| 5,722,947 | A | 3/1998 | Jeppsson et al. |
| 5,836,908 | A | 11/1998 | Beden et al. |
| 5,938,634 | A | 8/1999 | Packard |
| 5,989,423 | A | 11/1999 | Kamen et al. |
| 6,293,921 | B1 | 9/2001 | Shinmoto et al. |
| 6,764,761 | B2 | 7/2004 | Eu et al. |
| 6,814,547 | B2 | 11/2004 | Childers et al. |
| 6,869,538 | B2 | 3/2005 | Yu et al. |
| 6,929,751 | B2 | 8/2005 | Bowman, Jr. et al. |
| 6,939,111 | B2 | 9/2005 | Huitt et al. |
| 7,033,539 | B2 | 4/2006 | Krensky et al. |
| 7,087,036 | B2 | 8/2006 | Busby et al. |
| 7,153,286 | B2 | 12/2006 | Busby et al. |
| 7,175,606 | B2 | 2/2007 | Bowman, Jr. et al. |

FOREIGN PATENT DOCUMENTS

| | | |
|---|---|---|
| DE | 19814695 A1 | 10/1999 |
| EP | 0028371 | 5/1981 |
| EP | 0204260 | 12/1986 |
| EP | 0319272 | 6/1989 |
| EP | 0402505 | 12/1990 |
| EP | 0011935 | 5/1991 |
| EP | 0248632 | 4/1992 |
| FR | 2371931 | 6/1978 |
| FR | 2440740 | 6/1980 |
| GB | 1326236 | 8/1973 |
| SE | 331736 | 1/1971 |
| WO | WO 84/02473 | 7/1984 |
| WO | WO 85/04813 | 11/1985 |
| WO | WO 86/01115 | 2/1986 |
| WO | WO 91/02484 | 3/1991 |
| WO | WO 92/15349 | 9/1992 |
| WO | WO 93/01845 | 2/1993 |
| WO | WO 95/35124 | 12/1995 |
| WO | WO 99/06082 | 2/1999 |
| WO | WO 01/91829 | 12/2001 |

OTHER PUBLICATIONS

Defendants' Supplemental Invalidity Contentions for U.S. Patent No. 5,421,823, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,503,062, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,808,369, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,324,422, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,438,510, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,814,547, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 5,431,626, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 6,929,751, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Patent No. 7,083,719, *Baxter Healthcare Corporation v. Fresenius Medical Care Holdings*, Case No. C 07-01359 PJH (JL), filed Jan. 31, 2008.
Defendants' Final Invalidity Contentions for U.S. Patent No. 6,814,547, *Baxter Healthcare Corporation v. Fresenius Medical Care Holdings*, Case No. C 07-01359 PJH (JL), filed Apr. 1, 2009.
Fresenius 90/2 Peritoneal Therapy Cycler (on information and belief, on sale in United States by 1991).
Blumenkrantz et al., Applications of the Redy Sorbent System to Hemodialysis and Peritoneal Dialysis, Artificial Organs, vol. 3, No. 3 (Aug. 1979).
Blumenkrantz et al., Development of a Sorbent Peritoneal Dialysate Regeneration System—A Progress Report, European Dialysis and Transplant Association 1978.
Blumenkrantz and Roberts, Progress in Peritoneal Dialysis: a Historical Prospective, Contributions to Nephrology, vol. 17, pp. 101-110 (1979).
Diaz-Buxo, CCPD is even better than CAPD, Kidney International, vol. 28, Suppl. 17, pp. S-26-S-28 (1985).
Diaz-Buxo, CCPD Technique and Current Clinical Experience (1982).
Diaz-Buxo, et al., Continuous Cyclic Peritoneal Dialysis: A Preliminary Report, Artificial Organs, vol. 5, No. 2, pp. 157-161 (May 1981).
Diaz-Buxo, Current Status of Continuous Cyclic Peritoneal Dialysis (CCPD), Peritoneal Dialysis International, vol. 9, pp. 9-14 (1989).
Diaz-Buxo, Issues in Nephrology: Continuous Cyclic Peritoneal Dialysis, NAPHT News, Feb. 1983, pp. 12-14.
Diaz-Buxo, Peritoneal Dialysis Reverse Osmosis Machines and Cyclers, Dialysis Therapy, pp. 41-48 (1986).
Drukker et al., Replacement of Renal Function by Dialysis, 2nd Ed., Ch. 21, 1983.
Lewin and Maxwell, Sorbent-Based Regenerating Peritoneal Dialysis, Sorbents and Their Clinical Applications, pp. 353-374 (1980).
Lewin et al., Sorbent for Application in the Treatment of ESRD Patients, Annual Progress Report re Contract #N01-AM-9-2215, submitted Jun. 22, 1982.
Ratnu, et al., A New Technique—Semicontinuous Rapid Flow, High Volume Exchange—For Effective Peritoneal Dialysis in Shorter Periods, Nephron, vol. 31, pp. 159-163 (1982).
Twardowski, Peritoneal Dialysis: Current Technology and techniques, Postgraduate Medicine, vol. 85, No. 5 (Apr. 1989).
Product Evaluation Reports: Peritoneal Dialysis Machine "Pac-X," Hospital Materials Management, vol. 12, No. 11, p. 16 (Nov. 1987).
Brochure entitled, AP Hauni: Automatisches Peritonealdialyse-Great (1970).
Brochure entitled, Fresenius Delivers 90/2 Peritoneal Therapy Cycler.
Brochure entitled, REDY Universal Re-circulating Dialysate System.
Brochure entitled, SIF 901 Perugia.
Translation of brochure entitled, SIF 901 Perugia.
Translation of Certificate for translation of brochure entitled, SIF 901 Perugia.
Operators Instructions for Fresenius 90/2 Peritoneal Therapy Cycler.
Photo of dialysis patient connected to machine.
Photo of dialysis machine.
Peritoneal Dialyser PD700 Service Manual, Jun. 1977.
Peritoneal Dialyser PD700 Instruction Manual.
PD700 Peritoneal Dialyser Users Hand-book, Dec. 1977.
Operating Instructions, Peritoneal Dialyser PD700, for Ser. No. 300.
Brochure entitled, Peritoneal Dialyser PD700, May 1979.
Brochure entitled, For Volume Measurement, Temperature Control and Cycling of Dialysing Fluid, Peritoneal Dialyser PD700, 1970.
Skotselanvisning for Peritoneal—Dialysapparat PD700.
Bergstrom et al., An Automated Apparatus for Peritoneal Dialysis with Volumetric Fluid Balance Measurement, reprinted from Dialysis & Transplantation, Jun./Jul. 1976.
U. Callsen, Peritoneal-Dialysator PD700, Prakt. Anasth. 9 (1974).
Piazolo et al., Erfahrungen mit einem neuen vollautomatsischen Paritoneal-dialysegerat, Munchener Medizinische Wochenschrift, 1972.
Technical Note, PD700 Peritoneal Dialyser, Jan. 29, 1979.
Assorted Photos of dialysis machine with and without casing on.

Elsevier Science Ltd., Air-Operated Diaphragm Pumps, World Pumps, Jan. 1996, at 38.
Bran & Luebbe GmbH, Diaphragm Metering Pumps, Chem. Eng'g Progress, Apr. 1987, at 18-24.
M. Schalbach, E.S. Bucherl & O. Franke, An Electronically Controlled Implantable Auxiliary Ventricle, published in Advances in Biomedical Engineering and Medical Physics: Cardiac Engineering, vol. 3.
Gene L. Mrava, Mock Circulation Systems for Artificial Hearts, published in Advances in Biomedical Engineering and Medical Physics: Cardiac Engineering, vol. 3.
W.M. Phillips, J.A. Brighton & W.S. Pierce, Artificial Heart Evaluation Using Flow Visualization Techniques, published in Transactions: American Society for Artificial Internal Organs, vol. XVIII (1972).
J.A. Brighton, W.S. Pierce, D.Landis & G. Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).
Operator's Instructions, Fresenius 90/2 Peritoneal Therapy Cycler (Rev. C. copyright 1991-2000).
Memorandum of Donald X. Vaccarino entitled 90/2 History File (1991-1992).
Document entitled 90/2 Cycler Software, Version 3.96 (Jan. 24, 1992).
Software Change Requests (Jul. 8, 1991-Oct. 3, 1992).
Brochure entitled Fresenius Delivers 90/2 Peritoneal Therapy Cycler (Apr. 2001).
90/2 Quick Reference.
90/2 Cycler Parts List (Nov. 6, 1997).
90/2 Cycler Box Contents.
90/2 Brochure (Jul. 1993).
90/2 Brochure (Apr. 2001).
90/2 Directions for Use.
90/2 Document Index.
Freedom Cycler Document Index.
Specification entitled Inpersol Cycler 3000 Operating Manual, List No. 21952-04, dated 1990.
Training aid entitled Learning to Use the Inpersol Cycler 3000, dated Jul. 1991.
Fresenius USA/Delmed 90/2 Peritoneal Dialysis System Operators Manual, dated Feb. 6, 1991.
Fresenius 90/2 Peritoneal Therapy Cycler Operator's Instructions, dated 2000.
Fresenius 90/2 PD Cycler Set Patient Information Card.
Fresenius Freedom Cycler Operating Instructions.
U.S. Appl. No. 10/155,660, filed May 24, 2002, Bowman, Jr. et al.
U.S. Appl. No. 10/155,753, filed May 24, 2002, Hopping.
U.S. Appl. No. 10/155,752, filed May 24, 2002, Busby et al.
U.S. Appl. No. 10/155,787, filed May 24, 2002, Busby et al.
Opening Expert Witness Report of Dr. Juan Santiago Regarding Anticipation and Obviousness of the Claims of U.S. Patents Nos. 6,503,062 and 6,808,369 in view of the Prior Art and based on the Indefiniteness, Lack of Enablement, and Lack of Written Description of Certain Claims of U.S. Patent Nos. 6,503,062 and 6,808,369, Apr. 24, 2009.

Opening Expert Witness Report of William K. Durfee Regarding whether Certain Claims of U.S. Patent No. 5,324,422, U.S. Patent No. 5,421,823, U.S. Patent No. 5,431,626 and U.S. Patent No. 5,438,510 were Ready for Patenting, Apr. 24, 2009.
Expert Witness Report of Fred K. Forster: Analysis of Obviousness of Certain Asserted Claims of U.S. Patent Nos. 5,431,626; 5,324,422; and 5,438,510, Apr. 24, 2009.
Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.
Exhibit A, Credentials of Ronald J. Adrian.
Exhibit B, Materials Considered by Ronald J. Adrian.
Expert Report on Development of the PD700 and Motivation to Combine the PD700 and U.S. Patent No. 5,088,515, Sven Olofsson, Apr. 24, 2009.
Expert Witness Report of Juan G. Santiago Regarding Lack of Written Description, Non-Enablement, and Indefiniteness of the Asserted Claims of U.S. Patent Nos. 5,421,823; 5,324,422; 5,438,510; and 5,431,626, Apr. 24, 2009.
Opening Expert Witness Report of Dr. Martin Roberts Regarding a History of Peritoneal Dialysis and the Obviousness and Consequent Invalidity of the Asserted Claims of U.S. Patent No. 5,421,823, Apr. 24, 2009.
Opening Expert Witness Report of Dr. Darrell Long Regarding Technical Features of the High Flow Peritoneal Dialysis and Personal Cycler Machines, Apr. 24, 2009.
Defendants' Preliminary Invalidity Contentions for U.S. Patent No. 5,421,823 Aug. 24, 2007.
Appendix A: U.S. Patent No. 3,620,215 Alone and in Combination with Other Prior Art References.
Appendix B: Pericycle Product and References Describing the Pericycle in Combination with Other Prior Art References.
Appendix C: U.S. Patent No. 4,412,917 in Combination with Other Prior Art References.
Appendix D: U.S. Patent No. 4,498,900 in Combination with Other Prior Art References.
Appendix E: U.S. Patent No. 3,545,438 in Combination with Other Prior Art References.
Appendix F: U.S. patent No. 5,004,459 in Combination with Other Prior Art References.
Appendix G: Bilstad and Kruger References Together or in Combination with Other Prior Art References.
Appendix H: Combination of 90/2 and Bilstad Together, or in Combination with Other References.
Appendix I: French Patent Nos. 2,371,931 and 2,240,740 in Combination with Other Prior Art References.
Appendix J: AP Hauni References in Combination with Other Prior Art References.
Appendix K: The SIF 901 References in Combination with Other Prior Art References.
Appendix L: "PD in the 90s" in Combination with Other Prior Art References.

\* cited by examiner

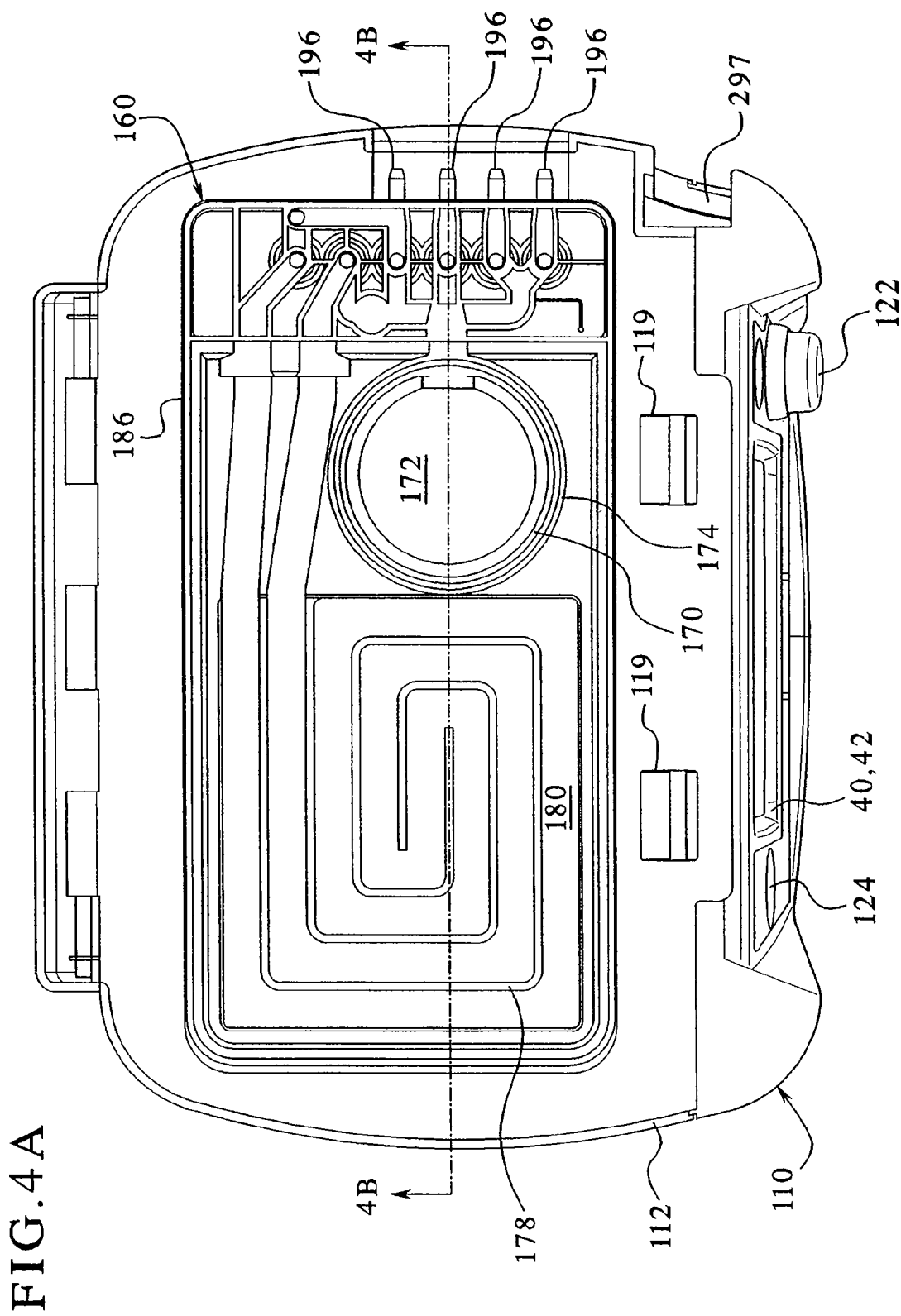

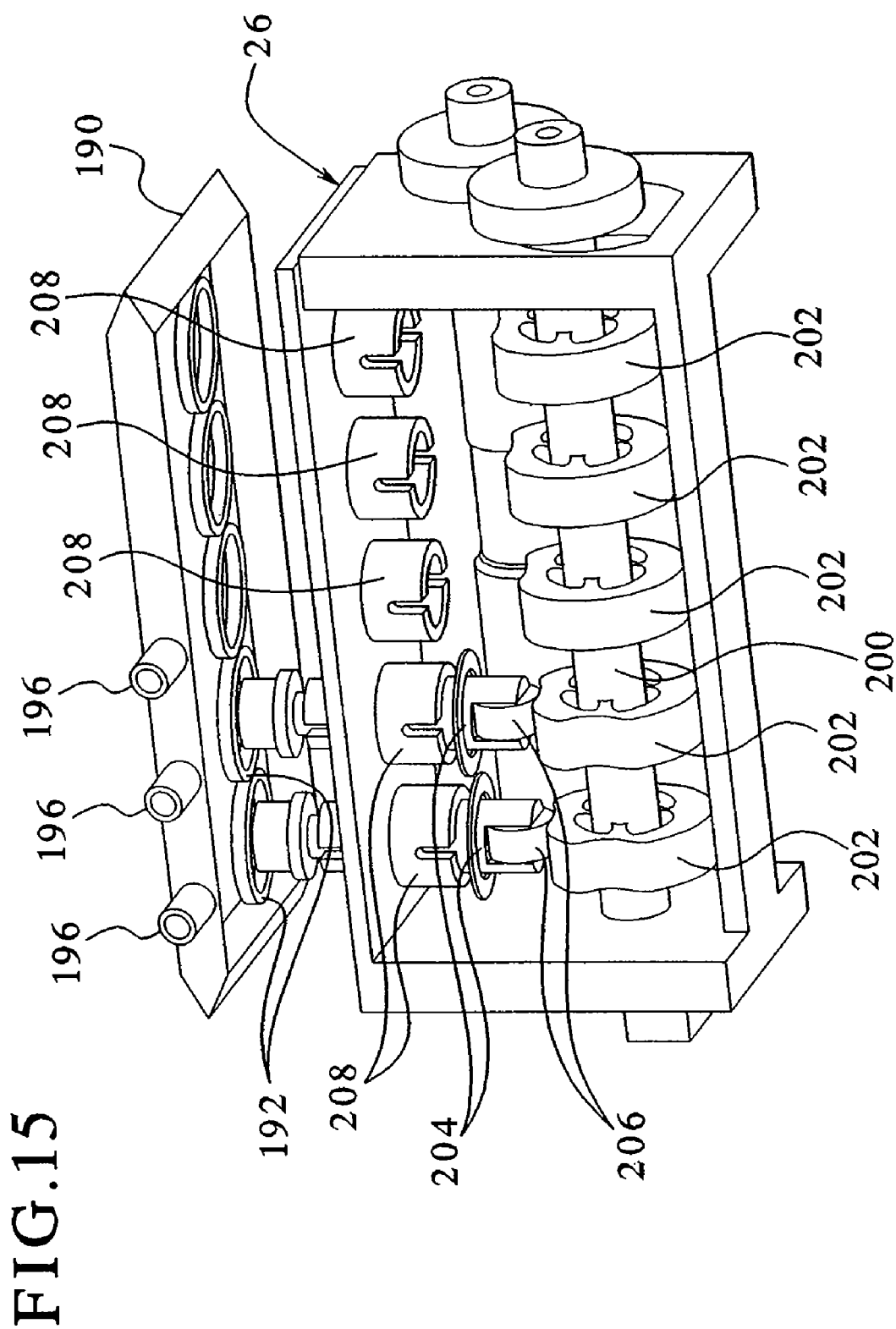

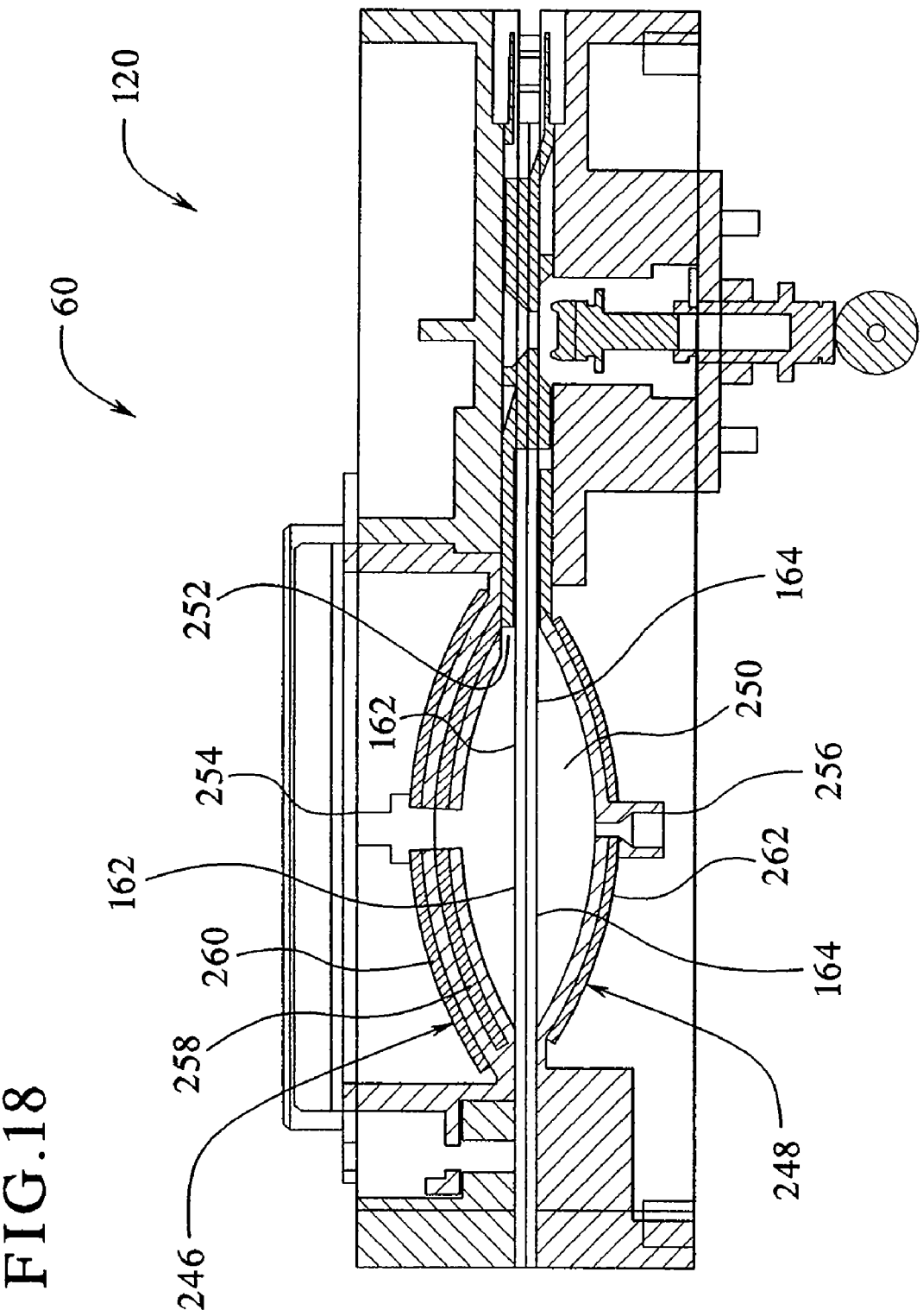

FIG. 24

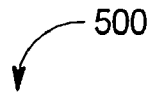
500

| Parameter | Effect |
|---|---|
| Begin Stroke Acceleration | Big impact on overshoot but undesirable from standpoint of stroke time. |
| Proximity Threshold | Good method but may need to be set far below pressure set point. |
| DP/dt | Look at rate of change of pressure and limit to reset to the new velocity setpoint. |
| Max. Travel Velocity | May or may not effect result depending on the initial setting. |
| Conversion to Pressure Deceleration | Potential large impact |
| Kp | Will affect in significant ways the overshoot once the proximity threshold is reached, however, it also affects the entire control to pressure PID control period of the pulse. |
| Kd | Will affect in small ways the overshoot once the proximity threshold is reached, however, it also affects the entire control to pressure and PID control period of the pulse. |
| Ki | Will affect in small ways the overshoot once the proximity threshold is reached, however, it also affects the entire control to pressure and PID control period of the pulse. |

486 — Begin Stroke Acceleration
488 — Proximity Threshold
490 — DP/dt
492 — Max. Travel Velocity
494 — Conversion to Pressure Deceleration
496 — Kp
498 — Kd
502 — Ki

METHOD OF MAKING A PERITONEAL DIALYSIS THERAPY MACHINE

PRIORITY CLAIM

This application claims priority to and the benefit as a continuation application of U.S. patent application "Disposable Medical Fluid Unit Having Rigid Frame," Ser. No. 10/155,384 filed May 24, 2002.

BACKGROUND OF THE INVENTION

The present disclosure generally relates to dialysis systems. More specifically, the present disclosure relates to automated peritoneal dialysis systems. The present disclosure also relates to methods of performing automated peritoneal dialysis and devices for performing same.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis peritoneal dialysis are two types of dialysis theriapies commonly used to treat loss of kidney function. Hemodialysis treatment utilizes the patient's blood to remove waste, toxins and excess water form the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about 120 liters, is used to dialyze the blood during a single hemodialysis therapy. The spent dialysate is then discarded. Hemodialysis treatment lasts several hours and is generally performed in a treatment center about three or four times per week.

Peritoneal dialysis utilizes a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD"), automated peritoneal dialysis and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. Manual peritoneal dialysis performed by the patient requires a significant amount of time and effort from the patient. This inconvenient procedure leaves ample room for improvement and therapy enhancements to improve patient quality of life.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines fluidly connect to an implanted catheter. The APD machines also fluidly connect to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. APD frees the patient from having to manually performing the drain, dwell, and fill steps.

However, continuing needs exist to provide improved APD systems. For example, needs exist to provide simplified APD systems that are easier for patients to use and operate. Further, needs exist to provide lower cost APD systems and APD systems which are less costly to operate. Particularly, needs exist to clinically, economically and ergonomically improve known APD systems.

APD systems need to be improved for home use. One common problem with current home systems is that they are susceptible to electrical shock due to "leakage current". Current that flows from or between conductors insulated from one another and from earth is called "leakage current". If any conductor is raised to a potential above earth potential, then some current is bound to flow from that conductor to earth. This is true even of conductors that are well insulated from earth, since there is no such thing as perfect insulation or infinite resistance. The amount of current that flows depends on: (i) the potential, (ii) the capacitate reactance between the conductor and earth and (iii) the resistance between the conductor and earth.

For medical equipment, several different leakage currents are defined according to the paths that the leakage currents take. An "earth leakage current" is the current which normally flows in the earth conductor of a protectively earthed piece of equipment. In medical equipment, impedance to earth from an enclosure is normally much lower through a protective earth conductor than it is through the patient. However, if the protective earth conductor becomes open circuited, the patient could be at risk of electrical shock.

"Patient leakage current" is the leakage current that flows through a patient connected to an applied part or parts. It can either flow from the applied parts via the patient to earth or from an external source of high potential via the patient and the applied parts to earth. Other types of leakage currents include "enclosure leakage current", and "patient auxiliary current".

Leakage currents are normally small, however, the amount of current required to produce adverse physiological effects in patients is also small. Accordingly, leakage currents must be limited as much as possible by the design of the equipment and be within safety limits.

SUMMARY OF THE INVENTION

Generally, the present disclosure provides improved dialysis systems and improved methods of performing dialysis. More particularly, the present disclosure provides systems and methods for performing automated peritoneal dialysis ("APD"). The systems and methods of the present disclosure automatically provide dialysis therapy by providing dialysis fluid to the patient and draining spent dialysis fluid from the patient.

Also, the systems and methods of the present disclosure can perform various dialysis therapies. One example of a dialysis therapy which can be performed according to the present disclosure includes an automatic dialysis fluid exchange of a patient fill, dwell and a patient drain. The dialysis system of the present disclosure can automatically perform dialysis therapy on a patient, for example, during nighttime while the patient sleeps.

To this end, in an embodiment a dialysis system is provided. The system includes a fluid supply line. A disposable unit is in fluid communication with the fluid supply line. The disposable unit has at least two flexible membranes that bond together at selected locations and to a rigid plastic piece or manifold. The membranes can be single or double layer. One suitable membrane material is described herein. The membranes seal to one another so as to define a fluid pump receptacle and a fluid heating pathway. The membranes and plastic manifold define a number of flexible valve chambers. The disposable unit also fluidly communicates with a patient line and a drain line.

The manifold and other areas of the disposable unit include reduced or tapered edges that provide an area to seal the membranes. The reduced thickness or tapered area requires less heat than the full thickness, which reduces the heat sinking disparity between the thickness of the manifold of the disposable unit and the thinner flexible membranes. The frame of the manifold is bowed or curved to provide rigidity. The frame is also asymmetrical and designed to be placed into the hardware unit in only one direction.

The hardware unit can be manually transported to a patient's home and opened so that the patient can place a disposable unit therein and closed so that the dialysis unit and the disposable unit cooperatively form a pump chamber that enables dialysis fluid to be pumped to and from the patient. The hardware unit has an enclosure that defines a pump shell, a valve actuator and a heater. The disposable unit is placed in and removed from the enclosure. The fluid pump receptacle of the disposable unit and the shell of the hardware unit form a pump chamber. The pump chamber operates with a pump actuator, which is also located inside the transportable hardware unit.

When packaged, a plurality of tubes extend from the disposable unit. The ends of the tubes have connectors that attach to a single body. The body defines or provides a plurality of tip protectors that hold the tubes in an order according to steps of the therapy. The body is configured to slide into the hardware unit of the system from one direction, so that a patient can readily pull the tubes and connectors from the tip protector organizer.

The tip protector used to house the patient fluid connector includes a hydrophobic filter that allows air but not fluid to escape. This vented tip protector enables the system to be primed without having to perform elevation balancing or controlled fluid metering. The system performs a prime by flowing fluid through the system and into the patient fluid line until the dialysate backs up against the filter, causing a fluid pressure increase, which is sensed by the system. The system then stops the pump.

The hardware unit also provides a controller. The controller includes a plurality of processors, a memory device for each processor and input/output capability. One of the processors coordinates operation of the pump actuator, the valve actuator and the heater with the various stages of dialysate flow, such as the fill, dwell and drain stages. The processor also controls or obtains feedback from a plurality of different types of sensors. The sensors include, among others, a capacitance fluid volume sensor, a dialysis fluid temperature sensor, a pressure sensor, a vacuum sensor, an air detection sensor and a mechanical positioning sensor.

In an embodiment, the system uses both preset motion control and adaptive pressure control to control the pressure of fluid within the pump receptacle. The system uses a preset pump motor acceleration to overcome system compliance (i.e., membrane and tubing expansion), which would not otherwise be readily overcome by known proportional, differential or integral control. After the system overcomes compliance, the system converts to an adaptive control using adaptive techniques for controlling pressure by precisely controlling the velocity of a pump motor shaft. The adaptive parameters are modified over time to fine tune the system. This method is especially important for the patient fill and drain cycles, wherein the patient can feel pressure fluctuations. The method also readily compensates for pressure variations due to bag height, bag fullness, etc.

The capacitance fluid volume sensor indicates a volume of fluid in the pump chamber, wherein the sensor generates a voltage signal that is indicative of the volume of fluid in the receptacle. The controller receives the voltage signal and converts the signal into an amount of fluid or an amount of air within the flexible fluid receptacle of the pump chamber.

The pump actuator can be mechanically or pneumatically operated. When mechanically driven, a pump motor drives a vacuum source, such as a piston-cylinder, which pulls a vacuum on the membranes of the fluid receptacle of the disposable unit. Here, a mechanical positioning sensor, such as an encoder, senses the angle of a pump motor shaft relative to a home position and sends a signal to the controller, wherein the controller can adjust the pump motor accordingly. The encoder also provides safety feedback to the controller, whereby the controller, once therapy starts, prevents the camshaft from rotating to a position where the valves can free fill the patient. When the pump actuator is pneumatically operated, the system in an embodiment uses a vacuum pump to pull apart the membranes of the fluid receptacle. Here, the system uses a vacuum sensor to sense the state of the vacuum pump and a mechanical sensing device, such as a linear encoder, to sense the state of a pump piston.

Thus, in an embodiment, the system maintains a negative pressure on one of the membranes of the fluid receptacle of the disposable unit to pull same away from the other membrane and draw dialysis fluid into the fluid receptacle. The negative pressure on the active membrane is then released, which pushes the membrane towards the other membrane and dispels the dialysis fluid from the pump receptacle. In another embodiment, a mechanical pump piston can be pneumatically attached to one of the membranes, wherein the system mechanically pulls the membrane away from the other membrane. In an embodiment, the membrane is coupled to the pump piston through negative pressure. The pump also includes a diaphragm that is pulled to a bottom side of the piston head, wherein the membrane is pulled to a top side of same. In a further embodiment, the system mechanically pushes one of the membranes while applying the negative pressure to same.

The system also performs other necessary tasks automatically. For example, the system automatically heats the dialysate to a desired temperature while pumping dialysate to the patient. The heater heats the fluid heating pathway defined by the flexible membranes of the disposable unit. In an embodiment, the heater includes an electrical heating plate. Alternatively, or in addition to the heating plate, the heater includes an infrared heating source. In an embodiment, the fluid heating pathway and the heater define an in-line heater that heats dialysate as it travels from the supply bag to the patient.

The system employs a method of heat control that uses a knowledge-based algorithm and a fuzzy logic based algorithm. The former uses laws of physics, empirical data and sensed inputted signals. The latter inputs a difference between desired and actual temperatures and uses fuzzy logic membership functions and fuzzy logic rules. Each algorithm operates at a different update frequency. Each algorithm outputs a duty cycle, wherein the system weights the fuzzy logic based duty cycle relative to the knowledge based duty cycle and produces an overall heater control duty cycle. This method enables accurate dialysate temperature control.

The system automatically purges air from the dialysate, for example, through the pump chamber. The system also senses a total volume of fluid pumped to the patient, records and logs same. Furthermore, the system knows the instantaneous flow rate and fluid pressure of fluid entering or leaving the patient's peritoneal cavity.

The disposable unit includes a valve manifold. The manifold defines a plurality of valve chambers. The hardware unit includes a valve actuator that selectively and sequentially presses against one or more of the valve chambers. In an embodiment, a mechanically operated valve actuator includes a single camshaft and a plurality of cams. The cams press against one of the membranes of the disposable unit to engage the other membrane and block or disallow fluid flow. As stated above, the system uses a sensing device, such as a rotary encoder, to sense the angle of the camshaft relative to a home position, so that the controller can rotate the camshaft to open or close one or more valves as desired. The single camshaft toggles back and forth between: supply and pump chamber fill positions; patient drain and system drain positions; and between pump chamber fill and patient fill positions. These positions are actuated by a unique rotational position on an overall cam profile (i.e., the superposition of each of the individual cams as seen from the end of the camshaft).

The disposable unit of the present disclosure is provided in a variety of different forms. In an embodiment, the portion of the disposable unit forming the heating path is formed by the same membranes that seal to the rigid member or manifold that forms the valve chambers. The same membranes also form the pump receptacle. In another embodiment, the disposable unit includes a first set of membranes that form the pump receptacle and the valve manifold via the rigid member. Here, the disposable unit includes a second set of membranes, distinct from the first membranes, which form the fluid heating path. In an embodiment, medical grade tubing connects the first set of membranes to the second set. In particular, the tubing enables the fluid heating path to fluidly connect to the valve manifold.

The disposable unit in another embodiment includes a first flexible membrane and a second flexible membrane that house the pump receptacle, the fluid heating path and the rigid valve manifold. The disposable unit also includes a rigid frame that attaches to at least one of the first and second flexible membranes. The rigid frame enables a patient or operator to place the frame and the disposable unit into the enclosure of the hardware unit of the automated dialysis system. The rigid frame is sized to securely fit into a dedicated place in the enclosure. The rigid frame further holds the disposable unit stable while the patient or operator connects tubes to same. For example, the valve manifold provides ports or other types of connectors for connecting to a supply line, a drain line and a patient line. In an embodiment, the rigid frame extends around or circumvents the membranes including the pump receptacle, fluid heating path and valve manifold. In an embodiment, the rigid frame is plastic. In an embodiment, the rigid frame is bowed along at least two sides to increase the rigidly of the disposable unit and to keep the disposable unit from deforming during the heat sealing portion of its manufacture.

In an embodiment, the rigid member or manifold of the disposable unit includes interfaces that allow the membranes to be more easily sealed to the manifold. The manifold edges are tapered to reduce the heat needed to form a cohesive bond between the membranes and the plastic valve manifold. The knife-like tapered edges also reduce or eliminate the gap between the top and bottom membranes, which minimizes the opportunity for leaks to occur in the disposable unit. The chamfered edges also reduce the likelihood that the heat sealing process will burn through the membranes.

The hardware unit described above includes a display device that provides dialysis system information. The display device also enables the patient or operator to enter information and commands into the controller. For example, the display device can include an associated touch screen that enables the patient or operator to initiate automatic flow of the dialysate through the disposable unit. The system begins to pneumatically and/or mechanically pump dialysate through the pump chamber, past the in-line heater and into the patient's peritoneal cavity. Thereafter, the system automatically runs the other cycles of dialysis therapy, for example, while the patient sleeps and/or at night. The automated system not only transfers dialysate from a supply container to the patient, the system allows the dialysate to dwell inside the patient for an amount of time and automatically operates to transfer the dialysate from the patient to a drain.

The system provides a graphical user interface ("GUI"). The GUI in an embodiment employs an embedded web browser and an embedded web server. The web browser and server operate on a main microprocessor for the system. The GUI also employs instrument access and control software, which operates on the main system processor and on one or more delegate processors. The instrument access and control software controls lower level devices, such as the heater and the pump. The GUI also provides intermediate software that allows the web browser to communicate with the instrument access and control software.

The GUI displays a number of therapy set-up screens and a number of dialysis treatment screens. The set-up screens generally walk the patient through the set-up portion of the therapy. The system waits for an operator input before proceeding to the next set-up screen. The set-up screens provide information to the patient in the form of real-life images of the equipment and through animations of the actions needed to connect the system to the patient.

The therapy treatment screens display the various cycles of the therapy to the patient in real-time or substantially in-real time. The therapy treatment screens display information such as cycle time in both a graphical and quantitative manner. The therapy treatment screens do not require input from a patient, who may be sleeping while these screens are displayed. When the therapy is complete, the system once again displays a number of disconnection screens which, like the set-up screens, wait for an input from the patient before performing an action.

The treatment screens are colored and lighted for night time viewing, and may be easily seen from a distance of about ten to fifteen feet, however, the screens are lighted so as not to wake a sleeping patient. In an embodiment, the background of the screens is black, while the graphics are ruby red. In contrast, the set-up screens are lighted and colored for daytime viewing.

With the above embodiments, one advantage of the present disclosure is to provide improved systems and methods for performing dialysis.

Another advantage of the present disclosure is to provide improved systems and methods for performing peritoneal dialysis.

A further advantage of the present disclosure is to provide an automated peritoneal dialysis system and method of operating same.

Still another advantage of the present disclosure is to provide an automated peritoneal dialysis system that provides dialysis therapy advantages.

Still a further advantage of the present disclosure is to provide an automated peritoneal dialysis system that has economic advantages.

Yet another advantage of the present disclosure is to provide an automated peritoneal dialysis system that has quality of life advantages.

A still further advantage of the present disclosure is to provide a disposable unit having bowed sides, which increase rigidity and decrease flexing of disposable unit.

Moreover, an advantage of the present disclosure is to provide a disposable unit having tapered interfaces that decrease the heat sinking of the semi-rigid manifold and provide a more robust seal.

Various features and advantages of the present disclosure can become apparent upon reading this disclosure including the appended claims with reference to the accompanying drawings. The advantages may be desired, but not necessarily required to practice the present invention.

BRIEF DESCRIPTION OF THE FIGURES

FIG. 4A is a plan view of one embodiment of the hardware and disposable units of the present disclosure.

FIG. 15 is a perspective view of one embodiment of a valve actuator in combination with the fluid manifold of the present disclosure.

FIG. 18 illustrates an alternate embodiment of a fluidly operated fluid pump and capacitance sensor of the present disclosure.

FIG. 24 is a table illustrating one set of the correction parameters illustrated in connection with FIG. 23.

DETAILED DESCRIPTION OF THE INVENTION

The present disclosure relates to dialysis systems and methods of performing dialysis. In particular, the present disclosure relates to a system and method for automatically providing peritoneal dialysis therapy to patients. The present disclosure provides automatic multiple exchanges of dialysis fluid to and from the patient's peritoneal cavity. The automatic exchanges of dialysate include drain, fill, and dwell periods, which usually occur while the patient sleeps. A typical therapy can include three to five exchanges of dialysis fluid. The present disclosure, in an embodiment, provides a single pass system, wherein the dialysate passes through the peritoneal cavity only once before being disposed. While the present disclosure performs peritoneal dialysis, it is also suitable for other types of dialysis and other medical fluid transfer operations.

I. The System Generally

Figure 1:
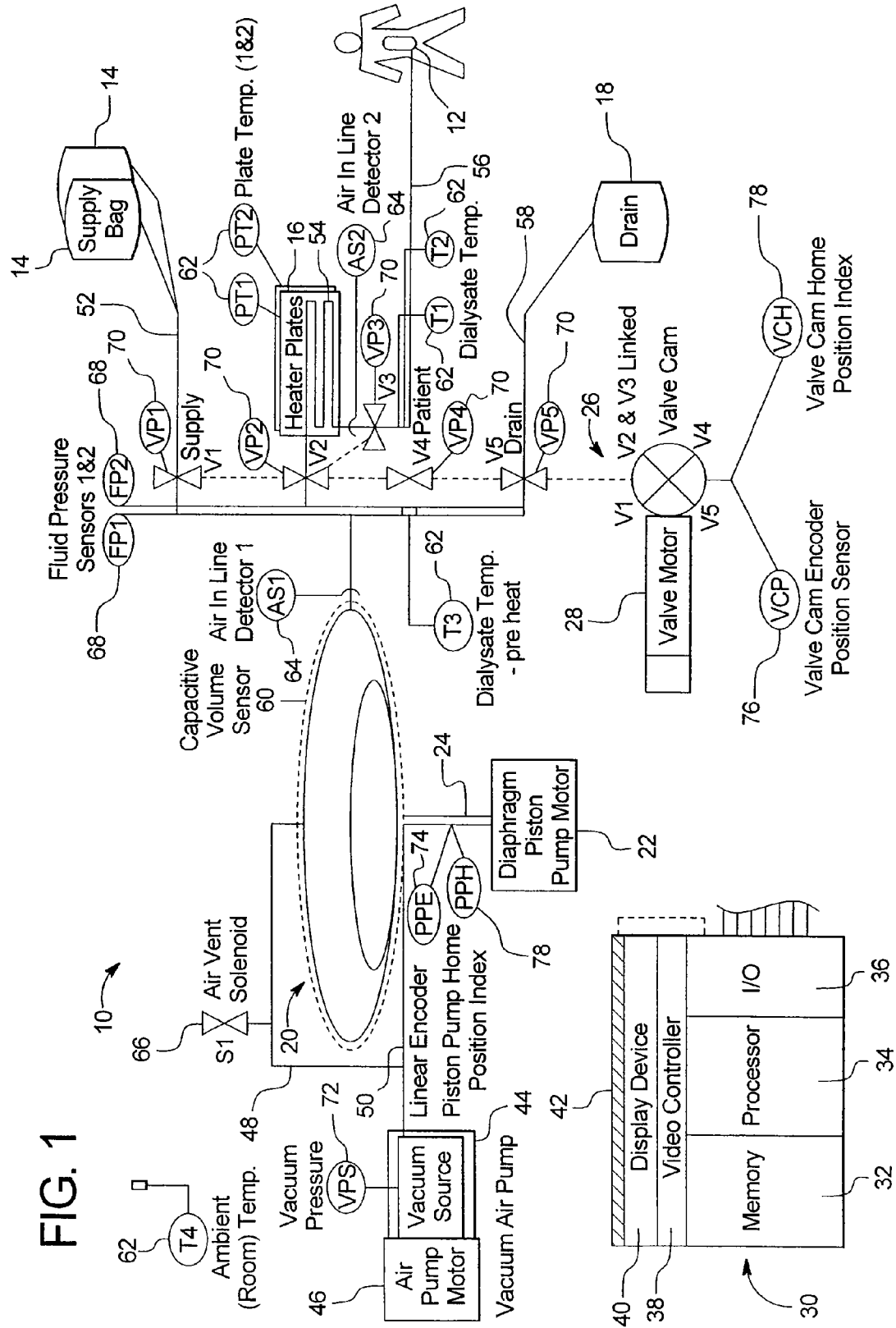
FIG. 1 schematically illustrates an embodiment of an automated dialysis system of the present disclosure having a mechanically actuated fluid pump.

Referring now to the drawings and in particular to FIG. 1, a typical therapy performed by the system 10 of the present disclosure begins by draining dialysis solution that is already in the patient's peritoneal cavity 12. The system 10 pumps fresh dialysate from one of a plurality of supply bags 14, through an in-line heater 16 to the patient or peritoneal cavity 12. After a dwell period in the peritoneal cavity 12, the spent dialysate in the cavity is pumped out of the patient or cavity 12 to a drain 18 or other disposal means. The system 10 then pumps fresh dialysate from the supply bags 14 to the patient or peritoneal cavity 12 and the procedure is repeated as defined in the therapy protocol. The system 10 in an embodiment pumps a last bag of dialysate (usually, a dialysate having a different formulation than the dialysate in the other supply bags) to the peritoneal cavity 12 for an extended dwell, such as a daytime dwell.

In an embodiment, the system 10 includes a mechanically operated diaphragm pump 20. The mechanically operated diaphragm pump 20 employs a pump motor 22 and a linear pump actuator 24. A vacuum may also be used with the mechanical actuator for the diaphragm pump 20, as described in further detail below. In another embodiment illustrated in FIG. 2, the pump is completely fluidly activated.

In FIG. 1 the system 10 also includes a valve actuator 26, which mechanically actuates valves V1 to V5. A controller 30 controls the valve actuator 26 to open valves V1 to V5 as necessary to achieve the desired direction of dialysate fluid flow. In an embodiment, the valve actuator 26 includes a valve motor 28 and a camshaft (illustrated below), which opens one or more of the valves V1 to V5 to achieve the desired dialysate flow.

The controller 30 includes a plurality of processors and a memory device for each processor. The processors include a main microprocessor and a number of delegate processors. The main microprocessor runs certain higher level tasks such as the graphical user interface ("GUI") described below. The delegate processors perform lower level tasks, such as moving valves, reading sensors, controlling heater duty cycle, etc. An additional processor is provided solely for the purpose of tracking safety parameters, such as heater plate and medical fluid temperature. For purposes of the present disclosure, except where otherwise specified, the term "processor 34" refers collectively to all of the processors and the term "memory device 32" refers collectively to all of the corresponding memory devices.

The controller 30 also includes an input/output ("I/O") module 36. The memory device 32 stores a computer program that contains a step by step sequence for the system 10 and configures certain outputs to occur upon specified inputs. The processor 34 runs the program in the memory device 32. The I/O module 36 accepts signal lines from various sensors. The I/O module 36 also connects to power lines including input power lines (including if battery powered) and power lines outputted to the various electrical components.

The controller 30, in an embodiment, includes a video controller 38, which may be a video card. The controller 30 also includes a display device or video monitor 40 that displays medical treatment or dialysis information to a patient or operator. In an embodiment, the controller 30 further includes a touch screen 42 that interfaces with the video monitor 40 and electrically communicates with the I/O module 36. The touch screen 42 enables the patient or operator to input medical treatment or dialysis information into the controller 30.

The controller 30 controls the heater 16, the pump 20 and the valve actuator 26 in a number of different phases that make up a single medical or dialysis treatment. In a first pump fill phase, controller 30 activates the pump 20 to pump medical fluid or dialysate from one of the supply bags 14. In FIG. 1, the controller 30 commands a vacuum source 44, including an air pump motor 46, to pull a vacuum on both sides of the pump 20 through a first vacuum line 48 and a second vacuum line 50. The vacuum lines 48 and 50 pull respective vacuums through first and second pump chamber walls to suction one of a pair of opposing membranes inside the pump chamber against the interior of the pump chamber. The other membrane is held against a piston head in the pump 20. The other membrane alternatively temporarily or permanently mechanically attaches to the piston head, rendering the vacuum on the piston side of the pump 20 unnecessary.

With the membranes maintained against the interior of the pump chamber and the piston head, the controller 30 commands the linear actuator 24 to withdraw within the pump 20. The withdrawal causes the membranes inside the pump chamber to pull further apart. At this time, the controller 30 controls the valve actuator 26 so that only valve V1 is open. The pulling apart of the membranes causes a negative pressure to occur in fill line 52, wherein the negative pressure pulls medical fluid or dialysate from the supply bag 14, through the fill line 52, into a receptacle created by the opened membranes inside the pump chamber of pump 20.

In a patient fill phase, with the negative pressure still maintained by the vacuum source 44, through the pump chamber walls, on the interior membranes, the controller 30 causes the linear pump actuator 24 to move upwards within the pump 20. The upward movement of the actuator 24 and an attached piston head provides a positive mechanical pressure that closes the membrane receptacle and thereby pumps the medical fluid out of the pump 20. At this time, the controller 30 controls the valve actuator 26 so that only valves V2 and V3 are open. Consequently, all of the fluid exiting pump 20 is pumped through a heater line 54, past the in-line heater 16, through a catheter line 56, and into the patient, for example, the patient's peritoneal cavity 12. The catheter line 56 in an embodiment connects to a single lumen catheter, which is implanted into the patient 12. Although, in other embodiments, the system 10 can employ a multi-lumen catheter.

The heater 16 in an embodiment includes one or more electrical heating plates, which heat the medical fluid to roughly body temperature. The controller 30 energizes and de-energizes the heater 16 as necessary to obtain the proper fluid temperature. The controller 30 can close valves V2 and V3, located on opposing sides of the heater 16 in the heater line 54, if the medical fluid is too hot or too cold. The improperly heated dialysate does not enter the peritoneal cavity 12.

The controller 20 repeats the pump fill phase and the heater fill phase until the patient's the peritoneal cavity 12 becomes full of fluid according to the therapy protocol. In an embodiment, the volume inside the pump is about thirty to fifty milliliters, and an adult patient typically uses about two liters of dialysis fluid. Accordingly, the pump fill phase and the heater fill phase can be repeated on the order of fifty times. In an embodiment, the pump actuator 24 maintains a fluid pressure at the pump 20 of about three pounds per square inch ("psi").

The system 10 provides a fluid volume sensor 60, which measures the actual volume of medical fluid that has been forced through the pump 20. By summing multiple individual pump volumes, the controller accurately knows how much medical fluid or dialysate has been delivered to the patient 12. The system 10 in an embodiment repeats the pump fill phase and the heater fill phase until the pump 20 has delivered a predetermined volume of medical fluid. The predetermined volume can be inputted into the controller 30 by a patient or operator via the touch screen 42.

In a dwell phase, the controller 30 lets the medical fluid or dialysate remain within the patient 12 for an amount of time, which can be controlled by the controller 30, the patient 12 or an operator. In an embodiment, the controller 30 determines the dwell time, but the patient 30 or operator can override the system 10 and command that the system 10 remove the medical fluid from the patient 12.

In a second pump fill phase, the medical fluid is removed from the patient 12. The controller 30 and the actuator 26 open valve V4, while shutting the remaining valves. With the vacuum source still maintaining a negative pressure on the membranes inside the pump 20, the linear actuator 24 withdraws the pump piston within the chamber of pump 20 and reopens the receptacle between the membranes. The negative pressure created by the opening receptacle pulls the medical fluid from the patient 12, through the catheter line 56 and into the membrane receptacle formed inside the pump 20.

In a drain phase, with the negative pressure still maintained by the vacuum source 44, through the pump chamber walls, on the interior membranes, the controller 30 causes the linear pump actuator 24 to move upwardly within the pump 20. The upward movement of the actuator 24 causes a positive mechanical pressure to close the membrane receptacle and thereby pump the medical fluid out of the pump 20. At this time, the controller 30 controls the valve actuator 26 so that only valve V5 is open. Consequently, all of the fluid exiting pump 20 is pumped through a drain line 58 and into the drain 18. Drain 18 can be a drain bag or a drain pipe inside a home, a hospital or elsewhere.

One embodiment of the fluid volume sensor 60 is described in more detail below in connection with the description of the diaphragm pump 20. Besides the fluid volume sensor 60, the system 10 includes various other desired types of sensors.

The system 10 includes temperature sensors 62, such as the sensors T1 to T4, which measure the temperature at relevant places within the system 10. In an embodiment, the sensors 62 are non-invasive, however, any other types of temperature sensors may be employed. As illustrated in FIG. 1, sensors T1 and T2 provide redundant post heater feedback of the fluid temperature to the controller 30. Sensor T3 provides a temperature of the medical fluid prior to heating. Sensor T4 provides the ambient temperature.

The system 10 also provides temperature sensors 62 that monitor the temperature of the heater 16. In an embodiment, the heater 16 is an in-line plate heater. The in-line plate heater 16 can have one or more heater plates, for example, two heater plates having a disposable unit placed between same. Separate temperature sensors PT1 and PT2 are provided to monitor the temperature of each of the plates of the plate heater. The system 10 can thereby control each plate heater individually.

The system 10 includes one or more air sensors 64, such as the sensor AS1, placed directly at the throat of the inlet and outlet of the pump 20. Another air sensor AS2 monitors air in the medical fluid after it leaves the heater 16 and just before the final shut-off valve V3 leading to the catheter line 56. The controller 30 monitors the air content sensed by the air sensors 64 and thereby controls the system 10 to perform any necessary air purge. The system 10 can separate and discharge the air from the fluid or simply convey the air to the drain 18. The system 10 also includes an air vent solenoid 66, which is operated by the controller 30. The air vent solenoid 66 enables the system 10 to relieve the vacuum applied to one or both of the membranes in the pump 20.

The system 10 can accumulate air for various reasons. For example, the valves V1 to V5 and fluid lines, such as lines 52, 54, 56 and 58 may contain air prior to priming the system 10. The supply bags 14 may also introduce air into the pump 20. The patient 12 can also produce certain gasses, which become entrained in the dialysate and enter the pump 20. Further, if minor leaks exist in the fluid disposable or the connections to the supply bag 14, the catheter at the patient 12, or the drain bag, the pump 20 can draw air in through the leaks.

The system 10 provides various fluid pressure sensors 68. Fluid pressure sensors FP1 and FP2 provide a redundant pressure reading of the fluid in the fill line 52 leading to the pump 60. The fluid pressure sensors 68 provide a signal to the controller 30 that indicates the respective fluid pressure at that location. Based on the signals from the pressure sensors FP1 and FP2, the controller 30 operates the fluid pumps and valves to obtain and maintain a desired fluid pressure. As stated above, the system 10 maintains the pump pressure, for example, at about three psi.

The system 10 also provides various valve pressure sensors 70. Valve pressure sensors VP1 to VP5 detect the fluid pressure at the valves V1 to V5. The system 10 further provides one or more vacuum pressure sensors 72, for example, at the vacuum source 44, to ensure that a proper vacuum is maintained on the membrane receptacle within the pump 20.

In an embodiment, the fluid pressure, valve pressure and vacuum sensors 68, 70 and 72, respectively, are non-invasive sensors. That is, the sensors do not physically contact (and possibly contaminate) the medical fluid or dialysate. Of course, the system 10 can include other flow and pressure devices, such as flow rate sensors, pressure gauges, flowmeters, or pressure regulators in any suitable quantity and at any desired location.

The system 10 also includes various positioning sensors. In an embodiment, the positioning sensors include a linear encoder 74 that monitors the position of the linear pump actuator 24 and a rotary encoder 76 that monitors the angular position of the valve actuator 26 or camshaft. An encoder is one type of positioning feedback device that can be employed. Other types of positioning feedback systems include proximity sensors and magnetic pick-ups that sense a pulse, e.g., a gear tooth of a gear attached to the camshaft, and output the pulse to a counter or microprocessor.

The encoders 74 and 76 also typically provide a pulsed output, which is sent to the controller 30. The pulsed output tells the controller 30 how many steps or how far the linear pump actuator 24 or the valve actuator 26 is from a home position or home index 78. For example, the home position 78 can be the pump fully open or pump fully closed position for the linear encoder 74 and the zero degree position for the rotary encoder 76.

In an embodiment, the encoders 74 and 76 are absolute type encoders that know the location of the home position 78 even after a power loss. In another embodiment, the encoders 74 and 76 are incremental encoders and a battery back-up is provided to the controller so that the system 10 can maintain the location of the home position 78 even when no external power is applied. Further alternatively, system 10 can be programmed to automatically move the pump actuator 24 and the valve actuator 26 upon power-up until a home position is sensed, wherein the system 10 can begin to run the main sequence.

Figure 2:
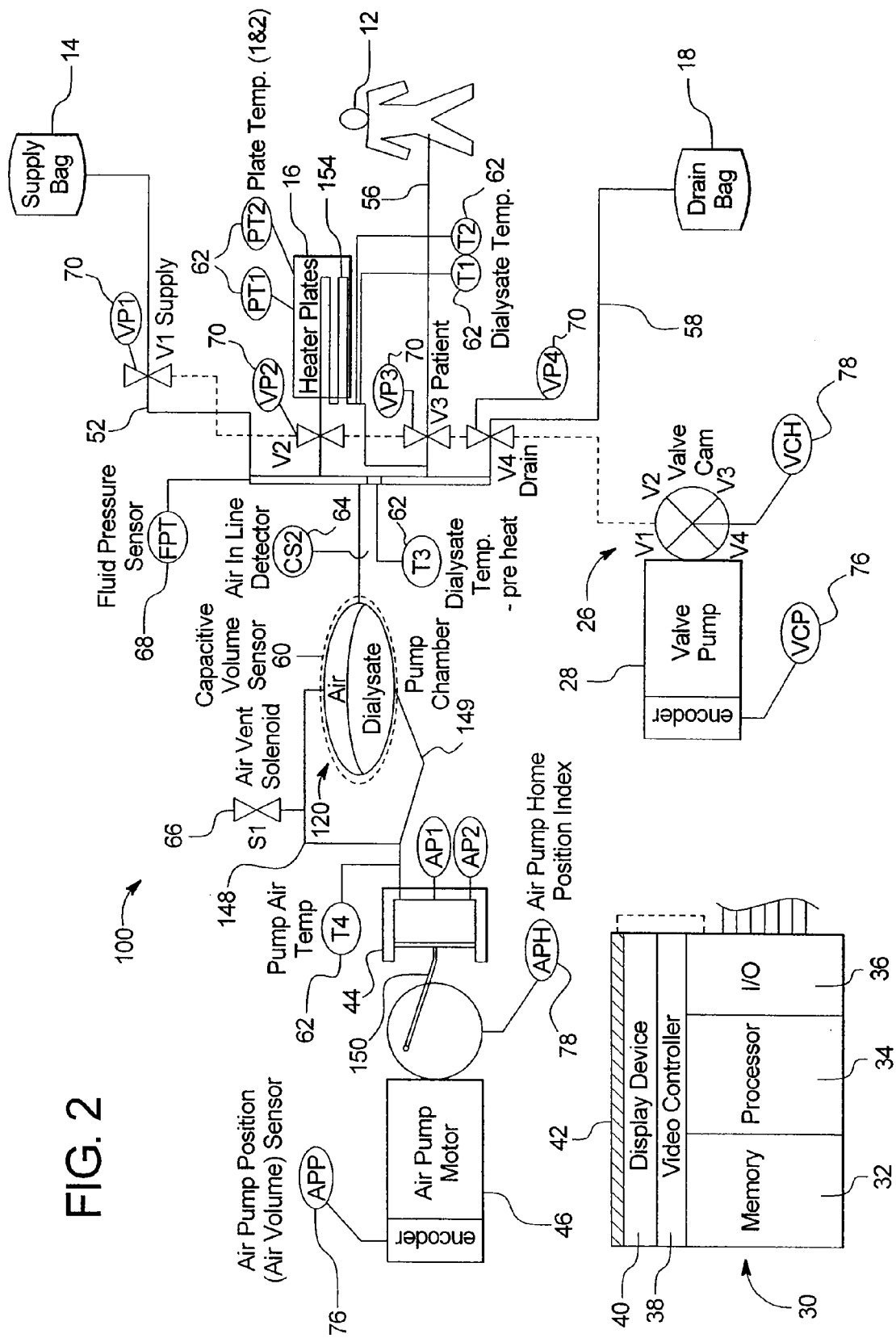
FIG. 2 schematically illustrates another embodiment of an automated dialysis system of the present disclosure having a fluidly actuated fluid pump.

Referring now to FIG. 2, an alternative system 100 is illustrated. The system 100 includes many of the same components having the same functionality (And the same reference numbers) as previously described. These components therefore do not need to be described again except to the extent that their functioning with the new components of system 100 differs. The primary difference between the system 100 and the system 10 is that the pump 120 of the system 100 is completely fluidly actuated and does not use the linear pump actuator 24 of the system 10.

In the pump fill phases, described above, the controller 30 activates the pump 120 to pump medical fluid or dialysate from one of the supply bags 14. To do so, the controller 30 commands vacuum source 44 (shown separately from motor 46 in FIG. 2), including a vacuum pump motor 46, to pull a vacuum on both sides of the pump 120, i.e., on both pump membranes, through vacuum lines 148 and 149. The vacuum pump motor 46 in this embodiment includes a rotary encoder 76 and a home position or home index 78. The rotary encoder 76 provides positional feedback of a member 150 within the vacuum source 44. The system 100 therefore knows if the vacuum source 44 can provide any additional suction or if the member 150 has bottomed out within the vacuum source 44.

To draw in medical fluid, the vacuum line 148 pulls a vacuum through first and second pump chamber walls to the pair of opposing membranes inside the pump chamber. The vacuum pulls the membranes against the interior of the pump chamber. At this time, the controller 30 controls the valve actuator 26 so that only valve V1 is open. The pulling apart of the membranes causes a negative pressure to occur in fill line 52, wherein the negative pressure pulls medical fluid or dialysate from the supply bag 14, through the fill line 52, into a receptacle created by the volume between the membranes inside the pump chamber of pump 120.

In an alternative embodiment, the pump 120 maintains a constant vacuum on one of the membranes, wherein the opposing membrane does the pumping work. To pump fluid out, the vacuum on one or both membranes is released. The membranes, which have been stretched apart, spring back to a closed position. This operation is described in detail below.

The system 100 also includes a slightly different valve manifold than the system 10. The system 100 includes one less valve than the system 10, wherein the system 100 does not provide an extra valve (V3 in system 10) directly after the fluid heater 16. Obviously, those of skill in the art can find many ways to configure the valves and fluid flow lines of the systems 10 and 100. Consequently, the configuration of the valves and fluid flow lines of the systems 10 and 100 as illustrated merely represent practical examples, and the present disclosure is not limited to same.

II. Hardware Unit and Disposable Unit

Referring now to FIGS. 3A, 3B, 4A and 4B, both systems 10 and 100 include a hardware unit 110 and a disposable unit 160. The hardware unit 110 in an embodiment is portable and can be transported to and from a person's home. The hardware unit 110 includes a housing 112 that includes a base 114 and a lid 116. In an embodiment, the lid 116 is hinged to the base 114. Alternatively, the lid 116 is completely removable from the base. The lid 116 in either case opens to provide access to the interior of the housing 112, so as to allow the patient or operator to place and remove the disposable unit 160 into and from the hardware unit 110. The hardware unit 110 can be made of any protective, hard, resilient and/or flexible material, for example, plastic or metal sheet, and can have a decorative and/or finished surface.

Once the disposable unit 160 is placed inside the hardware unit 110, the operator closes the lid 116 and uses one or more locking or latching mechanism 118 (FIG. 3B) to safely house the disposable unit 160 within the hardware unit 110. FIG. 4A illustrates members 119 of the housing 112 to which the latching mechanism 118 of the lid 116 attaches. The hardware unit 110 displays the video monitor 40, which can have an associated touch screen 42 to input commands as described above. Alternatively, or in addition to the touch screen 42, the hardware unit 110 can provide one or more electromechanical switches or pushbuttons 43, 124, 125 and 127, analog controls 122 and/or lighted displays. The pushbuttons or switches 43, 124, 125 and 127 and knob 122 enable the patient or operator to input commands and information into the systems 10 and 100. The video monitor 40 provides medical treatment information 126 to the patient or operator.

Figure 3A:
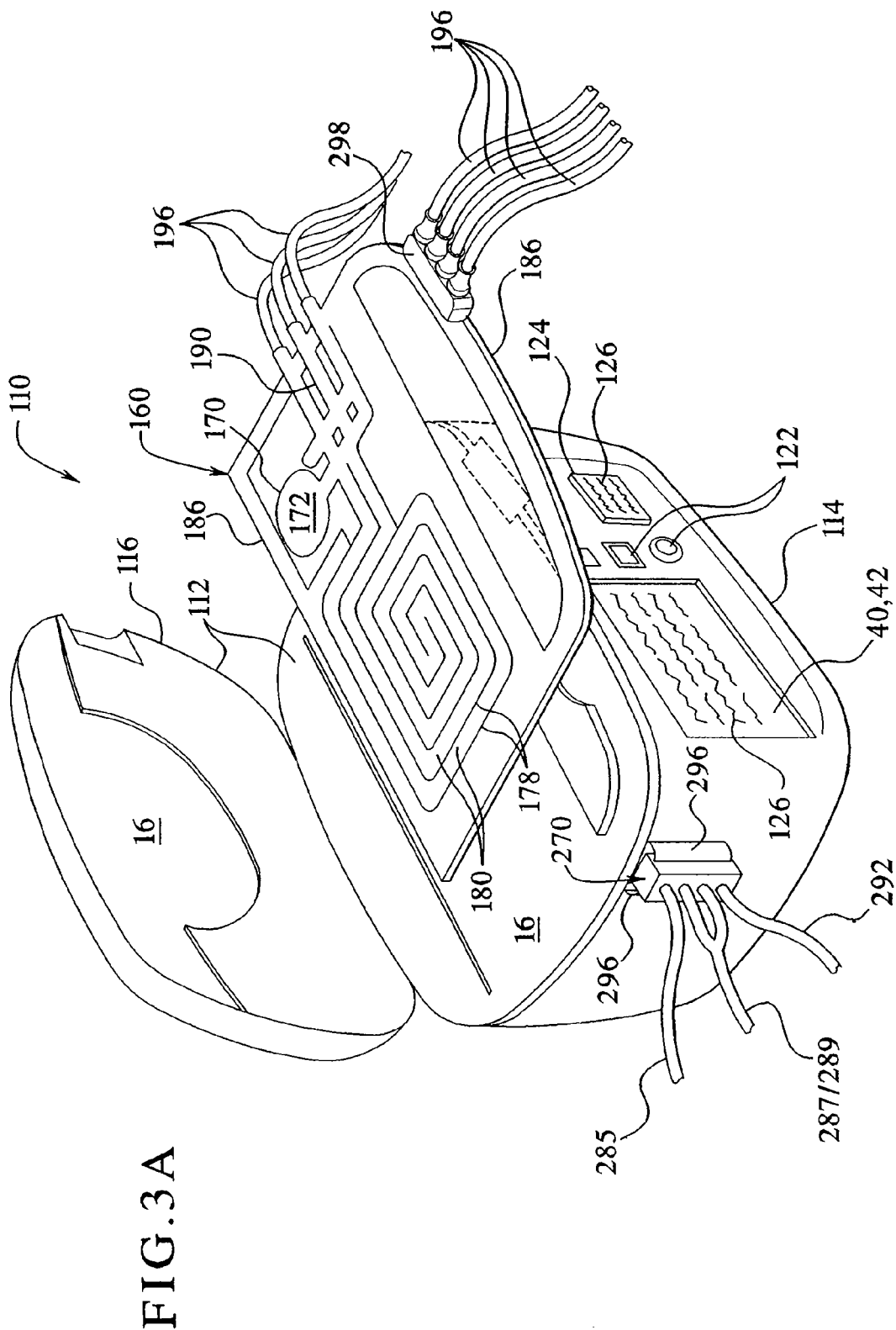
FIGS. 3A and 3B illustrate perspective views of the hardware unit and disposable unit of the present disclosure.
Figure 3B:
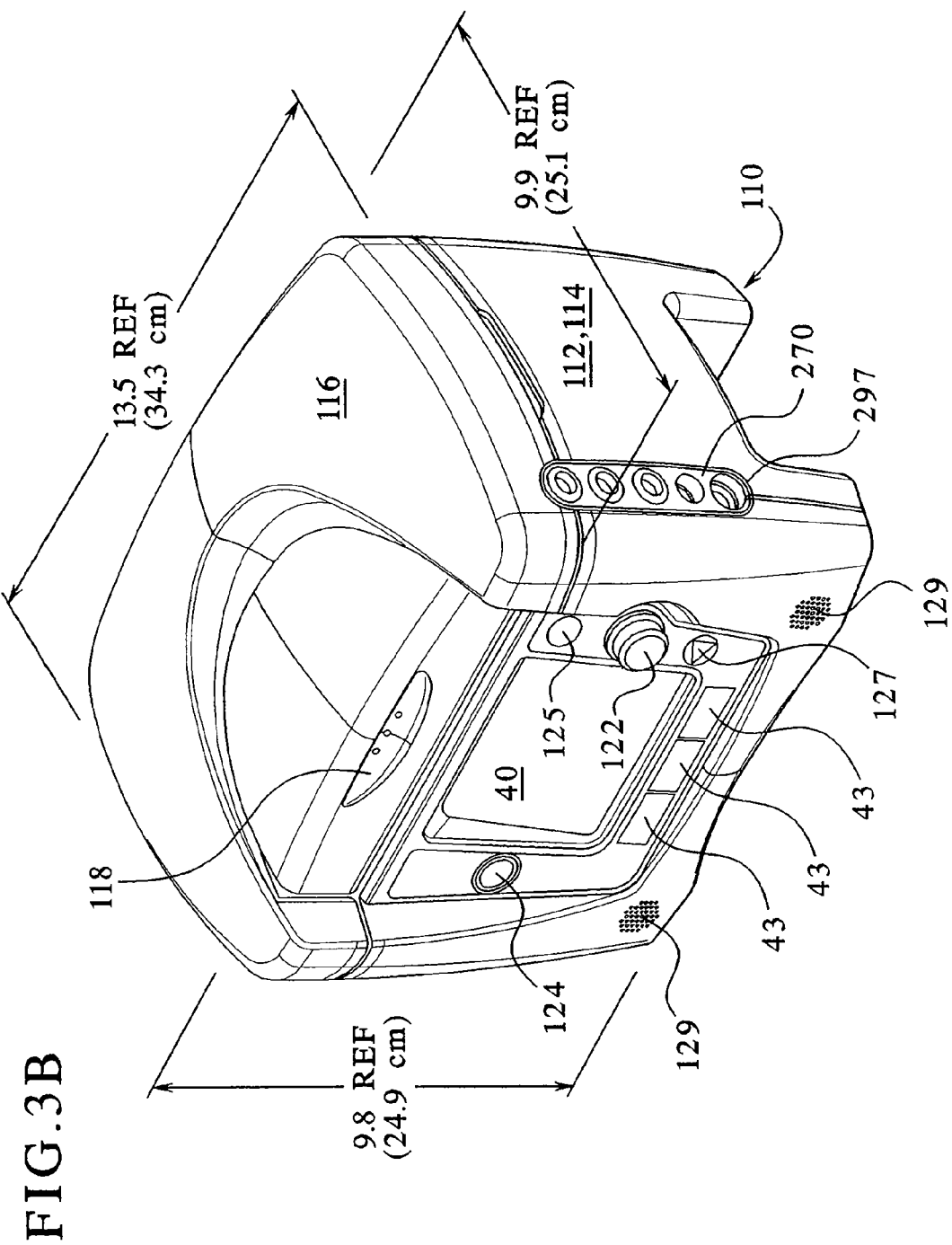

FIG. 3B illustrates one set of dimensions for the hardware unit 110 of the present disclosure. The size and weight of the present disclosure are less than previous automated dialysis system. This feature belies the portability and ease of use of the system 10, 100 of the present disclosure. The size and weight enable the hardware unit 110 to be shipped economically by standard overnight courier services. In the event that the system 10, 100 of the present disclosure breaks down, a replacement unit can be economically shipped to the patient in time for the next therapy.

The hardware unit 110 in an embodiment is approximately 23 to 30 cm high and deep and in one embodiment, as illustrated, about 25 cm high and deep. The hardware unit 110 in an embodiment is approximately 32 to 40 cm wide and in one embodiment, as illustrated, about 34 cm wide. The internal volume of the unit 110 is therefore about 17,000 $cm^3$ to about 36,000 $cm^3$, and in one embodiment, approximately 21,250 $cm^3$ (1310 $in^3$). Section view 4B aptly illustrates the many components maintained within this compact space and the efficient use of same. All these components and the hardware unit 110 have a total mass of about six to nine kilograms ("kg") and in one embodiment about seven kilograms.

FIGS. 3A to 4B also illustrate that the architecture, configuration and layout of the hardware unit 110 provides an automated system that is also convenient to use. The components of the system 10,100 with which the patient must interact are placed on the top, front and sides of the unit 110. The flow control components are placed below the heater 116, which is placed below the disposable unit loading station. The monitor 40 and controls 43, 122, 124, 125 and 127 are placed in the front of the unit 110.

Figure 4B:
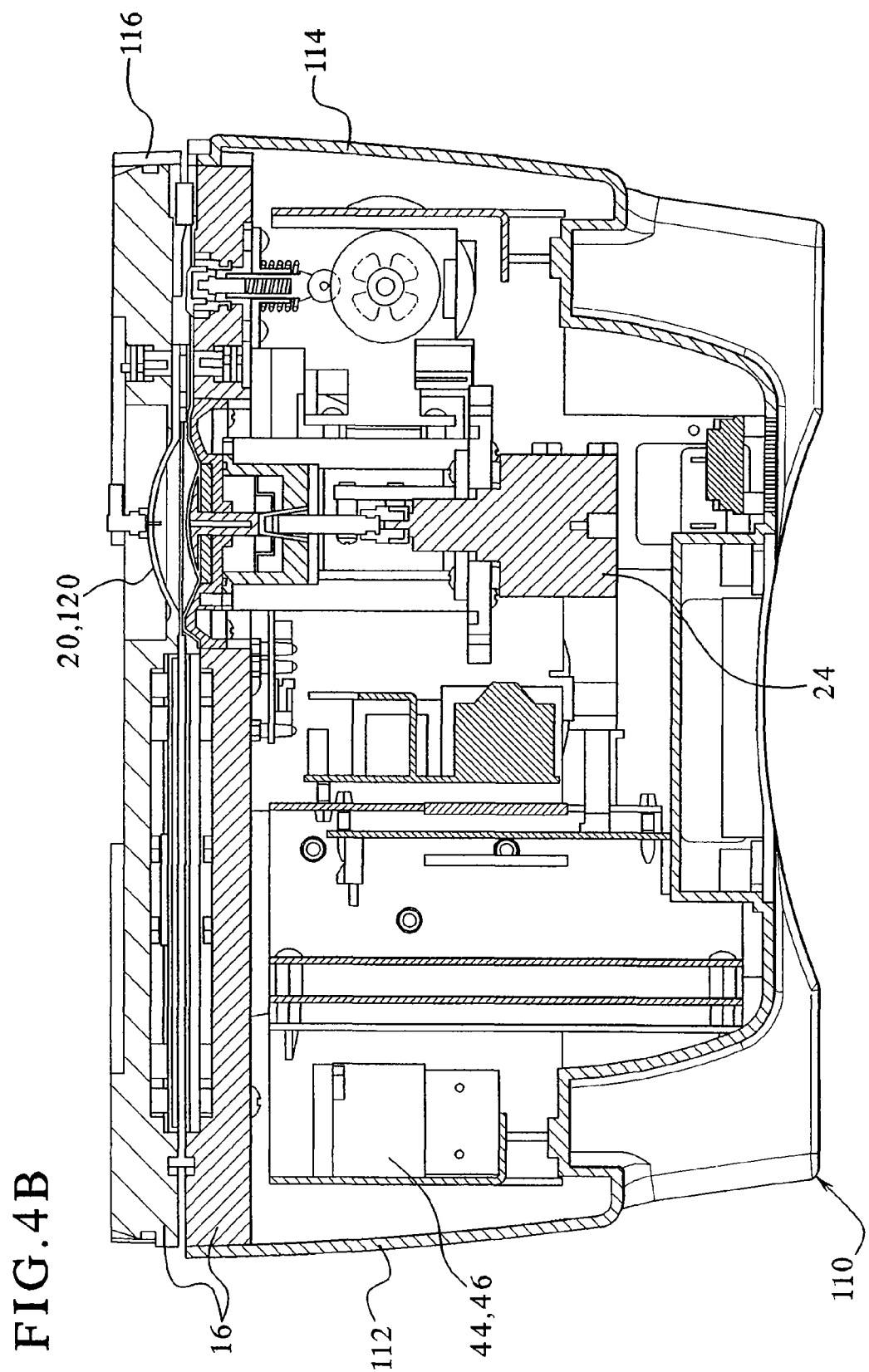
FIG. 4B is a cross-sectional view taken along line 4B-4B in FIG. 4A, which shows one possible configuration of the system components within the hardware unit.

The hardware unit 110 contains the pump 20 or 120 and the linear pump actuator 24 if system 10 is employed. The hardware unit 110 also contains the valve actuator 26 including the valve motor 28, the in-line heater 16, the various sensors, the vacuum source 44 including the air pump motor 46 and the controller 30 as well as the other hardware described above. FIG. 4B illustrates that one of the pump chamber walls of the pump 20 or 120 is disposed in the lid 116 of the housing. In FIG. 4B, the heater 16 is disposed in the base 114 of the housing 112. Alternatively or additionally, the heater may be placed in the lid 116. The base 114 also contains the opposing pump chamber wall.

Referring now to FIGS. 3A, 4A, 4B, 5 and 6, various embodiments of the disposable unit 160 are illustrated. In each of the embodiments, the disposable unit 160 includes a pair of flexible membranes, including an upper flexible membrane 162 and a lower flexible membrane 164. The disposable unit 160 of FIG. 6 includes two pairs of flexible membranes, namely, membrane pair 166 and membrane pair 168. Each of the membrane pairs 166 and 168 also includes the upper flexible membrane 162 and the lower flexible membrane 164.

The flexible membranes 162 and 164 can be made of any suitable sterile and inert material, such as a sterile and inert plastic or rubber. For example, the membranes 162 and 164 can be buna-N, butyl, hypalon, kel-F, kynar, neoprene, nylon, polyethylene, polystyrene, polypropylene, polyvinyl chloride, silicone, vinyl, viton or any combination of these. One material for the flexible membrane is described below in connection with FIGS. 13 and 14.

Figure 5:
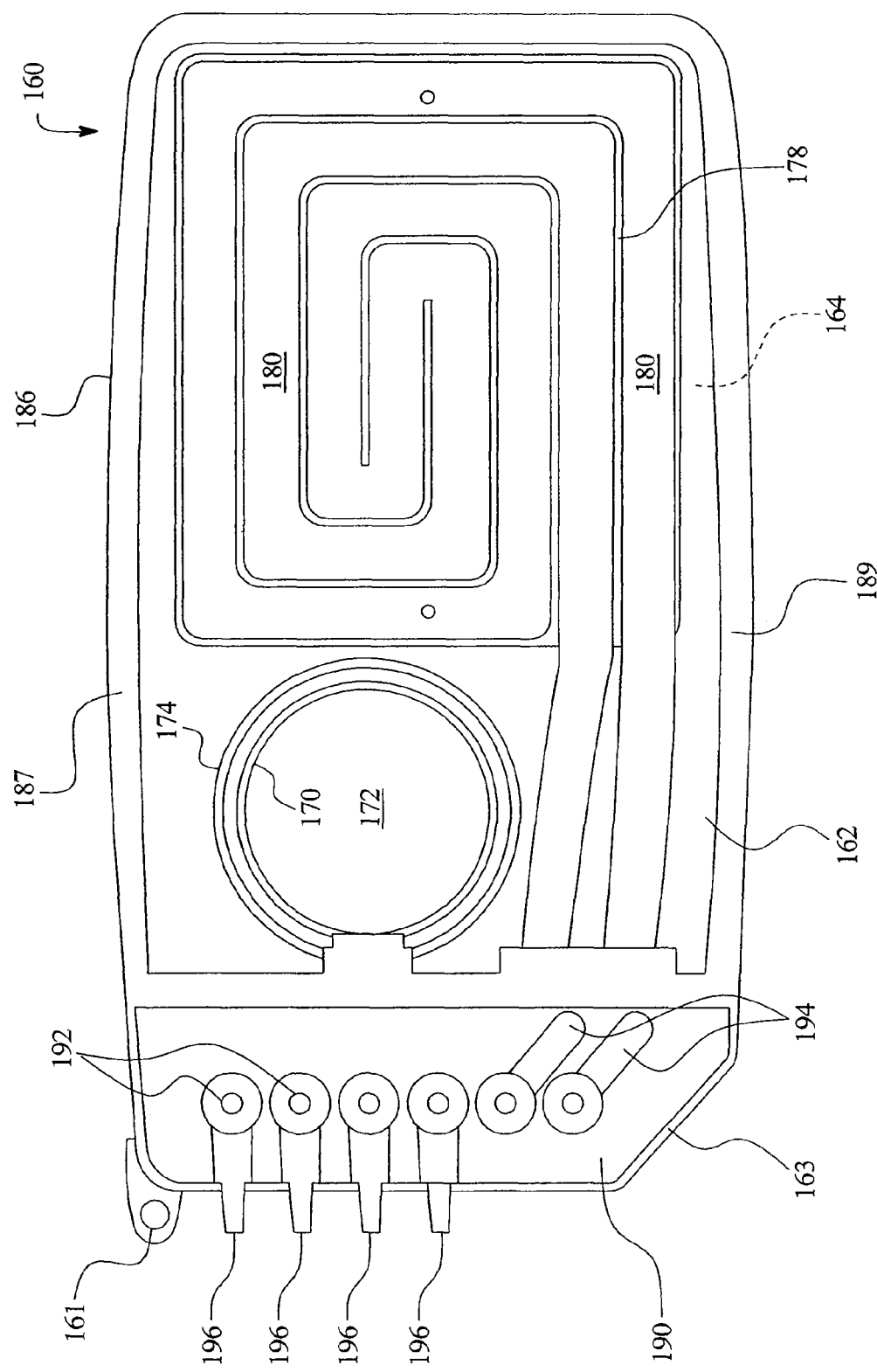
FIGS. 5 and 6 illustrate additional embodiments of the disposable unit of the present disclosure.

The membranes 162 and 164 are sealed together in various places to create fluid flow paths and receptacles between the membranes 162 and 164. The seals are heat seals, adhesive seals or a combination of both. FIGS. 3A, 4A, 5 and 6 illustrate that a generally circular seal 170 creates a substantially circular fluid pump receptacle 172 between the membranes 162 and 164. The pump receptacle 172 operates with the fluid pumps. Instead of the seal 170, one alternative embodiment is for the base 114 and lid 116 to press the membranes together to form the seal. FIGS. 4A and 5 illustrate that in an embodiment, the disposable unit 160 provides a secondary seal 174 to protect the systems 10 and 100 in case the primary seal 170 leaks or degrades during use.

FIGS. 3A, 4A and 4B illustrate that the fluid pump receptacle 172 fits between the clamshell shapes of the pumps 20 and 120 in the lid 116. The clamshell shapes defined by the base 114 and lid 116 of the hardware unit 110 together with the fluid pump receptacle 172 form the pump chamber of the pumps 20 and 120 of the present disclosure. The clamshell shapes in the base 114 and lid 116 include one or more ports with which to draw a vacuum on the membranes 162 and 164. In this manner, the membranes 162 and 164 are pulled towards and conform to the clamshell shapes in the base 114 and lid 116 and thereby create a negative pressure inside the receptacle 172 that pulls medical fluid from a supply bag 14 located outside the hardware unit 110, into the receptacle 172.

FIGS. 3A, 4A, 5 and 6 illustrate that a generally rectangular, spiral seal 178 creates a spiral heating path 180 between the membranes 162 and 164. The fluid heating path 180 runs from a valve manifold 190, through the spiral section, and back to the valve manifold 190. FIG. 4A illustrates that the fluid heating path 180 fits between the heating plates of the heater 16, which reside in the base 114 and lid 116 of the hardware unit 110. Providing a heat source on either side of the fluid heating path 180 enables the medical fluid to be quickly and efficiently heated. In alternative embodiments, however, the heater 16 can include only a single heater on one side of the fluid heating path 180 defined by the disposable unit 160 or multiple heaters on each side of the disposable unit 160.

The upper and lower membranes 162, 164 are attached to the disposable unit 160 utilizing heat sealing techniques as described herein. The membranes 162 and 164 are expandable so that when the disposable unit 160 is placed between a predefined gap between the upper and lower plates of the heater 16, the membranes 162 and 164 expand and contact the heater plates. This causes conductive heating to take place between the plates of the heater 16 and the membranes 162, 164 and between the membranes and the medical fluid. The predefined gap is slightly larger than the thickness of the disposable unit 160. Specifically, when dialysate moves through the fluid heating path 180 of the disposable unit 160, the membranes 162, 164 of the spiral wound fluid heating pathway 180 expand between the spiral seal 178 and touch the plates of the heater 16.

A. Separate Sets of Membranes

Figure 6:
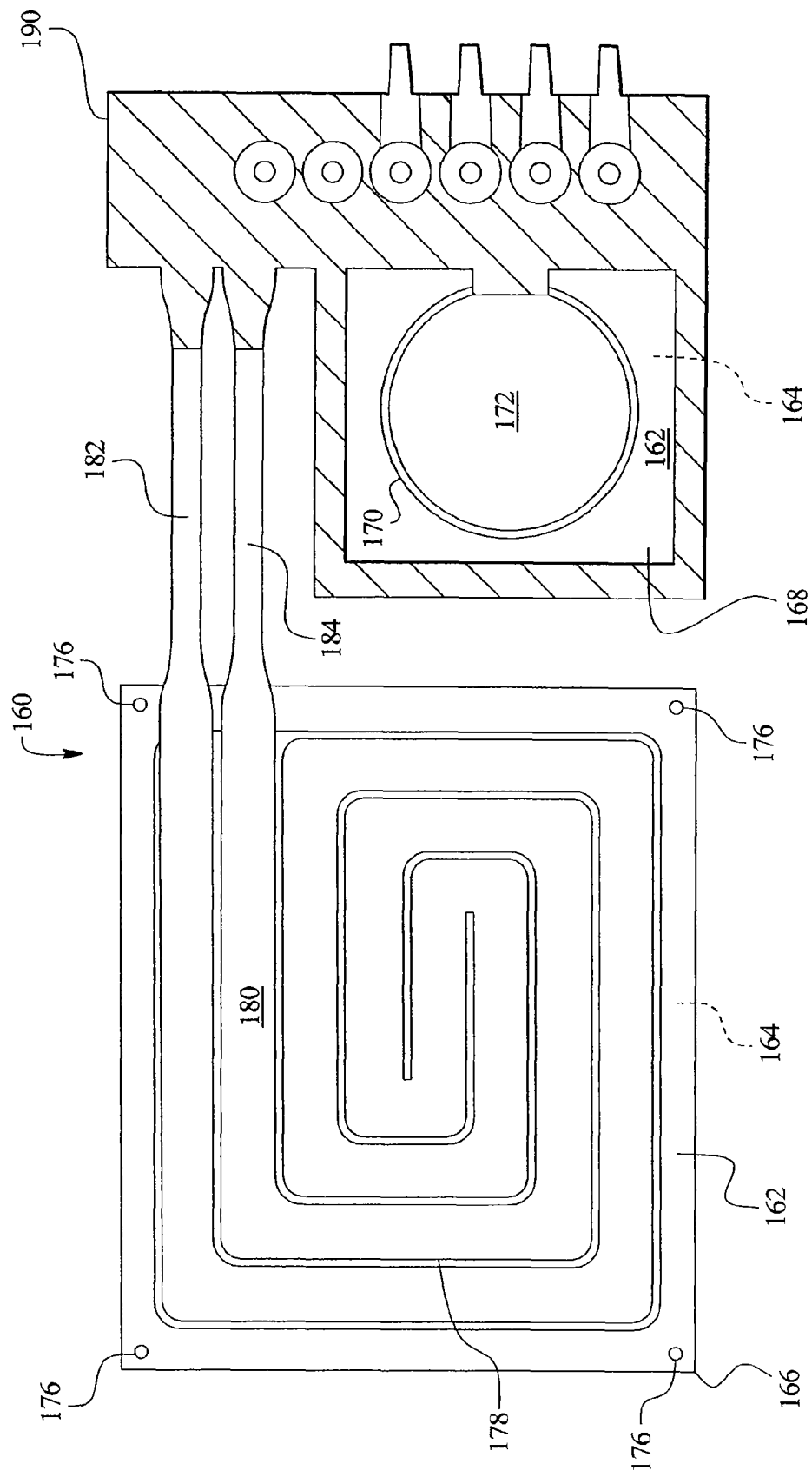

The disposable unit 160 of FIG. 6 is similar to the disposable units 160 of FIGS. 3A through 5. The in-line fluid heating path 180, however, is placed in a separate membrane pair 166 from the fluid pump receptacle 172 and the valve manifold 190, which are placed in a separate membrane pair 168. A pair of flexible tubes 182 and 184, which can be any suitable medical grade tubing, fluidly connect the valve manifold 190 to the fluid heating path 180. The tubes 182 and 184 can be connected to the membrane pairs 166, 168 by any desired means, such as, heat sealing, bonding, press-fitting or by any other permanent or removable fluid connection. When placed in the hardware unit 110, the heater 16 heats each side of the heater membrane pair 166, as in the other embodiments.

Separating the fluid heating path 180 from the fluid pump receptacle 172 and the valve manifold 190 enables the membranes of the respective pairs to be made of different materials. It is desirable that the membranes 162 and 164 of the heating pair 166 conduct or radiate heat efficiently. On the other hand, it is desirable that the membranes 162 and 164 of the fluid flow pair 166 withstand the forces of suction and mechanical actuation. It may therefore be desirable to use dissimilar materials for the membrane pair 166 and the membrane pair 168.

The membrane pair 166, defining the heater fluid flow path 180, additionally defines alignment holes 176 that align with pegs protruding from the base 114 or the lid 116 of the hardware unit 110. Each of the embodiments of the disposable unit 160 disclosed herein may be adapted to include alignment holes 176, which aid the patient or operator in properly placing the disposable unit 160 within the housing 112 of the hardware unit 110.

B. Rigid Frame and Bowed Sides

As shown in FIGS. 3A, 4A and 5, each of the embodiments of the disposable unit 160 disclosed herein may also be adapted to provide a rigid or semi-rigid member or frame 186, which in an embodiment, surrounds or substantially circumscribes the membranes 162 and 164 of the disposable unit 160. In an embodiment, the rigid member or frame 186 is made of a sterile, inert, rigid or semi-rigid plastic, for example, from one of or a combination of the plastics listed above for the membranes 162 and 164. The frame 186 aids the patient or operator in properly placing the disposable unit 160 within the housing 112 of the hardware unit 110.

In an embodiment, the housing 112 defines a pin or guide into which the frame 186 of the disposable unit 160 snugly fits. FIG. 5 illustrates that the frame 186 defines an aperture 161 that fits onto the pin or guide of the housing 112. The frame 186 can provide a plurality of apertures, such as the aperture 161, which fit onto a like number of pins or guides provided by the housing 112. FIG. 5 also illustrates that the frame 186 includes an asymmetrical member or chamfer 163. The chamfer 163 forms an angle, such as forty-five degrees, with respect to the other sides of the frame 186. The housing 112 defines or provides an area into which to place the disposable unit 160. The area has the asymmetrical shape of the frame 186 or otherwise provides guides that only allow the unit 160 to be placed in the housing 112 from a single direction. The chamfer 163 and the cooperating housing 112 ensure that when the patient places the disposable unit 160 in the housing 112, the bottom of the disposable unit 160 is placed in the housing 112 and the fluid inlets/outlets 196 face in the proper direction.

As discussed above, the disposable unit 160 includes a valve manifold 190. In an embodiment, the valve manifold 190 is made of a rigid or semi-rigid plastic, such as, from one of or a combination of the plastics listed above for the membranes 162 and 164. The valve manifold 190 is covered on either side by the upper and lower membranes 162 and 164 to thereby create a sealed and inert logic flow path for the systems 10 and 100.

In FIG. 5, the manifold 190 defines holes 192 and slots 194. The holes 192 define the location of the valves, for example, valves V1 to V5 of the system 10. The slots 194 define the fluid flow paths from the valves to the fluid pump receptacle 172, the fluid heating path 180 or to fluid inlets/outlets 196. The fluid inlets/outlets 196 individually lead to the supply bag 14, the catheter line 56, the patient 12 and the drain 18. The fluid inlets/outlets 196 may have various configurations and orientations, as contrasted by FIG. 3A. The drain 196 may also be adapted to connect to an external flexible tube via a method known to those of skill in the art.

In an embodiment, the rigid or semi-rigid frame 186 includes bowed sides 187 and 189, as illustrated in FIG. 5. The bowed sides 187 and 189 are formed with the frame 186 before the membranes 162 and 164 heat seal or adhesively seal to the frame 186 and manifold 190. The frame 186 and bowed sides 187 and 189 can be extruded plastic or plastic injection molded. The frame 186 can include as little as one bowed side, any number less than all, or have all sides be bowed.

In the illustrated embodiment, the sides 187 and 189 bow outward although they can alternatively bow inward. In an embodiment, the sides are bowed in a direction of the plane of the frame 186 of the disposable unit 160. The bowed sides 187 and 189 increase the rigidity of the frame 186 and the disposable unit 160. The disposable unit is accordingly more easily placed in the housing 112 of the hardware unit 110. The bowed sides 187 and 189 reduce the amount of flexing or distortion of the frame 186 due to heat sealing or mechanically pressing membranes 162 and 164 onto the frame 186 and manifold 190.

C. Heat Seal Interface

Figure 7:
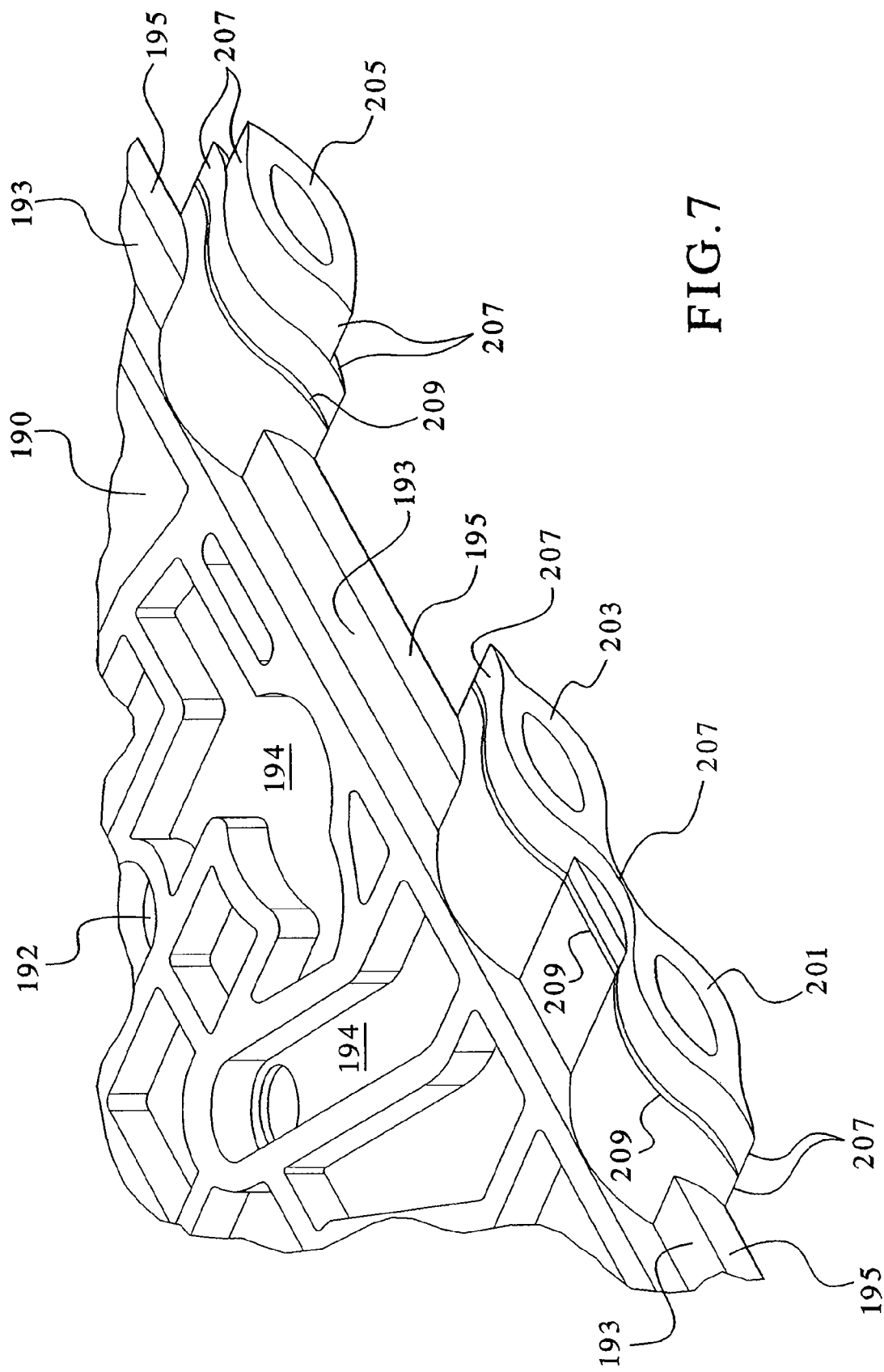
FIG. 7 is a perspective view of one embodiment of a valve manifold that includes a reduced thickness interface for sealing to membranes of a disposable dialysis unit.

Referring now to FIG. 7, an embodiment for heat sealing the membranes 162 and 164 to the manifold 190 is illustrated. In an embodiment, the manifold 190 is made of a rigid or semi-rigid plastic material as described above. Heat sealing the membranes 162 and 164 to the semi-rigid manifold 190, which in an embodiment is an injection molded component, requires different processing parameters than heat sealing the individual membranes 162 and 164 together, for example, at seal 170 of the fluid pump receptacle 172. In particular, heat sealing the membranes 162 and 164 to the manifold 190 can require more heat, more pressure and more heating time. The semi-rigid or rigid manifold 190 is appreciably thicker than the individual membranes 162 and 164. Consequently, relative to the thin membranes, the thicker manifold 190 acts as a heat sink. The bond between the thin membrane and thicker manifold 190 therefore requires more heat or energy than the heat seal bond between the thin membranes 162 and 164.

As illustrated in FIGS. 3A, 4A, 5 and 6, the disposable unit 160 requires both membrane to manifold and membrane to membrane seals. It is desirable to heat seal the entire disposable unit 160 in one step or process for obvious reasons. It should also be obvious that the heat sealing process should be performed so as avoid burning or melting one of the thin membranes 162 or 164.

FIG. 7 illustrates one embodiment for solving the heat sinking disparity between varying materials. FIG. 7 illustrates a portion of the manifold 190, which is shown in its entirety in FIG. 5. In FIG. 5, the manifold 190 illustrates a port that connects to the fluid pump receptacle 172. This port is illustrated as port 205 in FIG. 7. FIG. 5 also illustrates two ports extending from the manifold 190 that fluidly connect to the fluid heating path 180. These ports are illustrated as ports 201 and 203 in FIG. 7. Both FIG. 5 and FIG. 7 illustrate that the injection molded manifold 190 defines a plurality of holes 192 and slots 194. The holes 192 operate with the valve actuator and the slots 194 to form fluid pathways when enclosed by the membranes 162 and 164.

To reduce the amount of heat necessary to seal the membranes 162 and 164 to the manifold 190, the manifold 190 includes a side 193 having a lesser thickness than the remaining portion of the manifold 190. The thinner side 193 has less mass and therefore absorbs less localized heat than would a manifold of constant thickness. The side 193 also defines or includes a tapered portion 195. The tapered portion 195 provides flat surfaces on which to seal the membranes 162 and 164 and also positions the membranes 162 and 164 together so that in an embodiment a membrane to membrane seal may also be made in addition to the membrane to manifold 190 seal.

The tapered edges 195 form an interface for the membranes 162 and 164 to seal to the manifold 190, which occurs along continuous stretches of the sides 193 of the manifold 190 that require sealing or that would otherwise come into contact with the medical fluid. Therefore, as illustrated in FIG. 5, the side of the manifold 190 defining the input/output ports 196 does not need to be tapered as illustrated in FIG. 7. Also, as illustrated in FIG. 7, the tapered edges 195 of the thin sides 193 discontinue where the ports 201, 203, and 205 extend from the manifold 190.

The ports 201, 203 and 205 also form tapered edges 207. Tapered edges 207 form an interface for heat sealing the parts to the membranes 162 and 164. As described above, the tapered edges 207 of the ports 201, 203 and 205 also enable a membrane to membrane seal to take place directly next to the membrane to tapered edge 207 seal. The tapered edges 195 and 207 in an embodiment gradually taper towards the knife-like edge. In other embodiments, the tapered edges 195 and 207 may take on different forms or shapes, such as a rounded edge, a blunter edge or may simply be further reduced in thickness from side 193 of the manifold 190. As illustrated, the ports 201, 203 and 205 in an embodiment form ovular openings. The tapered ovular openings provide a smoother transition angle than would a circular outer diameter. The ovular openings perform as well as round openings from a fluid flow standpoint as long as open area of the inner oval is not less than the open area of a suitable circular port.

The ports 201, 203 and 205 also form raised portions 209. The raised portions 209 form a bead of polymeric material along the tops of the ports 201, 203 and 205 and the tapered edges 207. The beads can be additionally or alternatively placed along the tapered edges 195 and or the sides 193. The raised portions or beads 209 provide an extra thin area of plastic that melts or deforms to provide a flux-like sealant that enables the membranes 162 and 164 to seal to the manifold 190. The beads create a concentrated strip of higher temperature plastic than the surrounding plastic of the manifold 190. The membranes 162 and 164 seal to the manifold 190 without having to heat a larger area of the manifold 190. The raised portions or beads 209 help to seal curved portions and corners created by the manifold 190.

D. One-Piece Tip Protector Organizer and Vented Tip Protector

Figure 8:
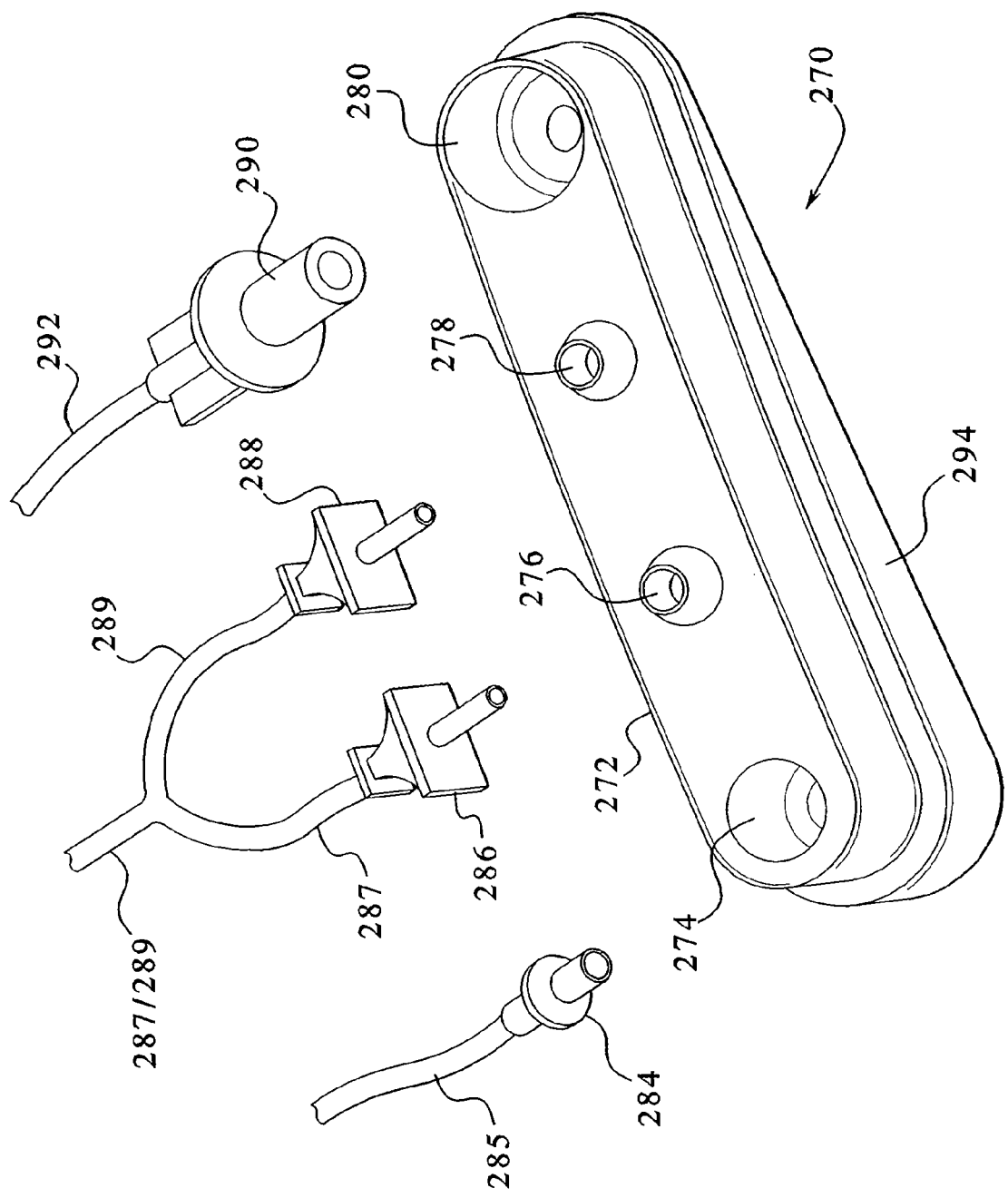
FIG. 8 is a perspective view of one embodiment of a multiple tip protector organizer of the present disclosure.

Referring now to FIG. 8, one embodiment of a one-piece tip protector organizer 270 is illustrated. In the HOMECHOICE® peritoneal dialysis system provided by the assignee of the present disclosure, a disposable set is prepackaged and provided to the patient. The patient opens up the package, wherein each of the components is sterilized and maintained within the disposable set. The disposable set includes a disposable unit and a number of tubes emanating from the disposable unit. Like the present disclosure, the HOMECHOICE® disposable unit includes a drain line tube that connects to one or more fill bag tubes, and a tube that connects to a patient transfer set. Each of these tubes requires a separate tip protector. That is, after sterilizing the inside of the disposable unit and the tubes, for example, using ethylene oxide, the ends of the tubes have to be capped off so that the sterilization of the inside of the system is maintained. The HOMECHOICE® system provides a separate tip protector for each tube.

The one-piece tip protector organizer 270 of the present disclosure provides a single body 272 (which may actually be made of a plurality of pieces) that defines or provides a plurality of tip protectors 274, 276, 278 and 280. The vented tip protector 270 not only houses and protects the connectors at the ends of the tubes emanating from the disposable unit 160, the one-piece tip protector 270 also organizes and orders the tubes according to the steps of the dialysis therapy. In the illustrated embodiment, the tip protector 274 is a tip protector for a drain line connector 284 connected to a drain line 285 that leads to the appropriate port of the disposable unit 160. The tip protectors 276 and 278 are supply bag protectors that protect the connectors 286 and 288 that connect to the ends of the tubes 287 and 289 that run to a "Y" connection 287/289, wherein the leg of the "Y" connection 287/289 runs to the appropriate port of the disposable unit 160. The tip protector 280 is a patient fluid line protector. The tip protector 280 houses and protects a connector 290 that connects to patient tube 292, which runs to the appropriate port of the disposable unit 160.

Each of the tubes 285, the "Y" connection 287 and 289 and the patient fluid tube 292 in an embodiment are made of polyvinylchloride ("PVC") having an inner diameter of 4 mm and an outer diameter of 5 mm. As illustrated, the one-piece tip protector organizer 270 is adaptable to receive and protect various types of fluid connectors. The fluid connector 284 that runs via tube 285 to the drain line port of the disposable unit 160 is in an embodiment largely the same as the port that emanates from the supply bags 14. The ports that emanate from the supply bags 14 also include a membrane that is pierced by the sharp stem of the supply bag connectors 286 and 288. The drain line connector 284 does not include the membrane of the supply bag 14 as it is not needed. The tip protector 290 that connects to the end of the patient fluid tube 292 is discussed in detail below.

In one embodiment, the system 10, 100 of the present disclosure provides two, six liter supply bags 14. The two, six liter bags provide an economic amount of peritoneal dialysis fluid, which is enough fluid to provide a number of fill, dwell and drain cycles during the evening while the patient sleeps. The one-piece organizer 270 therefore provides two tip protectors 276 and 278, which house and protect the supply connectors 286 and 288. In alternative embodiments, the one-piece organizer 270 can define or provide any number of supply bag tip protectors. Any number of supply bags can be additionally linked via "Y" or "T" type tubing links.

The one-piece organizer 270 can provide additional tip protectors such as a last bag protector, which protects a line that runs to a bag that holds enough peritoneal fluid, e.g., two liters, for a final fill for the patient during the daytime. In this case, an additional last bag tube, not illustrated, would connect to a connector, which would be a bag piercing connector, the same as or similar to the fill bag connectors 286 and 288.

The body 272 of the tip protector organizer 270 is in an embodiment also made of PVC. The tip protectors 274, 276, 278 and 280 are injection molded or blow molded. Alternatively, the tip protectors can be separately applied to the body 272. As seen in FIG. 8, one or more of the tip protectors can include flutes, threads or other protrusions that aid in grasping and holding the respective tube connector. Further, while the organizer 270 is generally referred to herein as a "one-piece" organizer, the organizer 270 may itself be comprised of any number or pieces. "One-piece" refers to the feature that a single unit houses a multitude or tip protectors.

Figure 9:
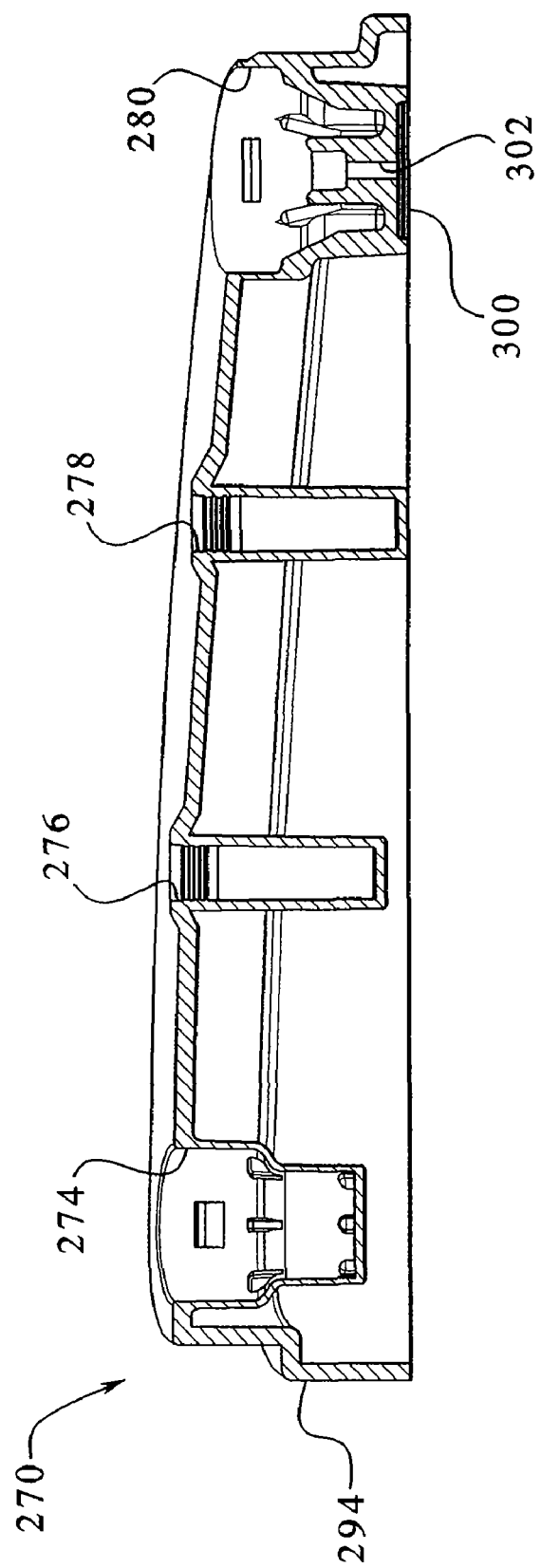
FIG. 9 is an elevation sectional view of the multiple tip protector organizer illustrated in FIG. 8.

The one-piece organizer 270 also includes a rim 294 that extends outwardly from the main portion of the body 272, and which circumvents the main portion of the body 272. Referring now to FIG. 9, a cross section of the one-piece organizer 270 illustrates that the rim 294 tapers downwardly from the drain line tip protector 274 towards the patient fluid tip protector 280. That is, the rim 294 is higher or thicker at the drain line end than it is at the patient fluid line end. This enables the one-piece tip protector organizer 270 to be mounted to the hardware unit 110 in only one orientation.

FIG. 3A illustrates that the one-piece tip protector organizer 270 in an embodiment slides into the hardware unit 110 vertically. The hardware unit 110 includes or provides a pair of members 296 that extend outwardly from a side wall of the hardware unit 110. FIGS. 3B and 4A illustrate another embodiment, wherein the rim 294 of the organizer 270 slides vertically into a notch 297 defined or provided by the base 114 of the housing 112 of the hardware unit 110. The rim 294 of the organizer 270 slides between the members 296 and the side wall of the hardware unit 110. The members 296 extend further outwardly as they extend running towards the top of the hardware unit 110. The taper of the members 296 corresponds to the taper of the rim 294 of the organizer 270 so that the organizer 270 can only slide into the hardware unit 110 vertically from one direction.

FIG. 9 also illustrates that the tip protectors 274, 276, 278 and 280 can have various cross-sectional shapes. Each of the tip protectors includes a solid bottom and sides that seal around the respective connectors 284, 286, 288 and 290, so that the one-piece organizer 270 maintains the sterility of the system even after the patient removes the disposable set from a sealed sterilized container. The one-piece organizer 270 illustrated in FIGS. 8 and 9 mounts in a sturdy fashion to the side of the hardware unit 110. Via this solid connection, the patient is able to remove the tubes 285, 287, 289 and 292 using only one hand in many cases. The interface between the hardware unit 110 and the organizer 270 simplifies the procedure for the patient and provides a solid, sterile environment for the tubes and associated connectors until used.

FIG. 3A also illustrates another possible embodiment wherein an alternative one-piece organizer 298 is integral to or provided by the frame 186 of the disposable unit 160. Here, the tubes 196, indicated generally, are horizontally organized as opposed to the vertical arrangement of the tip protector 270 in the housing 112. The horizontal one-piece organizer 298 illustrates that the concept of protecting and organizing the tubes before use can be provided in a variety of places and orientations in the system 10.

In one embodiment, the tip protector and organizer 270 structures the tubes 285, 287, 289 and 292 in a downwardly vertical order, such that the first tube that the patient is supposed to pull when starting the dialysis therapy is provided on top, the next tubes that the patient is supposed to pull are provided in the middle and the final tube is provided lowest on the vertically oriented one-piece organizer 270. According to one protocol, the patient first removes the drain connector 284 from the tip protector 274 and runs the drain line 285 to a toilet, drain bag or other drain. The patient then removes the supply connectors 286 and 288 and punctures the supply bags 14 (FIGS. 1 and 2). At this point, dialysate can be pumped to the disposable unit 160 and throughout the system 10. The controller 30 of the system 10, 100 begins a priming cycle, which is discussed in more detail below.

Once priming is complete, system 10, 100 prompts the patient to remove the primed patient line 292 and connect same to the transfer set implanted into the patient. The transfer set (not illustrated) includes a catheter positioned into the patient's peritoneal cavity and a tube running to the catheter. The tube also includes a connector that couples to the connector 290. At this point, system 10, 100 can begin to either drain spent peritoneal fluid from the patient 12 to the drain 18 or pull new fluid from one or both of the supply bags 14 and fill the patient's peritoneal cavity 12.

Figure 10:
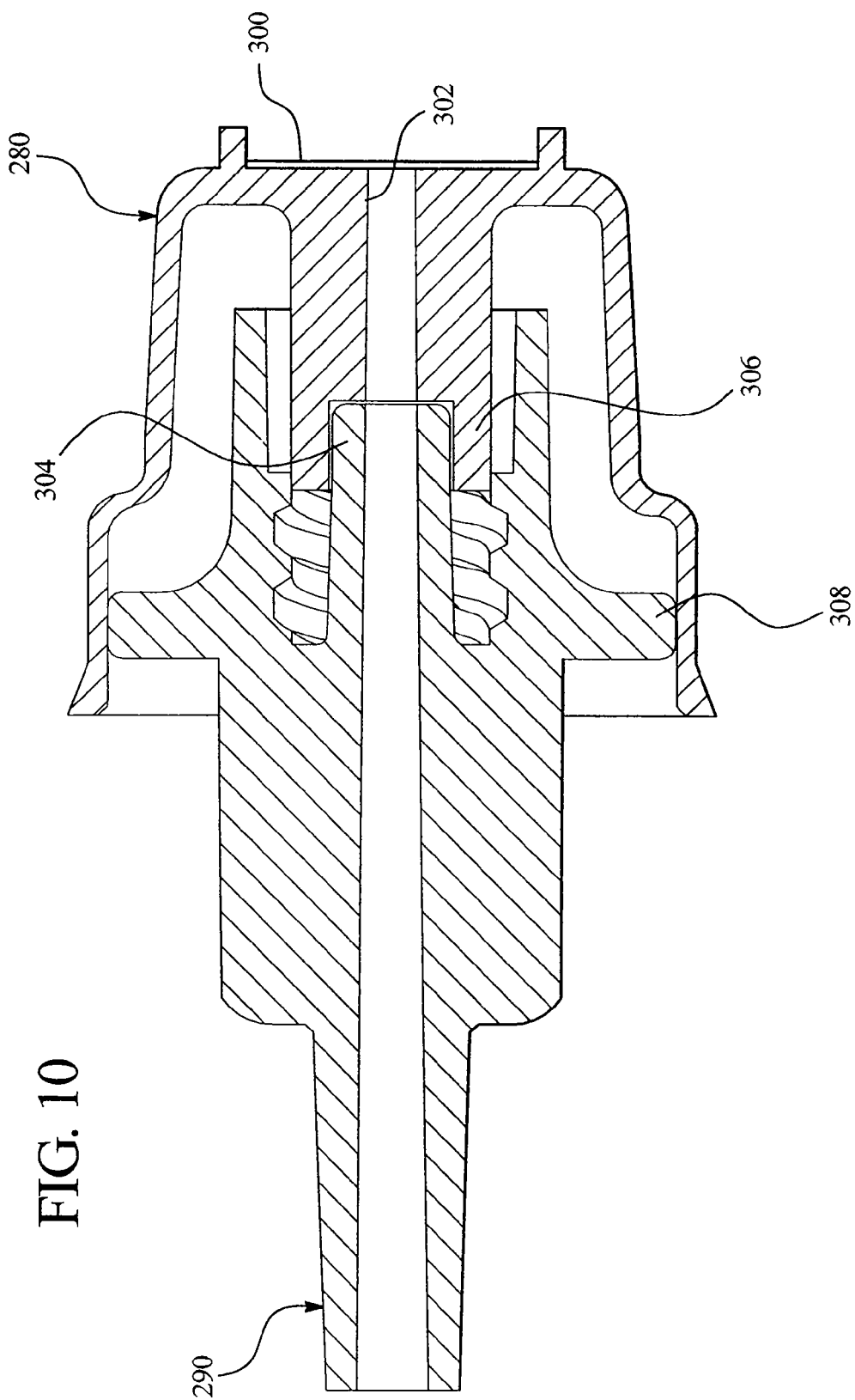
FIG. 10 is an elevation sectional view of one embodiment of a vented tip protector of the present disclosure showing the tip protector housing a patient fluid line connector.
Figure 11:
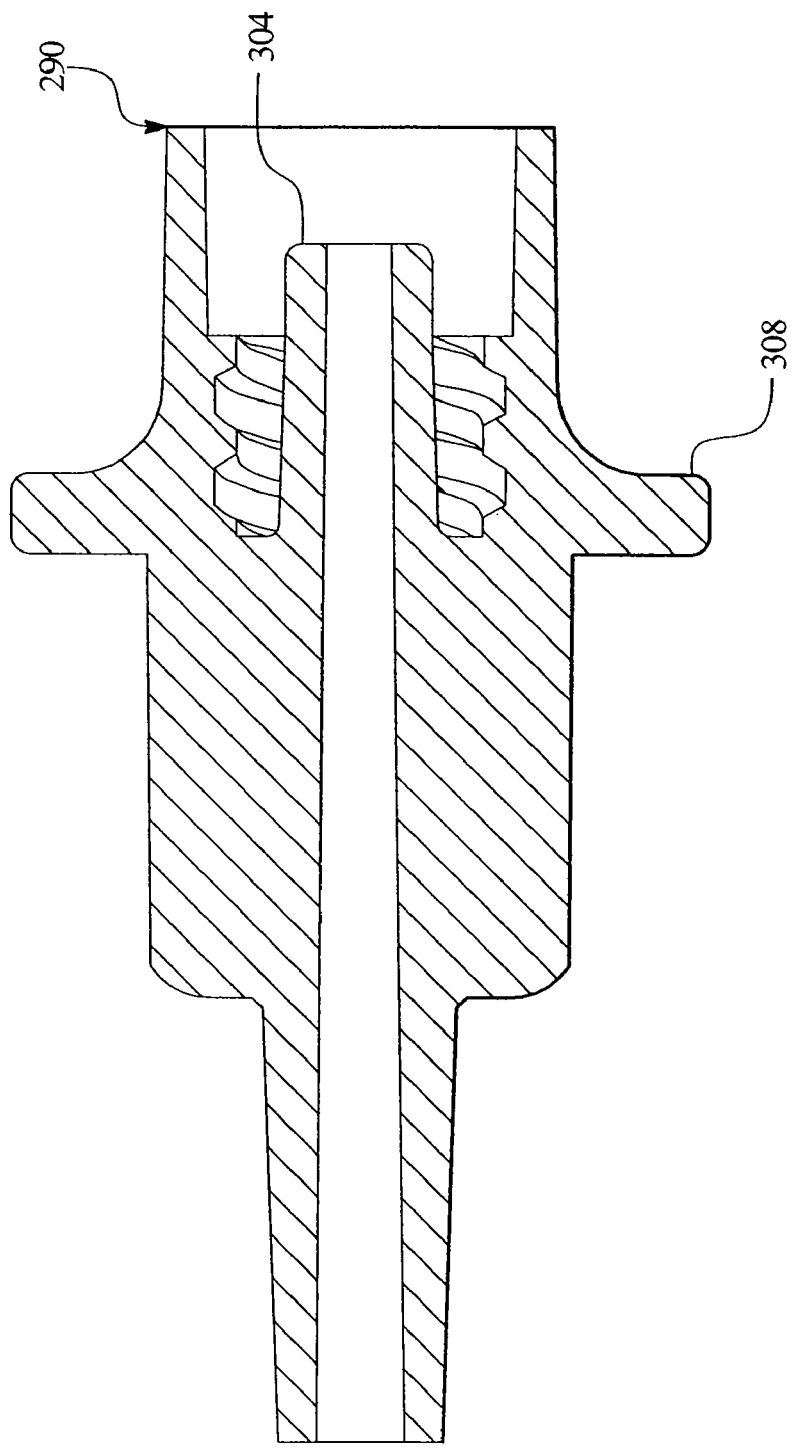
FIG. 11 is an elevation sectional view of one embodiment of the patient fluid line connector that couples to the vented tip protector of the present disclosure.
Figure 12:
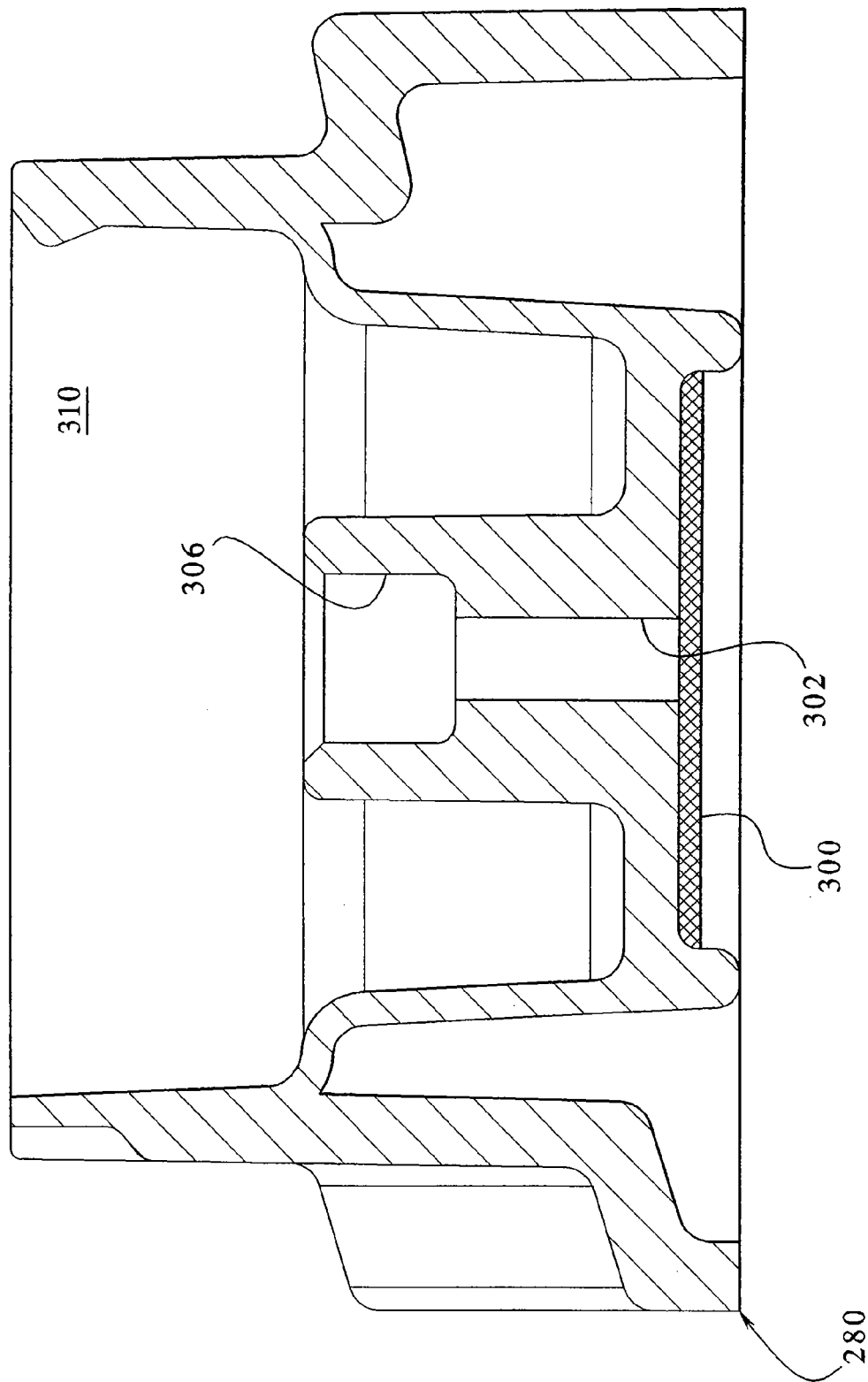
FIG. 12 is an elevation sectional view of one embodiment of the vented tip protector of the present disclosure.

Referring now to FIGS. 10 to 12, one embodiment for the patient line tip protector 280 of the present disclosure is illustrated. The HOMECHOICE® system produced by the assignee of the present disclosure primes the patient fluid line by allowing the patient connector to be held vertically approximately at the same level as the supply bag. In this manner, when the HOMECHOICE® system primes the disposable unit, gravity feeds peritoneal fluid into the patient fluid line up to the end of the patient fluid connector. The patient fluid connector is open so that air can freely escape when the peritoneal fluid is fed by gravity through the patient line. HOMECHOICE® system enables the patient fluid line to be primed without counting pump strokes or having to meter out a known volume of dialysate, techniques which are complicated and prone to failure.

The system 10, 100 of the present disclosure provides a different apparatus and method of priming without having to calculate the amount of fluid that is needed to just reach but not surpass the patient connector of the patient fluid line. FIG. 10 shows a cross-section of the patient fluid connector 290 that has been inserted into the vented tip protector 280. FIG. 11 illustrates a cross section of the patient fluid connector 290 only. FIG. 12 illustrates a cross section of the tip protector 280 only. A hydrophobic membrane 300 is placed on the outer edge of the tip protector 280. The tip protector 280 defines a fluid lumen 302 that runs through the entire length of the tip protector 280. The hydrophobic membrane 300 covers the fluid lumen 302. The hydrophobic membrane 300 allows air to purge from inside the patient's fluid line but does not allow water or peritoneal fluid to flow through same.

It should be appreciated that the vented tip protector 280 including the hydrophobic membrane 300 is not limited to being placed in the one-piece tip protector organizer 270. FIG. 9 illustrates that the one-piece organizer 270 does include the patient tip protector 280 having the hydrophobic membrane 300 and the fluid lumen 302. The vented tip protector 280 in an alternative embodiment, however, can be provided as a separate or stand alone tip protector, similar to the one used on the HOMECHOICE® system provided by the assignee of the present disclosure.

Hydrophobic membranes, such as the hydrophobic membrane 300 employed herein, are commercially available. One suitable hydrophobic membrane is produced by Millipore, 80 Ashby Road, Bedford, Mass. 01730. FIG. 12 best illustrates that the hydrophobic membrane heat seals or sonically seals to the tip protector 280. The fluid lumen 302 in an embodiment is relatively small in diameter, such as approximately fifty to seventy thousandths of an inch (1.25 to 1.75 mm).

The vented tip protector 280 and the patient fluid connector 290 also cooperate so that when the system 10, 100 is completely primed, the tip protector 280 and connector 290 minimize the amount of fluid that spills when the patient removes the patient fluid connector 290 from the tip protector 280. The connector 290 includes or provides a male lure 304 that mates with a female lure 306 best seen in FIG. 10. The mating lures 304 and 306 prevent peritoneal fluid from filling the cavity of the tip protector 280, which must be wide enough to house the flange 308 of the patient fluid connector 290. FIG. 12 illustrates that the seal interface between the male lure 304 of the connector 290 and the female lure 306 of the vented tip protector 280 reduces the volume significantly from an interior volume 310 existing around the male lure 304 to the fifty to seventy thousandths diameter of the lumen 302.

To prime the system 10, 100 the patient removes the drain line 285 from the tip protector 274 and places it into a tub, toilet or drain bag 18. The patient removes the two or more supply bag connectors 286 and 288 and punctures seal membranes (not illustrated) of the supply bags 14. System 10, 100 may then automatically begin pump priming or may begin pump priming upon a patient input. In either case, system 10, 100 pumps fluid from one or both of the supply bags 14 through the connectors 286 and 288 and tubes 287 and 289, into the disposal disposable unit 160, out the patient fluid line 292 and into the patient fluid connector 290, which is still housed in the vented tip protector 280 of the one-piece organizer 270. The organizer 270 is vertically housed in the hardware unit 110 as seen in FIGS. 3A and 3B.

When the peritoneal fluid reaches the patient fluid connector 290, most all the air within the system 10 has been pushed through the hydrophobic membrane 300 attached at the end of the tip protector 280 housed in the one-piece tip protector 270. The nature of the hydrophobic membrane 300 is that it allows air to pass through but filters or does not allow water or peritoneal fluid to pass through same. Thus, when the fluid finally reaches the hydrophobic membrane 300, the lack of any additional space in which to flow fluid causes the pressure to increase within the system 10, 100. The system 10, 100 provides one or more pressure sensors, for example pressure sensors 68 (marked as FP1, FP2 and FPT in FIGS. 1 and 2).

One or more of the pressure sensors 68 sense the increase in pressure due to the peritoneal fluid backing up against the hydrophobic filter 300. The pressure sensor(s) sends a signal to the I/O module 36 of the controller 30. The controller 30 receives the signal and is programmed in memory device 32 to shut down the diaphragm pump 20, 120. In this manner, the system 10 self-primes each of the fill lines 287 and 289, the disposable unit 160 and the patient fluid line 292 automatically and without need for controlled volume calculations or gravity feeding.

System 10, 100 also includes one or more safety features that may be based upon a volume calculation. That is, under normal operations, the system 10, 100 does not control the priming using a volume calculation. However, in the case where for example the patient removes the patient fluid connector 290 from the vented tip protector 280 of the one-piece tip organizer 270 before the system 10, 100 senses a pressure increase and stops the pumps 10, 100, the system 10, 100 can employ an alarm calculation, wherein the system 10, 100 knows that it has pumped too much peritoneal fluid (e.g., a predetermined amount more than the internal volume of the system) and shuts down pump 20, 120 accordingly.

III. Membrane Material for the Disposable Unit

Figure 13:
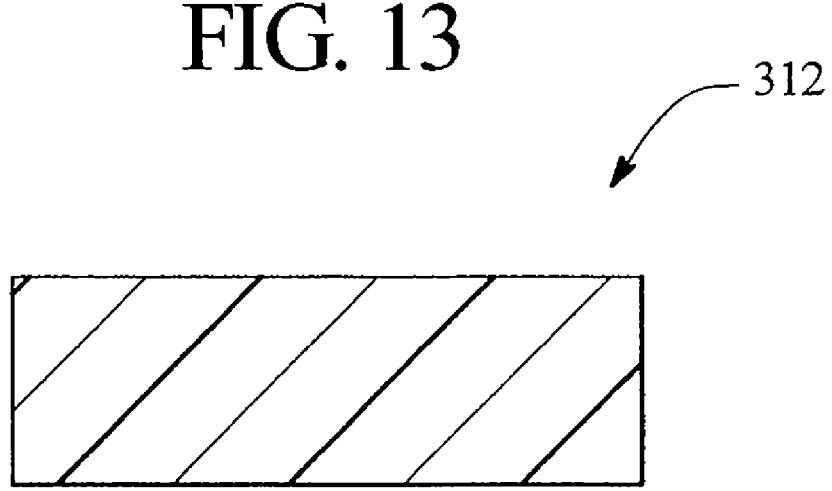
FIG. 13 is a sectional view of one embodiment of a single layer film structure for the disposable unit membranes of the present disclosure.
Figure 14:
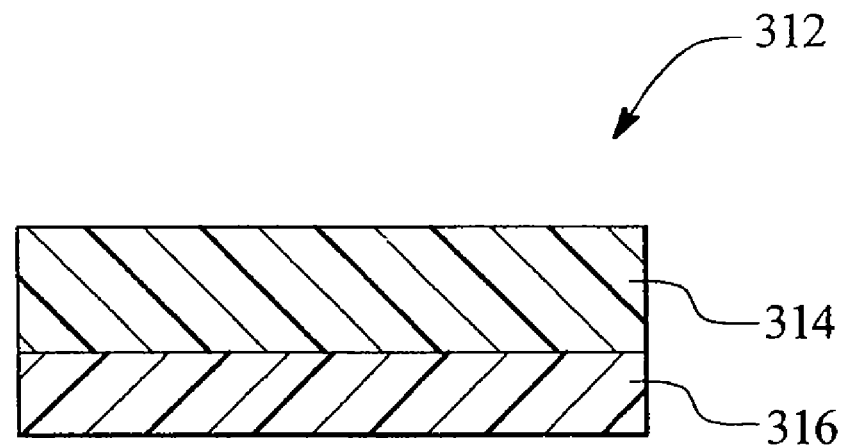
FIG. 14 is a sectional view of one embodiment of a multiple layer film structure for the disposable unit membranes of the present disclosure.

Referring now to FIGS. 13 and 14, upper and lower membranes 162, 164 can be fabricated from a monolayer film structure 312 (FIG. 13) or a multiple layer film structure 312 (FIG. 14). The film 312 is constructed from a non-PVC containing polymeric material and must satisfy numerous physical property requirements. The film 312 must have a low modulus of elasticity so that it can be deformed under low pressure to function as a pumping element. What is meant by low modulus is the film 312 has a modulus of elasticity when measured in accordance with ASTM D882, of less than about 10,000 psi, more preferably less than about 8,000 psi and even more preferably less than about 5,000 psi and finally, less than about 3,000 psi, or any range or combination of ranges defined by these numbers. The film 312 must have adequate thermal conductivity to allow for in-line heating. The film has a thermal conductivity of greater than 0.13 W/meters-° K when measured using a Hot Disk™ sold by Mathis Instruments Ltd. The film 312 must be capable of being heat sealed to cassette 160. The film 312 must be capable of being sterilized by exposure to gamma rays, by exposure to steam for a period of time (typically 1 hour), and exposure to ethylene oxide without significant degradation of the film or having an adverse effect on the dialysis solution. Finally, the film 312 must be capable of being extruded at high rates of speed of greater than 50 ft/min.

The monolayer structure 312 is formed from a blend of from about 90% to about 99% by weight of a first component containing a styrene and hydrocarbon copolymer and from about 10% to about 1% of a melt strength enhancing polymer and more preferably a high melt strength polypropylene.

The term "styrene" includes styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more specifically, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multiblock, and star block. Specific examples of diblock copolymers include styrene-butadiene, styrene-isoprene, and selectively hydrogenated derivatives thereof. Examples of tri-block polymers include styrene-butadiene-styrene, styrene-isoprene-styrene, alpha-methylstyrene-butadiene-alpha-methylstyrene, and alpha-methylstyrene-isoprene-alpha-methylstyrene and selectively hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a polystyrene-(ethylene/propylene)-polystyrene block polymer. When a polystyrene-polybutadiene-polystyrene block copolymer is hydrogenated, the resulting product resembles a regular copolymer block of ethylene and 1-butene (EB). This hydrogenated block copolymer is often referred to as SEBS. When the conjugated diene employed is isoprene, the resulting hydrogenated product resembles a regular copolymer block of ethylene and propylene (EP). This hydrogenated block copolymer is often referred to as SEPS. When the conjugated diene is a mixture of isoprene and butadiene the selectively hydrogenated product is referred to as SEEPS. Suitable SEBS, SEPS and SEEPS copolymers are sold by Shell Oil under the tradename KRATON, by Kurary under the tradename SEPTON® and HYBRAR®.

The block copolymers of the conjugated diene and the vinyl aromatic compound can be grafted with an alpha,beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc.

The first component containing a styrene and hydrocarbon block copolymer can be modified by adding an oil, such as a mineral oil, paraffinic oil, polybutene oil or the like. The amount of oil added to the styrene and hydrocarbon block copolymer is from about 5% to about 40%. The first component can also contain a polypropylene up to about 20% by weight of the first component. One particularly suitable first component is an oil modified SEBS sold by the Shell Chemical Company under the product designation KRATON G2705.

The melt strength enhancing polymer preferably is a high melt strength polypropylene. Suitable high melt strength polypropylenes can be a homopolymer or a copolymer of polypropylene and can have free end long chain branching or not. In one preferred form of the invention, the high melt strength polypropylene will have a melt flow index within the range of 10 grams/10 min. to 800 grams/10 min., more preferably 10 grams/10 min. to 200 grams/10 min, or any range or combination of ranges therein. High melt strength polypropylenes are known to have free-end long chain branches of propylene units. Methods of preparing polypropylenes which exhibit a high melt strength characteristic have been described in U.S. Pat. Nos. 4,916,198; 5,047,485; and 5,605, 936, which are incorporated herein by reference and made a part hereof. One such method includes irradiating a linear propylene polymer in an environment in which the active oxygen concentration is about 15% by volume with high energy ionization radiation at a dose of $1 \times 10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This further results in the desired free-end long chain branched, high molecular weight, non-linear, propylene polymer material. Radiation is maintained until a significant amount of long chain branches form. The material is then treated to deactivate substantially all the free radicals present in the irradiated material.

High melt strength polypropylenes can also be obtained as described in U.S. Pat. No. 5,416,169, which is incorporated in its entirety herein by reference and made a part hereof, when a specified organic peroxide (di-2-ethylhexyl peroxydicarbonate) is reacted with a polypropylene under specified conditions, followed by melt-kneading. Such polypropylenes are linear, crystalline polypropylenes having a branching coefficient of substantially 1, and, therefore, has no free end long-chain branching and will have a intrinsic viscosity of from about 2.5 dl/g to 10 dl/g.

Suitable copolymers of propylene are obtained by polymerizing a propylene monomer with an α-olefin having from 2 to 20 carbons. In a more preferred form of the invention the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers. In a preferred form of the invention, the propylene copolymer is obtained using a single-site catalyst.

The components of the blend can be blended and extruded using standard techniques well known in the art. The film 312 will have a thickness of from about 3 mils to about 12 mils, more preferably from 5 mils to about 9 mils.

FIG. 14 shows a multiple layer film having a first layer 314 and a second layer 316. FIG. 14 shows the use of two layers but the present disclosure contemplates using more than two layers provided the above-mentioned material property requirements are met. The first layer 314 can be of the same polymer blend used to fabricate the monolayer structure and in a more preferred form of the invention will define a seal layer for joining the film the cassette 160. The second layer 316 can be made from non-PVC containing materials and preferably is selected from polyolefins, polybutadienes, polyesters, polyester ethers, polyester elastomers, polyamides and the like and blends of the same. A tie layer or tie layers (not shown) may be required to adhere additional layers to the first layer 314.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In one preferred form of the invention the homopolymer of polypropylene is obtained using a single site catalyst.

It is also possible to use a blend of polypropylene and α-olefin copolymers wherein the propylene copolymers can vary by the number of carbons in the α-olefin. For example, the present disclosure contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present disclosure contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure.

It may also be desirable to use a high melt strength polypropylene as defined above.

Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3-10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE® and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 5% to about 40% by weight of the copolymer. The term "lower alkyl acrylates" refers to comonomers having the formula set forth in Diagram 1:

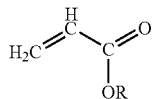

Diagram 1

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

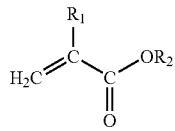

Diagram 2

$R_1$ and $R_2$ are alkyls having 1-17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention the polymer is a 1,2-addition product of 1,3 butadiene (these shall be referred to as 1,2 polybutadienes). In an even more preferred form of the invention the polymer of interest is a syndiotactic 1,2-polybutadiene and even more preferably a low crystallinity, syndiotactic 1,2 polybutadiene. In a preferred form of the invention the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di-or polycarboxylic acids and di or poly hydroxy alcohols or alkylene oxides. In a preferred form of the invention the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL. Suitable polyesters further include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL®.

Suitable polyamides include those that result from a ring-opening reaction of lactams having from 4-12 carbons. This group of polyamides therefore includes nylon 6, nylon 10 and nylon 12. Acceptable polyamides also include aliphatic polyamides resulting from the condensation reaction of di-amines having a carbon number within a range of 2-13, aliphatic polyamides resulting from a condensation reaction of di-acids having a carbon number within a range of 2-13, polyamides resulting from the condensation reaction of dimer fatty acids, and amide containing copolymers. Thus, suitable aliphatic polyamides include, for example, nylon 66, nylon 6,10 and dimer fatty acid polyamides.

In a preferred from of the invention, the cassette 160 is fabricated from a material that is adhesively compatible with the upper and lower membrane 162, 164. What is meant by adhesive compatibility is the membrane can be attached to the cassette using standard heat sealing techniques. One particularly suitable material is a polymer blend of a polyolefin and a styrene and hydrocarbon copolymer. More particularly, the polyolefin of the polymer blend is a polypropylene and even more preferably a polypropylene copolymer with ethylene with an ethylene content of from about 1% to about 6% by weight of the copolymer. The styrene and hydrocarbon copolymer is more preferably an SEBS tri-block copolymer as defined above. The polypropylene copolymer should constitute from about 70% to about 95% and more preferably from about 80% to about 90% of the blend, and the SEBS will constitute from about 5% to about 30% and more preferably from about 10% to about 20% SEBS. In a preferred form of the invention, the polypropylene used to fabricate the cassette will have a lower melting point temperature than the high melt strength polypropylene used to fabricate the membrane. In a preferred form of the invention the polypropylene of the cassette 160 will have a melting point temperature of from about 120° C.-140° C. and for the film from about 145° C.-160° C. The cassette 160 can be injection molded from these polymer blends.

The upper and lower membranes 162, 164 are attached to the cassette 160 utilizing heat sealing techniques. The film has a peel strength of greater than 5.0 lbf/inch when tested with a tensile instrument until film failure or bond failure. Also, when the film is attached to the cassette it can be deformed under a pressure of 5 psi. The film maintains its low modulus and deformability properties even after sterilization to continue to meet the pumping requirement. The film has an extended shelf life. The film retains its pumping abilities even after two years shelf storage.

IV. Valve Actuator

Referring now to FIG. 15, one embodiment of an interface between the valve actuator 26 and the valve manifold 190 is illustrated. The valve motor 28 (not illustrated) of the valve actuator 26 drives a camshaft 200 through a mechanical linkage determinable to those of skill in the art. In an embodiment, a single camshaft 200 attaches to a series of cams 202, for example, one of each of the valves in the system 10 or 100. The cams 202 are fixed to the camshaft 200 and rotate in a one to one relationship with same.

The cams 202 drive pistons 204, which engage in a friction reduced way with the cams, for example, via rollers 206. The cams 202 drive pistons 204 up and down (only two of five cams shown having associated pistons to show other features of the actuator 26). When a cam 202 drives its associated piston 204 upward, the piston 204 engages one of the membranes 162 or 164 (typically the lower membrane 164, which is not shown in FIG. 15 for clarity) and pushes the membrane up into the respective hole 192 defined by the rigid manifold 190. This action stops the flow of medical fluid or dialysate through the respective valve.

The pistons 204 are also spring-loaded inside a respective housing 208. When the camshaft 200 turns so that a lower cam profile appears below one of the pistons 204, the spring inside the housing 208 pushes the piston 204 so that the roller 206 maintains contact with the respective cam 202. The piston 204 consequently moves away from the respective hole 192 defined by the rigid manifold 190, wherein the membrane 162 or 164, which has been stretched upward by the piston 204, springs back to its normal shape. This action starts the flow of medical fluid or dialysate through the respective valve.

The motor 28 is of a type, for example a stepper or servo motor, that can rotate a fraction of a rotation and stop and dwell for any predetermined period of time. Thus, the motor 28 can hold a valve open or closed for as long as necessary. The cams 202 are shaped to provide a unique combination of bumps and valleys for every flow situation. In certain situations, such as with valves V2 and V3 of the system 10, the valves always open and close together, so that both valves use the same cam 202 oriented in the same way on camshaft 200.

Figure 16A:
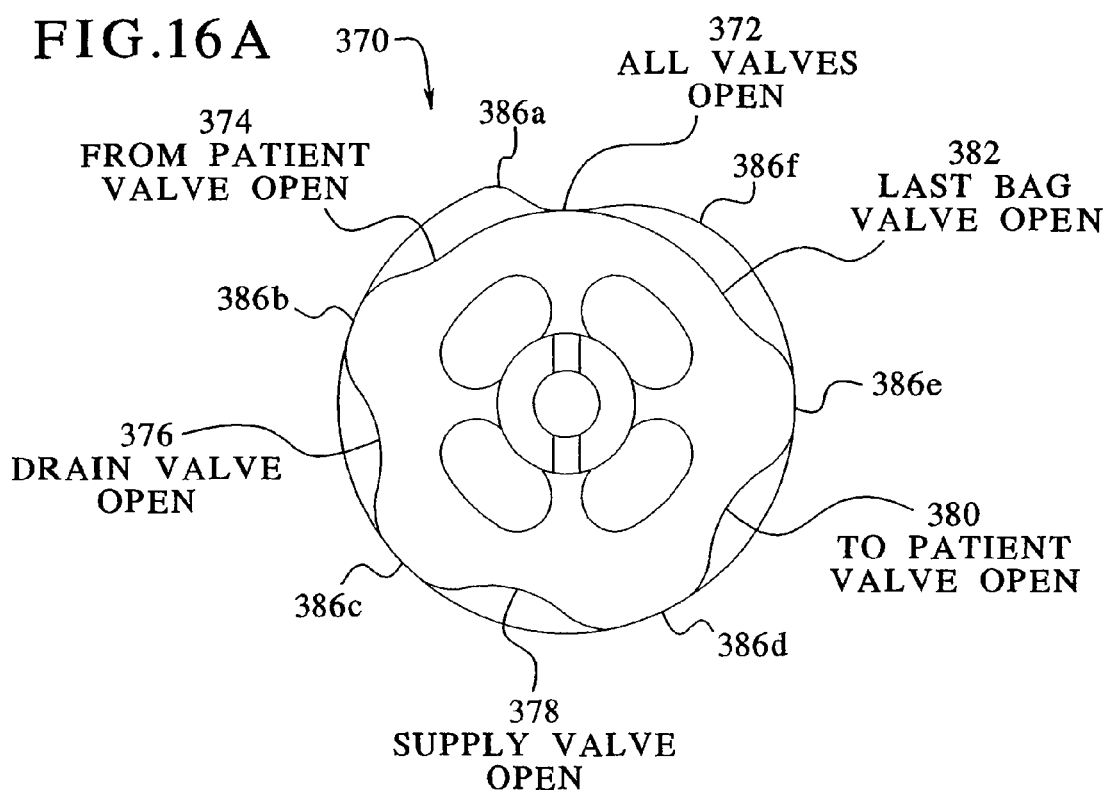
FIGS. 16A and 16B illustrate features of the camshaft and cam arrangement of the present disclosure.
Figure 16B:
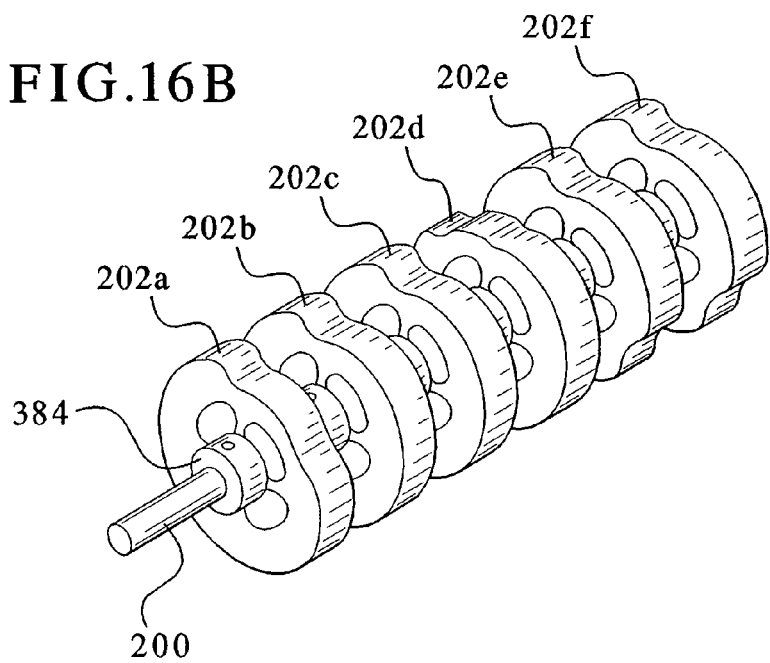

Referring now to FIGS. 16A and 16B, the camshaft 200 and cams 202 are illustrated figuratively. FIG. 16A illustrates a composite cam profile 370, i.e., a combination of each of the cams 202a to 202f illustrated in FIG. 16B. FIG. 16B illustrates that the cams 202a to 202f mount to the camshaft 200 via hubs 384. The hubs 384 may employ set screens as is well known. camshaft 200 can also have indentations, etc., for aligning the hubs 384. In an alternative embodiment, one or more of the cams 202a to 202f may be integrally formed with the otherwise camshaft 200. In an embodiment, the camshaft 200 is a single molded piece, which prevents the cams 202a to 202f from rotating with respect to one another. The single molded camshaft 200 supports or attaches to a plurality of or to all of the cams 202a to 202f.

As illustrated above in FIG. 15, each of the cams 202a to 202f of FIG. 16B drives a single piston 204 and roller 206 to operate a single valve head 192 of the rigid manifold 190. The cams 202a to 202f open or occlude the valve heads 192 according to the shape of the respective cam. FIG. 16B illustrates that the camshaft 200 supports six cams 202a to 202f. FIG. 15 illustrates five cams 200. The cam provided in the embodiment of FIG. 16B may be to open a last bag, illustrated by the "last bag valve open" position 382. Either of the systems 10 or 100 may include a last bag. The last bag is a final dialysate fill of about two liters into the patient before the patient disconnects from the system and resumes normal daily activities.

The valve motor 28 and the valve actuator 26 (FIGS. 1 and 2) rotate the camshaft 200 to open or close the valve heads 192 to create a desired solution flow path. The arrangement of the cams 202a to 202f on the camshaft 200 is made such that, at any time during the therapy, there is no more than one fluid path open at any given time. Further, when the valve actuator 26 rotates the camshaft 200 from one flow path open position to the next, the series of cams 202a to 202f close all the valves for a moment of time. The closing of each of the valves prevents dialysate from back-flowing or moving in the wrong direction. Still further, the cams 202a to 202f are arranged such that only one valve head 192 of the valve manifold 190 of the disposable unit 160 may be open at any given time. Therefore, there is no open fluid path in the event of a system failure or inadvertent power down. This safety feature prevents dialysate from free-flowing into the patient 12 or overfilling the patient 12.

The lid 116 for the housing 112 of the hardware unit 110 may be freely opened by an operator or patient to load the disposable unit 160 into the hardware unit. When this occurs, the controller 30 automatically commands the camshaft to rotate so that an "all valves open" position 372, illustrated by the composite profile 370, resides beneath the rollers 206 and pistons 204. In the "all valves open" position 372, the camshaft 200 is rotated such that a depression exists under each of the pistons 204 and associated rollers 206. Accordingly, the pistons 204 sit in a relatively low position, i.e., out of the way, when the operator or patient loads the disposable unit 160 and valve manifold 190 into the hardware unit 110. This enables the patient or operator to place a disposable unit 160 into the unit 110 without encountering an obstruction or opposing force by one or more of the pistons 206.

After the patient or operator loads the disposable unit into the hardware unit 110 and closes the lid 116, the controller 30 automatically rotates the camshaft 200 so that an "all valves closed" position 386a resides beneath the pistons 204 and rollers 206. As illustrated, the "all valves closed" position 386a resides adjacent to the "all valves open" position 372. When the camshaft 200 is rotated to the "all valves closed position" 386a, no fluid can flow through the system 10, 100. As the camshaft 200 rotates from the "all valves open" position 372 to the first "all valves closed" position 386a, a mechanical interlock (not illustrated) is moved into the camshaft 200, which prevents the rotation of the camshaft 200 back to the "all valves open" position 372. This prevents uncontrolled flow of the dialysate, which could occur when each of the valve heads 192 is open, in the event that the operator tries to open the lid 116 during therapy.

In an alternative embodiment, an interlock can be provided through software. An encoder provides positional and velocity feedback to the controller 30. The controller 30 therefore knows the position of the cam shaft 200. Thus, the controller 30 is able to prevent the rotation of the camshaft 200 back to the "all valves open" position 372.

When the patient closes lid 116, a second mechanical interlock (not illustrated) locks the lid in place, so that the patient cannot open the lid 116 during therapy. The system 10, 100 senses when the patient has removed the patient fluid line 292 and connector 290 from the transfer set, which is implanted in the patient 12. Only then will the system 10, 100 allow the patient to open the lid 116. The mechanical interlocks prevent free-filling, overfilling and the patient from tampering with the system while it is running. The valve configuration provides a fail safe system that prevents fluid flow in the event of a failure or power down.

In many instances, when the patient begins dialysis therapy, the patient is already full of dialysate. In the illustrated embodiment of FIG. 16A, therefore, the composite profile 370 provides the "all valve open" position 372 next to the "from patient value open" position 374. The "from patient valve open" position resides next to the "drain valve open" position 376. In this manner, upon therapy startup, camshaft 200 is readily positioned to be able to cooperate with the pump 20, 120 to drain spent dialysate from the patient. It should be appreciated that any of the cams 202a to 202f may be the cam that provides the "from patient valve open" position 374, the "drain valve open" position 376, etc.

Between the "from patient valve open" position 374 and the "drain valve open" position 376 resides a second "all valves closed" position 386b. Between each opening of a new valve and closing of a previously opened valve, each valve is momentarily closed. The controller 30 causes the motor (e.g., a stepper, servo or DC motor) and actuator 26 to toggle the camshaft 200 back and forth between the "from patient valve open" position 374, past the "all valves closed" position 386b, to the "drain valve open" position 376. In this manner, the pump 20, 120 is able to sequentially pull apart fluid from the patient 12 and dump it to drain 18.

When the system 10, 100 completes the initial patient drain cycle, the controller 30 causes the actuator 26 of motor 28 to rotate camshaft 200 past the "all valves closed" position 386c to the "supply valve open position" 378. To fill the patient full of fresh dialysate, the controller 30 causes the camshaft 200 to toggle back and forth between the "supply valve open" position 378 and the "to patient valve open" position 380, each time passing over the "all valves closed" position 386d. Again, for the drain and fill cycles, only one valve head 192 is open at any given period of time. The toggling always includes an "all valves closed" position between the dosing of one valve head 192 and the opening of another. The single pump sequentially pulls fluid into the disposable unit 160 and pushes fluid from same.

After the initial fill, camshaft 200 is positioned so that the camshaft 200 can once again toggle back and forth between the "from patient valve open" position 374, past the intermediate "all valves closed" position 386b, to the "drain valve open" position 376. When the patient is once again empty, the camshaft 200 is positioned so that the camshaft may be toggled back and forth between the "supply valve open" position 378 and the "to patient valve open" position 380. The system 10, 100 repeats this series of cycles as many times as necessary. Typically, the patient receives approximately 2 to 2.5 liters of dialysate in a single fill cycle. The two supply bags 14 each hold six liters of dialysate in an embodiment. This provides the system 10, 100 with four to six complete fill, dwell and drain cycles, which are provided, for example, through the night while the patient sleeps.

In many instances, the patient will receive a last bag fill at the end of the therapy, which the patient will carry for the day. To perform this procedure, the camshaft 200 toggles back and forth between the "from patient valve open" position 374 to the "drain valve open" position 376 to dump the preceding fill of peritoneal fluid to drain 18. Thereafter, the camshaft 200 is positioned to toggle back and forth between the "last bag valve open" position 382 and the "to patient valve open" position 380. In doing so, the camshaft 200 rotates past one of the all valves closed positions, namely, the "all valves closed position" 386e.

To prime the system, the camshaft 200 may be positioned and toggled in a number of different ways. In one embodiment, the camshaft 200 toggles back and forth between the "supply valve open" position 378 and the "drain valve open" position 376, passing over the "all valves closed" position 386c. This toggling in cooperation with the pumping of pump 20 or 120 causes the dialysate to flow from the supply bags 14, through the disposable unit 160, to drain 18. In another embodiment, using the vented tip protector 280 illustrated in connection with the FIGS. 8 to 12, the camshaft 200 toggles back and forth between the "supply valve open" position 378 and the "to patient valve open" position 380. This causes dialysate to flow from the bags 14, through the disposable unit 160, and into the patient fluid line 292 to the end of the vented tip protector 280. When dialysate reaches the hydrophobic membrane 300 of the vented tip protection 28, the pressure in the system 10, 100 rises, wherein a signal is received by the controller 30, which causes the pump 20, 120 to stop pumping and the camshaft 200 to stop toggling.

V. Medical Fluid Pump

A. Pump Hardware and Operation

Figure 17A:
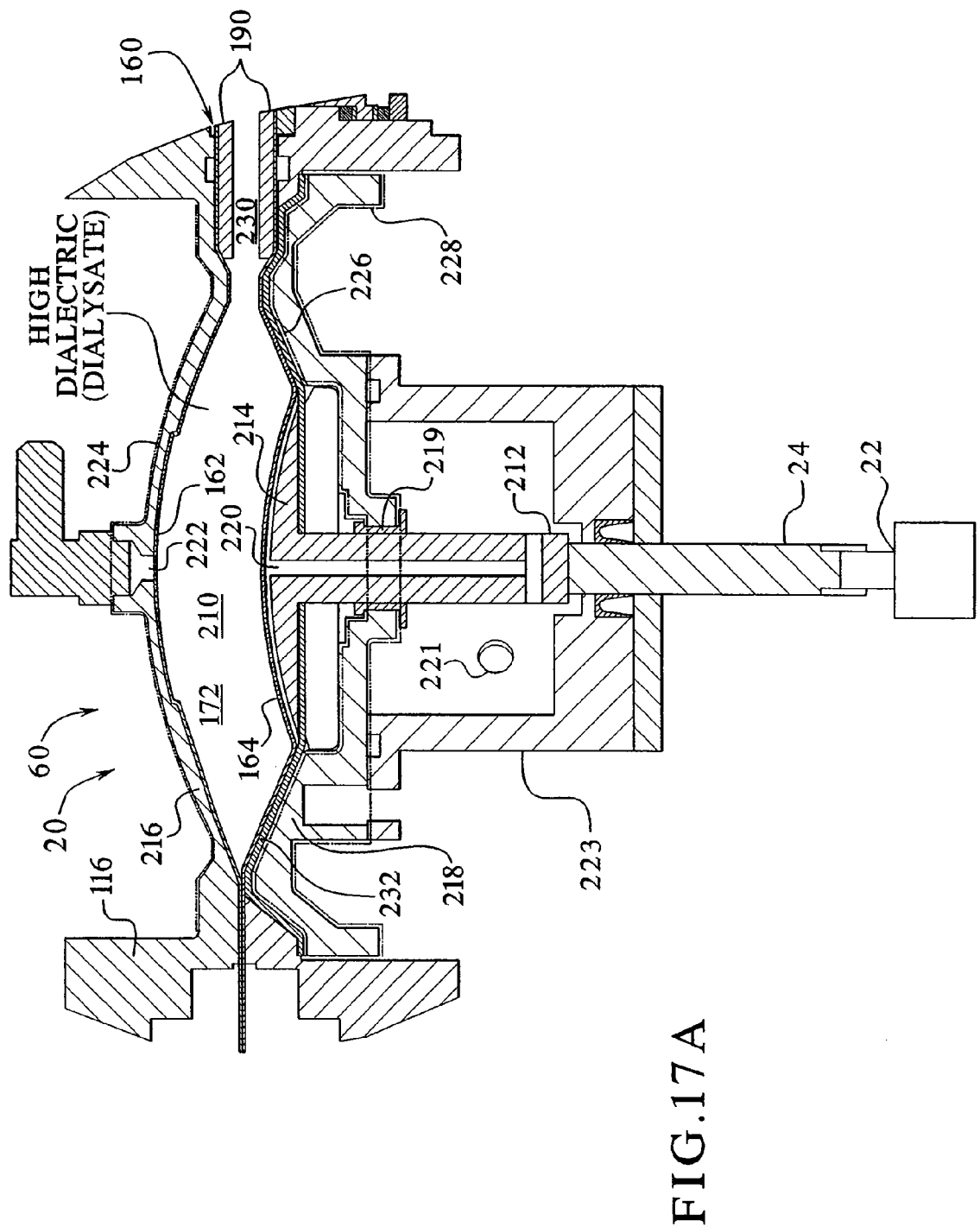
FIGS. 17A and 17B illustrate an embodiment of a mechanically operated fluid pump and capacitance type fluid volume sensor of the present disclosure.
Figure 17B:
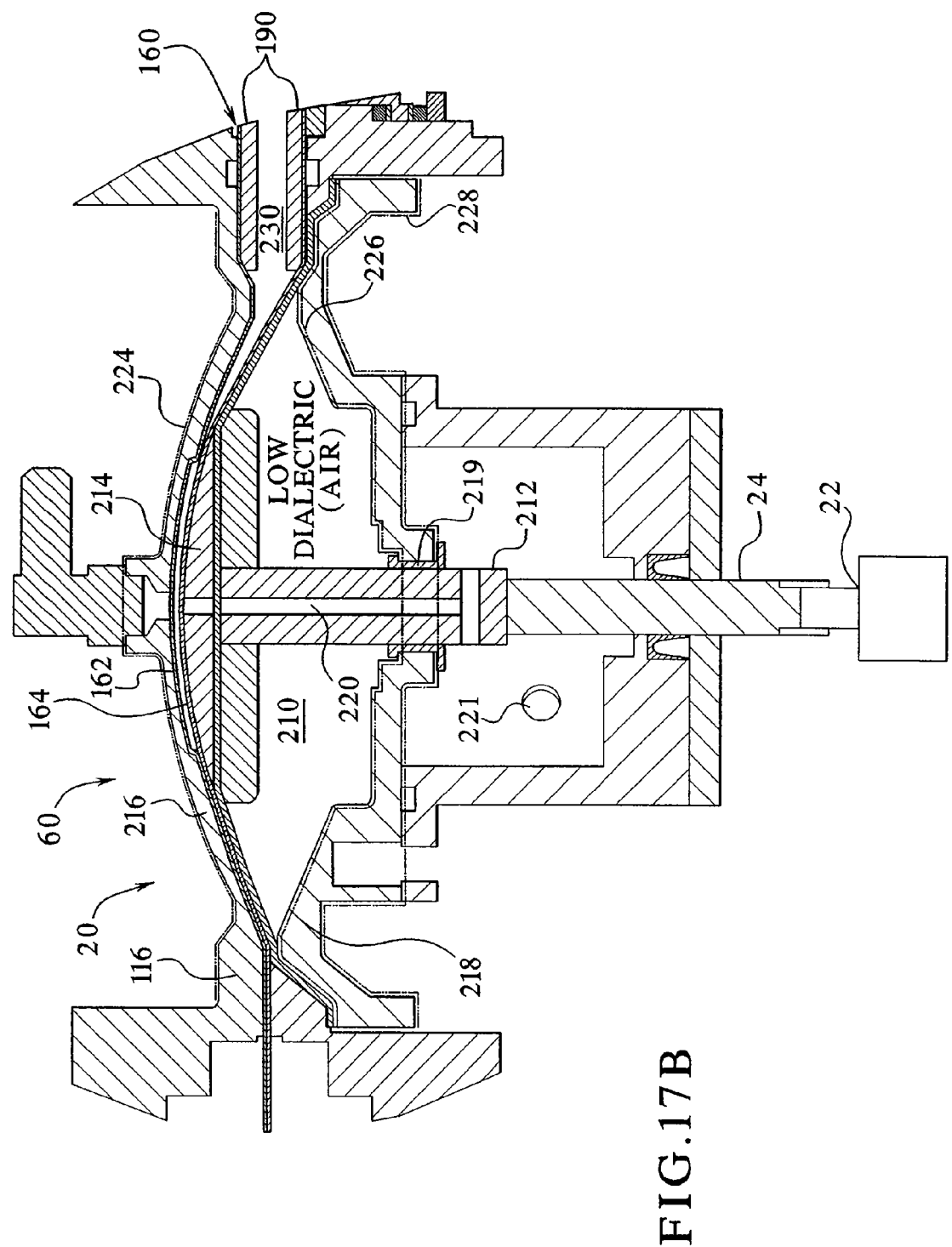

Referring now to FIGS. 17A and 17B, one embodiment of the pump 20 is illustrated. The lid 116 of the hardware unit 110 defines an upper chamber wall 216. Disposed within the housing 112 of the hardware unit 110 (FIGS. 3A to 4B) is a lower chamber wall 218. The chamber walls 216 and 218 define an internal chamber 210. The chamber 210 can have any desired shape, for instance the clamshell shape as illustrated in FIGS. 17A and 17B.

The lower chamber wall 218 defines or provides a sealed aperture 219 that allows a pump piston 212 to translate back and forth within the chamber 210. The piston 212 is attached to or integrally formed with a piston head 214. The piston head 214 in an embodiment has an outer shape that is similar to or the same as an internal shape of the upper chamber wall 216.

The pump piston 212 connects to or is integrally formed with the linear actuator 24. The linear actuator 24 in an embodiment is a device, such as a ball screw, that converts the rotary motion of a motor 22 into the translational motion of the piston 212. In one embodiment, the motor 22 is a linear stepper motor that outputs a translationally moving shaft. Here, the actuator 24 may simply couple the motor shaft to the piston 212. The linear or rotary stepper motor provides quiet linear motion and a very high positional resolution, accuracy and repeatability. Stepper motors are commercially available, for example, from Hayden Switch and Instrument Inc., Waterbury, Conn.

As described above, the flexible fluid receptacle 172 (seen in FIG. 17A but not in FIG. 17B) is defined by the expandable upper and lower membranes 162 and 164, respectively, of the disposable unit 160. In FIG. 17A, when the pump 20 is full of medical fluid, the pump chamber 210 and the membrane receptacle 172 have substantially the same shape. In FIG. 17B, when the pump 20 has displaced all or most all of the medical fluid, the pump chamber 210 maintains the same volume but the membranes 162 and 164 of the fluid receptacle 172 have collapsed to virtually a zero volume along the interior surface of the upper chamber wall 216.

Vacuum source 44 for the pump 20 is described above in connection with FIG. 1. The vacuum source 44 exerts a vacuum on the upper membrane 162, through the aperture or port 222. The aperture or port 222 extends through the upper chamber wall 216. The vacuum source 44 exerts a vacuum on the lower membrane 164, through an aperture 221 defined or provided by housing 223, and through the port or aperture 220. The port or aperture 220 extends through the piston 212, including the piston head 214. When a vacuum is applied, the lower membrane 164 seals against the piston head 214. The upper membrane 162 seals against the upper chamber wall 216.

The port 222 fluidly connects to channels (not illustrated) defined by the interior wall of the upper chamber wall 216. The channels extend radially outwardly from port 222 in various directions. The channels help to distribute the negative pressure applied through the port 222 to further enable the upper membrane 162 to substantially conform to the interior shape of the upper chamber wall 216. In a similar manner, the outer surface of the piston head 214 can include radially extending channels to further enable the lower membrane 164 to substantially conform, upon application of the vacuum, to the outer surface of the piston head 214.

The pump 20 also includes a diaphragm 232 tensioned between the upper and lower chamber walls 216 and 218, respectively. The diaphragm 232 defines, together with the upper chamber wall 218, a known, predictable and repeatable maximum volume of dialysate, which can be drawn from one or more of the supply bags 14 and transported to the patient 12. The diaphragm 232 also enables the volume of a partial stroke to be characterized, which also enables accurate and repeatable volume measurements.

The diaphragm 232 is disposed beneath the piston head 214 and around the piston 212. When the vacuum is applied to the port or aperture 220, the diaphragm 232, as well as the lower membrane 164, are pulled against the piston head 214. When the piston head 214 is actuated upwardly away from the lower chamber wall 218, with the vacuum applied through aperture 220, the membrane 164 and the diaphragm 232 remain drawn to the piston head 214. An inner portion of the membrane 164 conforms to the shape of the outer surface of the piston head 214. The remaining outer portion of the membrane 164 conforms to the shape of the exposed surface of the diaphragm 232.

The diaphragm 232 in an embodiment includes a flexible, molded cup-shaped elastomer and a fabric reinforcement, such as fabric reinforced ethylene propylene diene methylene ("EPDM"). The fabric can be integrally molded with the elastomer. The fabric prevents unwanted deformation of the diaphragm while under pressure. The diaphragm 232 can stretch when the piston 212 and head 214 move downwardly towards the lower chamber wall 218, pulling the diaphragm 232 along the crimped edges of the upper and lower chamber walls 216 and 218. The diaphragm 232 also moves and remains sealed to the piston head 214 when the piston 212 and head 214 move upwardly towards the upper chamber wall 216.

In operating the pump 20, negative pressure is constantly applied through the port 222 to hold the upper membrane 162 against the upper chamber wall 216. The manifold 190 of the disposable unit 160 (see FIGS. 3A and 5) define a fluid port opening 230 to the membrane receptacle 172. The fluid port opening 230 allows medical fluid or dialysate to enter and exit the membrane receptacle 172. The membrane receptacle 172 seats in place with the crimped edges of the upper and lower chamber walls 216 and 218. The seal 170 of the receptacle 172 may actually reside slightly inside the crimped edges of the upper and lower chamber walls 216 and 218 (see FIG. 4A).

During a pump fill stroke, with the upper membrane 162 vacuum-pressed against the upper chamber wall 216, and the lower membrane 164 and the diaphragm 232 vacuum-pressed against the piston head 214, the motor 22/actuator 24 cause the piston head 214 to move downwardly towards the lower chamber wall 218, increasing the volume within the flexible receptacle 172, and producing a negative pressure within same. The negative pressure pulls dialysate from the supply bags 14 or the patient 12 as dictated by the current valve arrangement. The opened receptacle 172 fills with fluid. This process occurs when the pump moves from the position of FIG. 17B to the position of FIG. 17A. FIG. 17A shows the pump 20 at the end of the stroke, with the receptacle 172 fully opened (i.e., full of fluid).

During a patient fill or drain stroke, again with the upper membrane 162 vacuum-pressed against the upper chamber wall 216, and the lower membrane 164 and the diaphragm 232 vacuum-pressed against the piston head 214, the motor 22/actuator 24 cause the piston head 214 to move upwardly towards the upper chamber wall 216, decreasing the volume within the flexible receptacle 172 and producing a positive pressure within same. The positive pressure pushes dialysate from the receptacle 172 to the patient 12 or the drain 18 as dictated by the current valve arrangement. The receptacle 172 closes as the lower membrane 164 moves upward towards the upper membrane 162. This process occurs when the pump moves from the position of FIG. 17A to the position of FIG. 17B. FIG. 17B shows the pump 20 at the end of the stroke, with the receptacle 172 empty or virtually empty.

In the event that air ("air" for purposes of this invention includes air as well as other gases which may be present, particularly those that have escaped from the patient's peritoneal cavity) enters the fluid receptacle 172, it must be purged to maintain accuracy. It should be appreciated that if air enters between the membranes 162 and 164, system 10, 100 in one embodiment does not have the ability to pull a vacuum between the membranes 162 and 164. The elasticity of the membranes 162 and 164, however, naturally tend to purge air therefrom. In an alternative embodiment the system 10, 100 can be adapted to provide a vacuum source that pulls a vacuum between the membranes 162 and 164 to purge air therefrom.

To purge air from between the membranes, the system 10, 100 also provides a positive pressure source. In systems 10, 100, for example, the pump motor 46 can be used in reverse of normal operation and, instead of producing vacuum source 44 (FIGS. 1 and 2), produce a positive pressure. The system 10 applies a positive pressure through the aperture or port 222 in the upper chamber wall 216 when air is detected between the membranes 162 and 164 or elsewhere in the disposable unit 160 or tubing. In one purge procedure, the controller 30 causes the motor 22/actuator 24 to move the piston head 214 to approximately a halfway point in either the positive or negative strokes. With the upper membrane 162 vacuum-pressed against the upper chamber wall 216, and the lower membrane 164 and the diaphragm 232 vacuum-pressed against the piston head 214 maintained at the halfway point, the controller causes the negative pressure source in through the aperture 222 to change to a positive pressure source, which pushes the upper membrane 162 conformingly against the lower membrane 164, which is supported by the piston head 214 and the diaphragm 232. Any air or fluid residing in the receptacle 172 is purged to drain as is any air between the receptacle 172 and drain 18.

B. Capacitance Volume Sensor

FIGS. 17A and 17B also illustrate that the pump 20 cooperates with an embodiment of the capacitance fluid volume sensor 60 of the system 10. One embodiment of a capacitance sensor 60 is disclosed in greater detail in the patent application entitled, "Capacitance Fluid Volume Measurement," Ser. No. 10/054,487, filed on Jan. 22, 2002, incorporated herein by reference. The capacitance sensor 60 uses capacitance measurement techniques to determine the volume of a fluid inside of a chamber. As the volume of the fluid changes, a sensed voltage that is proportional to the change in capacitance changes. Therefore, the sensor 60 can determine whether the chamber is, for example, empty, an eighth full, quarter full, half full, full, or any other percent full. Each of these measurements can be made accurately, for example, at least on the order of the accuracy achieved by known gravimetric scales or pressure/volume measurements. The present disclosure, however, is simpler, non-invasive, inexpensive and does not require the medical operation to be a batch operation.

Generally, the capacitance C between two capacitor plates changes according to the function $C = k \times (S/d)$, wherein k is the dielectric constant, S is the surface area of the individual plates and d is the distance between the plates. The capacitance between the plates changes proportionally according to the function $1/(R \times V)$, wherein R is a known resistance and V is the voltage measured across the capacitor plates.

The dielectric constant k of medical fluid or dialysate is much higher than that of air, which typically fills the pump chamber 210 when the piston head 214 is bottomed out against the upper chamber wall 216, as illustrated in FIG. 17B. Therefore, the varying distance, $\Delta d$, of the low dielectric displacement fluid between the expanding and contracting receptacle 172 and the lower chamber wall 218 may have some effect on the capacitance between ground capacitance plate 224 and the active capacitance plate 226. Likewise the surface area, S, of the capacitance plates and the moving membrane 164 may have some effect on the capacitance. Certainly, the changing overall dielectric from the high dielectric dialysate replacing the low dielectric air (or vice versa) affects the overall capacitance between the plates 224 and 226.

As the membranes 162 and 164 expand and fill with medical fluid, the overall capacitance changes, i.e., increases. The sensor 60 generates a high impedance potential across the grounded and active capacitor plates 224 and 226. The high impedance potential is indicative of an amount of fluid in the receptacle 172. If the potential does not change over time when it is expected to change, the sensor 60 can also indicate an amount or portion of air within the receptacle 172.

A capacitance sensing circuit amplifies the high impedance signal to produce a low impedance potential. The low impedance potential is also fed back to the guard plate 228, which protects the sensitive signal from being effected by outside electrical influences. The amplified potential is converted to a digital signal and fed to the processor 34, where it is filtered and/or summed. The video monitor 40 can then be used to visually provide a volume and/or a flowrate indication to a patient or operator. Additionally, the processor 34 can use the summed outputs to control the pump 20 of the system 10, for example, to terminate dialysate flow upon reaching predetermined overall volume.

Referring now to FIG. 18, the pump 120 of the system 100 is illustrated in operation with the capacitance sensor 60 of the present disclosure. The pump 120 forms a clamshell with first and second portions 246 and 248, which together form the pump chamber 250. The portions 246 and 248 are rigid, fixed volume, disked shaped indentations in the base 114 and lid 116 of the hardware unit 110. The clamshell first and second portions 246 and 248 are closed and sealed on the pump receptacle portion 172 of the disposable unit 110, which includes the expandable membranes 162 and 164.

An opening or aperture 252 is defined between the first and second clamshell portions 246 and 248 and the flexible membranes 162 and 164. The opening 252 enables medical fluid, for example, dialysate, to enter and exit the chamber 250 between the membranes 162 and 164 in the receptacle portion 172. The receptacle portion 172 fluidly communicates with the valve manifold 190.

FIG. 18 shows the pump chamber 250 in an empty state with both membranes 162 and 164 in relaxed positions, so that the flexible receptacle portion 172 is closed. The empty volume state is achieved when the membranes 162 and 164 have collapsed so that substantially all the fluid is removed from the sterile receptacle 172 and likewise the pump chamber 250.

The empty volume state can be achieved, for example, by allowing the elastic membranes 162, 164 to return to their relaxed, unstressed state as shown in FIG. 18. Also, both membranes 162 and 164 can be forced together against each other or against either one of the inside portions 246 and 248 of the pump chamber 250. When the pump chamber 250 is in the full state, the medical fluid resides between the membranes 162 and 164, wherein the membranes have been suctioned against the inner walls of portions 246 and 248.

It should be appreciated that either one or both of the membranes 162 and 164 can be moved towards and away from the clamshell portions 246 and 248 by any suitable fluid activation device. In various embodiments, the diaphragm pump is pneumatically or hydraulically actuated.

The diaphragm pump 120 of the system 100 does not require a separate piston or mechanical actuator as does the pump 20 of the system 10. The clamshell portions 246 and 248 define ports 254 and 256, respectively, to allow for movement of a displacement fluid (for example, pneumatic or hydraulic fluid) into and out of the chamber areas outside of the receptacle 172 to operate the diaphragm pump.

In an embodiment, the medical fluid, for example, dialysate, is suctioned into the receptacle 172 in the chamber 250. The receptacle 172, defined by membranes 162 and 164, may be filled with medical fluid by applying negative pressures to one or both of the chamber ports 254 and 256. The medical fluid can be emptied from the receptacle 172 by applying a positive pressure to at least one of the ports 254 and 256, or by allowing the membranes 162 and 164 to spring back into shape. In an alternative embodiment, the medical fluid, for example, dialysate, is pressurized from an external source to move in and out of the pump chamber 250 between the membranes 162 and 164.

The clamshell portions 246 and 248 form and hold the capacitor plates of the capacitance sensor 60. In an embodiment, upper clamshell portion 246 includes an active metal or otherwise conductive capacitance plate 258 between electrically insulative or plastic layers. A metal guard plate 260 is provided on the outer plastic layer of the upper clamshell portion 246. The guard plate 260 provides noise protection for the high impedance signal that transmits from the active capacitor plate 258.

As with the pump 20 of system 10, the active capacitor plate 258 of upper clamshell portion 246 of the pump 120 of the system 100 electrically couples to a capacitance sensing circuit. The guard plate 260 likewise electrically couples to the feedback loop of the capacitance sensing circuit as described above.

In an embodiment, lower clamshell portion 248 is also made of an inert plastic, wherein a metal capacitor plate 262 attaches to the outer surface of the lower clamshell portion 248. The metal capacitor plate 262 disposed on the outside of the clamshell portion 248 electrically couples to ground.

In one implementation, a negative pressure is constantly maintained at the lower port 256, so that the lower membrane 164 is pulled to conform to the inner surface of the grounded clamshell portion 248 during a multitude of fill and empty cycles. In this implementation, the upper membrane 162 does the pumping work. That is, when a negative pressure is applied to upper port 254 of upper clamshell 246, upper membrane 162 is suctioned up against and conforms with the inner surface of upper clamshell 246. This action draws fluid from the supply bag 14, through the manifold 190, and into the receptacle 172. To expel fluid, the negative pressure is released from upper port 254, wherein upper membrane 162 collapses to push the fluid from the receptacle 172. Alternatively, a positive pressure is applied through one or both ports.

In operation, the capacitance sensor 60 operates substantially as described in FIGS. 17A and 17B. The receptacle 172 expands between the portions 246 and 248. A varying distance, $\Delta d$, of the low dielectric displacement fluid between the expanding and contracting receptacle 172 and the portions 246 and 248 may have some effect on the capacitance between the ground plate 262 and the active plate 258. Likewise the surface area, S, defined by the ground and active capacitance plates and the expanding membranes may have some effect on the overall capacitance. Certainly, the changing overall dielectric from the high dielectric dialysate replacing the low dielectric air (or vice versa) affects the overall capacitance between the plates 258 and 262.

As the membranes 162 and 164 expand and fill with medical fluid, the capacitance changes, i.e., increases. Each different amount of medical fluid within the chamber 250 has a unique overall capacitance. A unique capacitance value can therefore be associated with each specific fluid volume in the chamber, for example, substantially empty, partially full, or substantially full.

As an alternative to the capacitance volume sensor 60 described above, the volume of dialysate fluid flowing through the automated systems 10 and 100 can be determined using other methods, such as through an electronic balance. In such a case, the electronic balance keeps track of the amount of dialysate that is supplied to the system during a priming of the system. The electronic balance also monitors any additional dialysate added to the system during dialysis treatment.

In other alternative embodiments, any of the systems described herein can be sensed using other types of flowmeters or devices employing Boyle's Law, which are known to those of skill in the art. Further, various other types of fluid volume measurement or flowrate devices can be used with the automated systems 10 and 100, such as orifice plates, mass flow meters or other flow measuring devices known to those of skill in the art.

VI. Precision Pressure Control

As discussed above, the system 10 employs a valve actuator 24 and a pump motor 22. In one embodiment the pump motor 22 is a stepper motor. In another embodiment, the motor 22 may be a DC motor or other type of repeatable and accurately positionable motor. Each of these types of motors enable system 10 to position the piston 212 and piston head 214 very accurately within the pump chamber 210. In the case of a high precision rotary motor 22, the actuator 24 converts the rotary motion into a translation motion precisely and moves the piston 212 back and forth within the chamber 210 within the accuracy and repeatability requirement of the system. The resolution of the linear stepper motor in an embodiment is about 0.00012 inches per step to about 0.00192 inches per step.

The pump motor 22 is also programmable. The programmable nature of the pump motor 22 enables acceleration, velocity and positional data to be entered into the controller 30, wherein the controller 30 uses the information to position the piston 212 and piston head 214 within the pump chamber 210, within an appropriate amount of time, to produce a desired amount of force or fluid pressure. The ability to preset the acceleration, velocity and position of the piston head 214 provides an advantage over purely pneumatic systems that respond relatively sluggishly to pneumatic signals.

The flexible nature of the PVC medical tubing described, e.g., in connection with FIG. 8 and the membrane material, described above in connection with FIGS. 13 and 14, causes the system 10 to have what is known as "compliance". Compliance is caused when the system 10 attempts to create fluid pressure, e.g., by moving the pump piston 212 and head 214, but instead causes the flexible tubing and membranes to expand. With the flexible tubing and membranes, compliance is inevitable. Eventually, when the tubing and membranes have expanded to their elastic limit, the pressure in the pump chamber 210 (i.e., in the receptacle 172) and throughout the tubing rises sharply. It is desirable to overcome the compliance of the tubing and membranes 162 and 164 as quickly as possible so that pressure may be built to drive the fluid.

The present disclosure uses a hybrid pressure control system that combines the ability to preset the pump piston acceleration and velocity with an adaptive pressure control scheme, which causes the pressure to achieve a desired pressure set point for any given stroke and causes the pressure to be fine tuned over time, i.e., over repeated strokes. That is, the present disclosure employs a method of controlling pressure within the system that seeks first to overcome system compliance and then seeks to achieve a desired pressure set point. The output of the present method of controlling pressure within the pump chamber 210 is illustrated by the velocity and pressure curves of FIG. 19.

Figure 19:
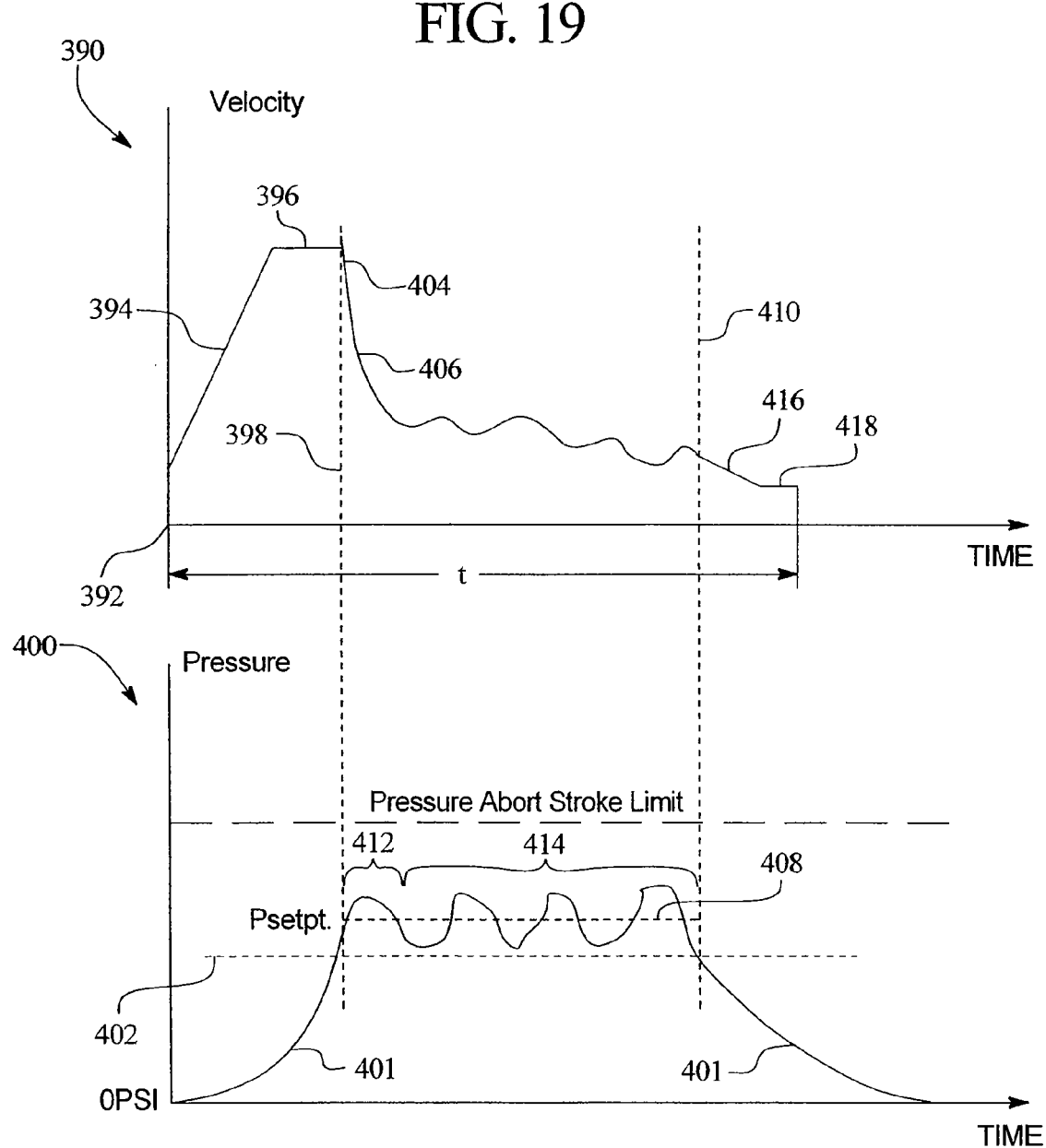
FIG. 19 is a graphical illustration of one embodiment of the present disclosure for the control of the pressure inside a fluid pump through precise velocity control of a pump piston.

In general, the system 10 controls the pressure within the receptacle 172 in the pump chamber 210 by controlling the velocity of the piston 212 and piston head 214. The velocity profile 390 of FIG. 19 illustrates a single pump stroke that occurs over a time "t" beginning at the start of stroke position 392. In the beginning of the stroke, the velocity ramps up at a preset acceleration 394. The preset acceleration 394 is programmed into the controller 30. When the velocity due to the preset acceleration 394 reaches a max velocity 396, the acceleration 394 changes to a zero acceleration, and the piston 212 moves at the constant max velocity 396.

During the time period of the acceleration 394 and the max velocity 396, which is designated by the dashed vertical line 398, the corresponding pressure as illustrated by a pressure curve 401 of pressure profile 400, ramps up beginning very slowly and exponentially increasing as the time reaches that of the dashed line 398. In the initial portion of the pressure curve, i.e., just after the start of stroke position, the pressure builds slowly as the compliance in the system is taken up. As the compliance is taken up, the pressure builds at faster and faster rates.

When the pressure reaches a pressure proximity threshold 402, set in software, the software within the controller 30 converts from the previous motion (acceleration, velocity, position) control to an adaptive control. It should therefore be appreciated that the method of controlling pressure within the fluid pump of the present disclosure is a hybrid type of control method, employing a combination of techniques.

The motion control portion, accented by the acceleration 394 and max velocity 396, represents a period in time when the method of control is forcing the system to overcome the pressure compliance. Upon reaching the pressure proximity threshold 402, the controller 30 causes the velocity to sharply decelerate at deceleration 404. Deceleration 404 reduces the velocity of the piston 212 and piston head 214 to a velocity 406, which is a velocity that aids in the ability of the adaptive control portion of the pressure control system to achieve a pressure set point 408. That is, without the programmed deceleration 404, the adaptive control portion would have a more difficult (i.e., longer) time controlling the velocity to make the pressure reach or substantially reach the pressure set point 408.

As explained in more detail below, the acceleration 394 is adaptively controlled in an embodiment, so as to reduce the amount of initial overshoot. The adaptive control over the acceleration 394 is fine tuned over time to further reduce the amount of initial overshoot. Each of these measures affects the amount of controlled deceleration 404 needed.

After the controlled deceleration 404 reaches the velocity 406 and until the time of the second dashed line 410, the system 10 operates in an adaptive mode. The second vertical line 410 occurs near the end of the stroke. As illustrated, the adaptive portion of the stroke is broken down into a number of areas, namely area 412 and area 414. Area 412 is characterized by the overshoot or undershoot caused by the programmed acceleration 394. In applying adaptive techniques, the adjustments or parameters that overcome area 414 error are tailored in software to combat overshoot or undershoot. The area 414 focuses on attempting to minimize the error between the actual pressure curve 401 and the pressure set point 408. During the area 414, the parameters and adaptive measures are tailored in software reduce the oscillation of the pressure curve 401 to achieve a pressure set point 408 as much as possible and as quickly as possible.

Upon reaching the time denoted by the dashed line 410, the pressure control method once again resumes motion control and decelerates the velocity at a controlled and predetermined deceleration 416 down to a final travel velocity 418, which is also the initial velocity at the start of the stroke 392. In an alternative embodiment, the method can simply let the adaptive control continue past the time line 410 and attempt to achieve the final travel velocity 418. After the time line 410, the pressure along pressure curve 401 falls off towards zero pressure as illustrated by the pressure profile 400. Comparing the pressure profile 400 to the velocity profile 390, it should be appreciated that pressure remains in the receptacle 172 of the pump chamber 210 even after the stroke ends at time "t". In some cases, the pressure overshoots as the piston 212 suddenly stops, wherein the momentum of the liquid produces a pressure spike after time "t".

Figure 20:
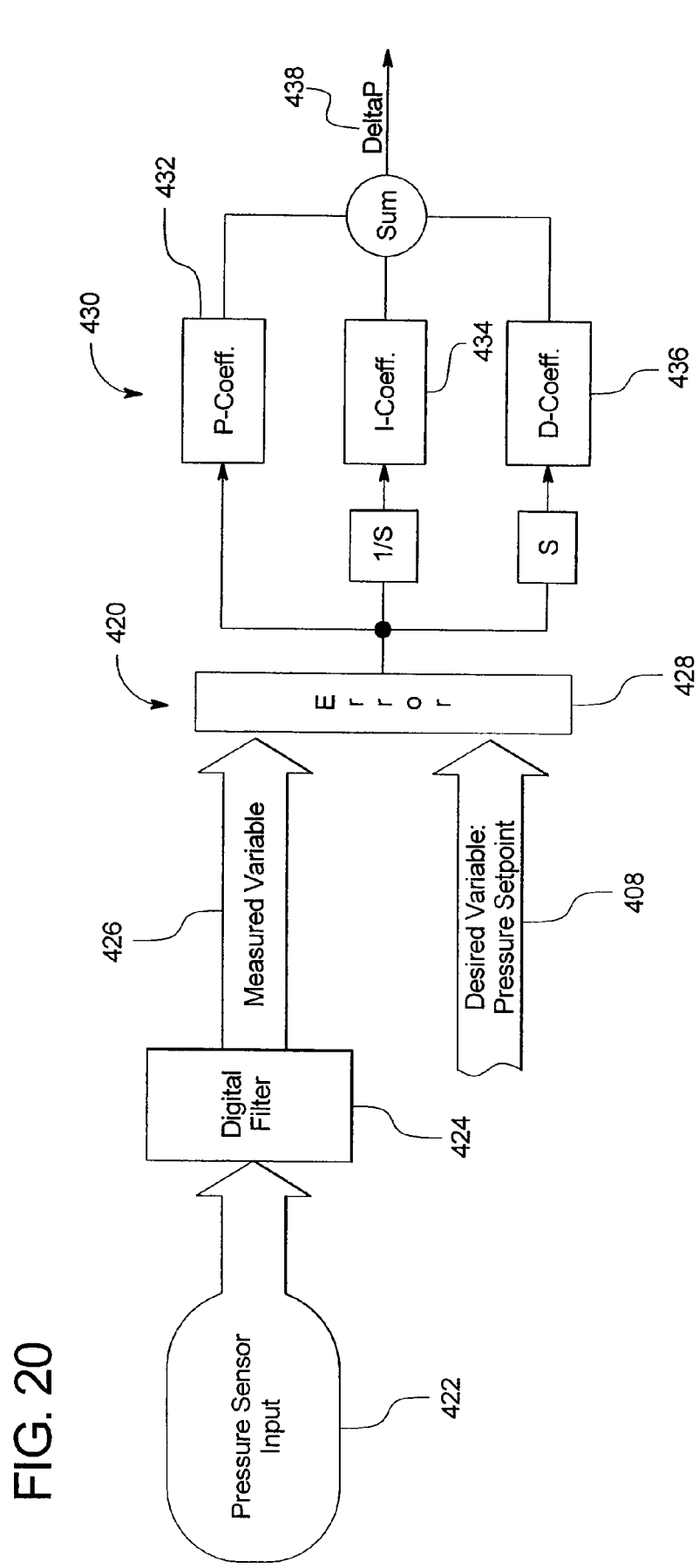
FIG. 20 is a schematic illustration of one embodiment of an algorithm of the present disclosure for performing proportional, integral and derivative type adaptive pressure control.

Referring now to FIG. 20, an algorithm 420 for employing the adaptive pressure control during the areas 412 and 414 of the pressure profile 400 is illustrated. In an embodiment, the adaptive control portion of the pressure control method employs a proportional, integral and derivative ("PID") adaptive parameters. In the method, a pressure reading is taken from a pressure sensor which senses the pressure inside the receptacle 172 of the pump chamber 210, and which provides a pressure sensor input 422 to the controller 30, as illustrated by the algorithm 420. Pressure sensor input 422 is sent through a digital filter 424, producing a measured variable 426. The measured variable 426 is compared with a desired variable, i.e., the pressure set point 408 illustrated in FIG. 19, wherein an error 428 is produced between the measured variable 426 and the desired pressure set point 408.

Next, the error 428 is entered into a PID calculation 430, which uses a proportional coefficient 432, an integral coefficient 434 and a differential coefficient 436. The output of the PID calculation 430 is an adaptive pressure change 438. The controller 30 then changes the velocity up or down to produce the pressure change 438.

In the pressure profile 400 of FIG. 19, the algorithm 420 of FIG. 20 is constantly being performed during the adaptive areas 412 and 414. As discussed below, the corrective parameters, e.g., the coefficients 432, 434 and 436, are used differently during the areas 412 and 414 because correction in the area 412 is focused on minimizing overshoot and undershoot, while correction in the area 414 however is focused on reducing error to zero about the pressure set point 408.

As described above, a single pump 20 is used in the system 10. The single pump 20 provides positive pressure during the patient fill stroke and the pump to drain stroke. The pump 20 also provides negative pressure during the pull from supply bag 14 stroke and the pull from patient 12 stroke. Of the four strokes, it is most important to accurately control the pressure during the patient fill and patient drain stoke. It is not as critical to control the pressure when pumping fluid from the supply bags 14 or when pumping fluid from the receptacle 172 of the pump chamber 210 to drain 18. In the two positive pressure strokes, one stroke, namely the patient fill stroke, it is critical to properly control pressure. In the two negative pressure strokes, one of the strokes, namely the pull from patient stroke, it is critical to properly control pressure. In the other two strokes, pressure is controlled without taxing the controller, motor 22 and disposable unit 160 needlessly.

Figure 21:
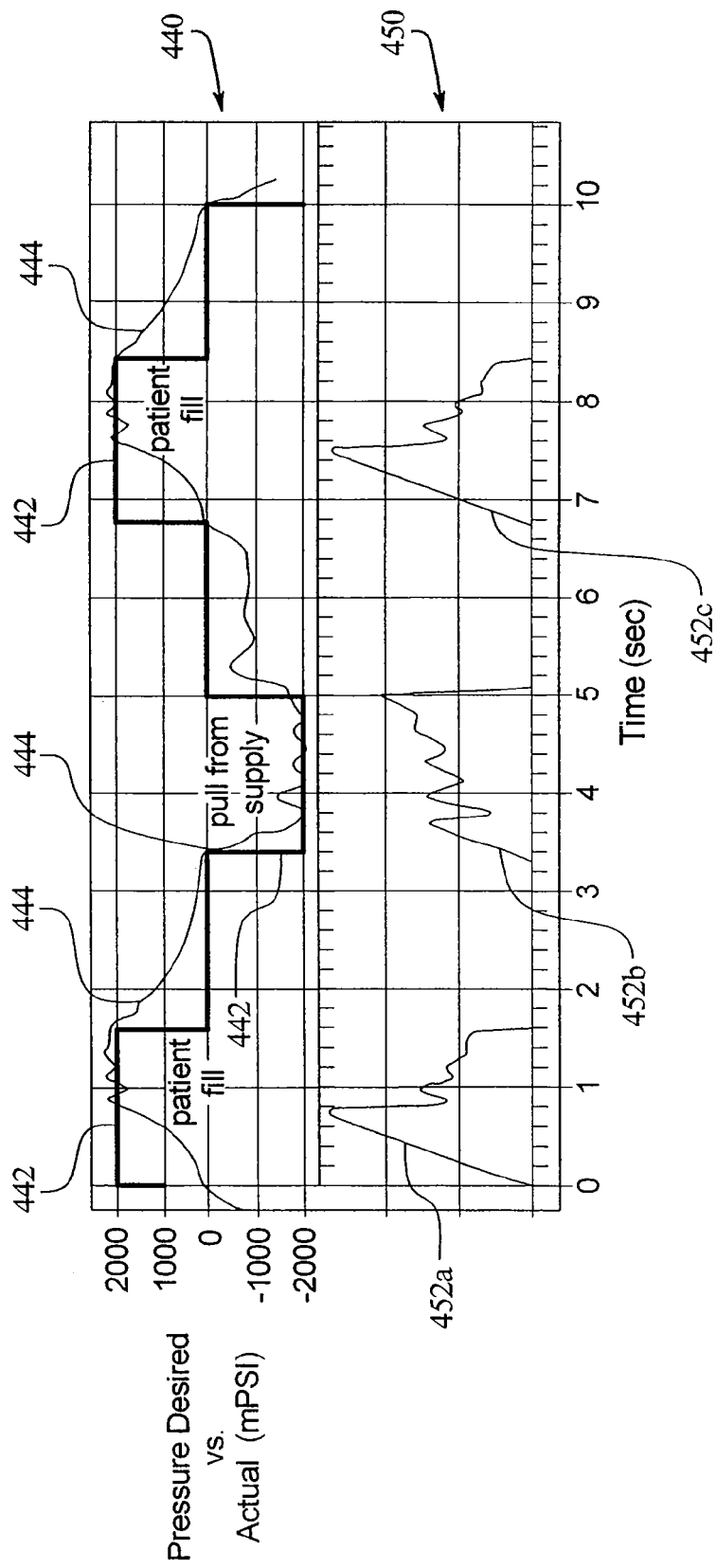
FIG. 21 is a graphical illustration of one embodiment of the present disclosure for the control of the pressure inside a fluid pump during repeated patient fill and pull from supply bag strokes.

Referring now to FIG. 21, pressure and velocity curves are shown for a number of strokes during the patient fill cycle. The upper profile 440 shows the actual pressure 444 versus the desired pressure 442 in milli-pounds per square inch ("mPSI"). The lower profile 450 shows corresponding velocity curves. In the pressure profile 440, the darkened line 442 corresponds to the desired pressure in mPSI. The curve 444 illustrates the actual pressure in mPSI. The curves 452a, 452b and 452c in the velocity profile 450 illustrate the piston velocities that produce the pressure fluctuations along the pressure curve 444 of the pressure profile 440. The velocity is measured in some increment of steps per second, such as milli-steps per second or micro steps per second when the motor 22 employed is a stepper motor. Different stepper motors for use in the present disclosure may be programmed in different increments of a step. The actual velocity is therefore a function of the resolution of the stepper motor.

At time zero, the desired pressure 442 changes virtually instantaneously to 2000 mPSI. The desired pressure curve 442 maintains this constant 2000 mPSI until reaching approximately 1.6 seconds, at which point the desired pressure 442 returns virtually instantaneously to zero. This step by the desired pressure curve 442 represents one complete patient fill stroke, wherein one full positive up-stroke of the piston 212 and piston head 214 within the pump chamber 220 occurs. In this step it is critical to control pressure because dialysate is being pumped into the patient's peritoneal cavity 12. The actual pressure curve 444 ramps up exponentially and oscillates about the 2000 mPSI set point in the manner described in connection with FIG. 19. It should also be noted that the velocity curve 452a follows a similar pattern to that shown in FIG. 19.

At about 1.6 seconds, i.e., when the piston head has reached the upper chamber 216 of the valve chamber 210, controller 30 stops the piston 212 from moving. The velocity of the piston head remains at zero until approximately 3.4 seconds. In this period, the valves have all been closed via one of the "all valves closed" positions illustrated in connection with FIG. 16A. As illustrated by pressure curve 444, residual fluid pressure resides within the pump chamber 210 even though the piston head 214 is not moving.

At about time 3.4 seconds, the desired pressure curve 442 switches virtuously instantaneously to −2000 mPSI. The pump 20 is now being asked to expand and form a negative pressure that pulls fluid from the supply bags 14. During this stroke, it is not as critical to control pressure as accurately in the patient fill stroke. Accordingly, the method may be programmed to bypass the motion control portion of the pressure control method and simply adaptively seek to find the pressure set point along line 442. Dialysate moves through the fluid heating path 180 of the disposable unit 160 (see FIGS. 3A and 5, etc.) during the patient fill stroke. Much of the compliance, i.e., stretching of the system occurs when the fluid passes through the path 180. Pumping fluid from the supply bag 14, however, does not require the fluid to pass through the heating path 180. The system 10 does not therefore experience the same level of compliance during this stroke. It is possible to pump from the bags 14 without using the motion control portion illustrated in connection with FIG. 19, since the lessened compliance may not require the "brute force" supplied by the controlled acceleration.

In FIG. 21, the pump completes the stroke that pulls dialysate from the supply bag at about five seconds. The demand pressure along curve 442 returns to zero accordingly. Next, the valve switches to an all closed position, the controller 30 sets the piston speed to zero, and the piston head resides substantially along the lower chamber wall 218, with the receptacle 172 full of fluid until approximately 6.8 seconds has passed, wherein the system 10 repeats the patient fill stroke as described previously.

Figure 22:
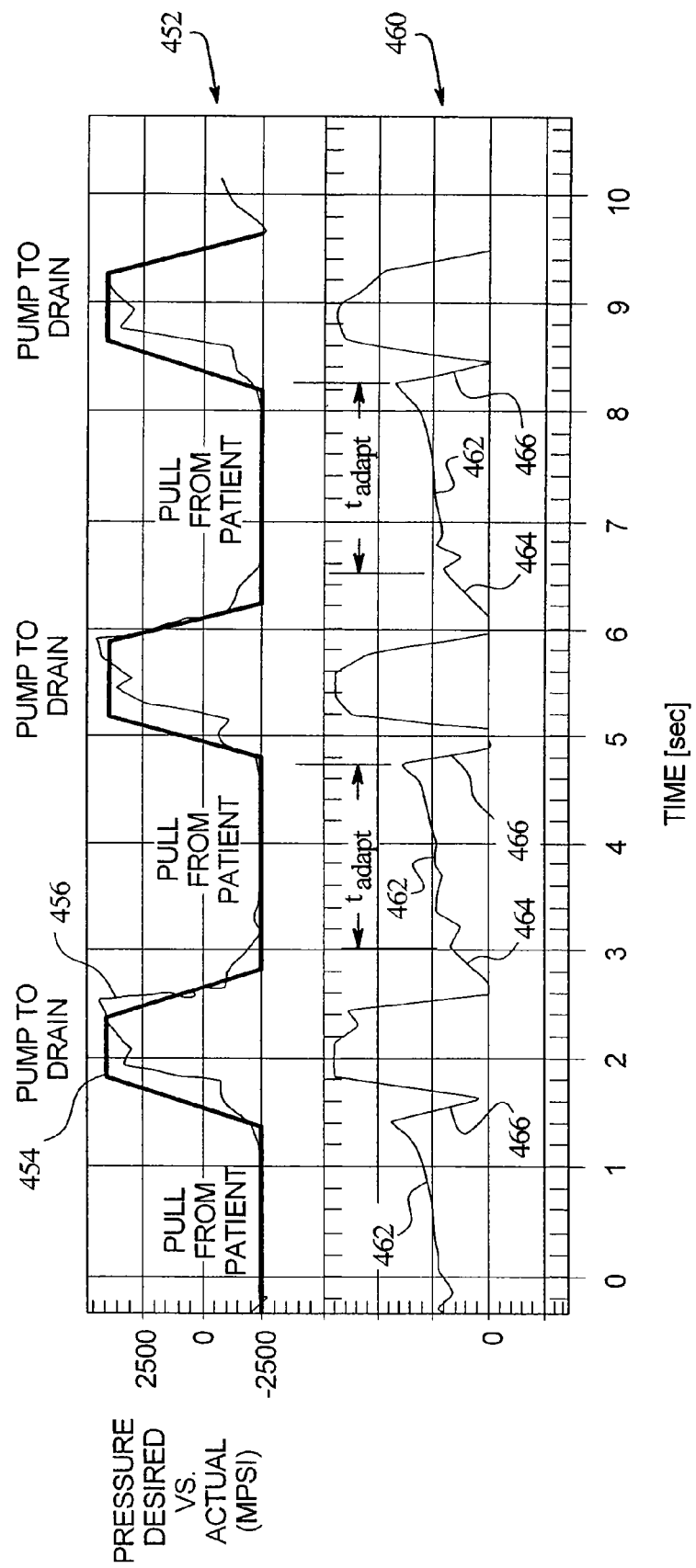
FIG. 22 is a graphical illustration of one embodiment of the present disclosure for the control of the pressure inside a fluid pump during repeated patient drain and pump to drain strokes.

Referring now to FIG. 22, a pressure profile 452 and a velocity profile 460 are illustrated for the patient drain stroke and the pump to drain stroke of the patient drain cycle. In the pressure profile 452, the demand pressure curve 454 illustrates that the controller calls for a negative 2500 mPSI to pull dialysate from the patient. The controller 30 calls for a positive pressure of 2500 mPSI to push fluid from the receptacle 172 of the pump chamber 210 to the drain bag 18. In the velocity profile 460 shown below the pressure profile 452, the actual velocity 462 in some increment of steps per second is illustrated. It should be appreciated that both velocity profiles 450 and 460 of FIGS. 21 and 22 are absolute velocities and do not illustrate that the pump piston 212 moves in positive and negative directions.

The actual pressure curve 456 of the profile 452 illustrates that the pressure is controlled to conform to the demand pressure line 454 more closely during the pull from patient portion than during the pump to drain portion of the profile 452. In an embodiment, the controller 30 is programmed to provide a motion controlled velocity 464 for a portion of the pull from patient stroke and use an adaptive control during the time "tadapt". The method also uses, in an embodiment, a controlled deceleration 466 at the end of the pull from patient stroke. Alternatively, the method allows the PID control to seek to find zero pressure. Similarly, during the pump to drain stroke, the controller 30 can switch to PID control only.

Figure 23:
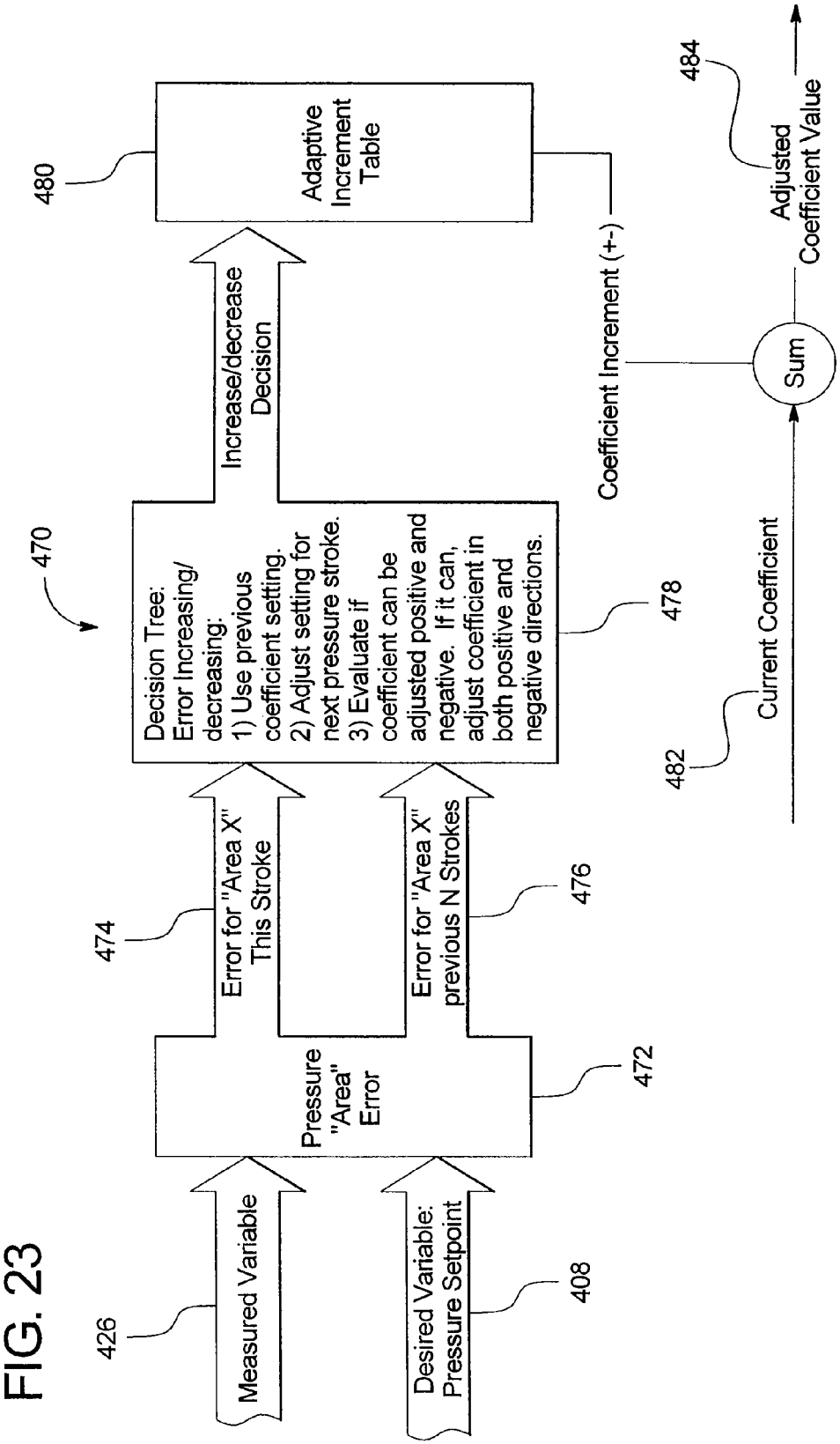
FIG. 23 is a schematic illustration of one embodiment of an algorithm of the present disclosure for adapting pressure error correction parameters over time to optimize pressure control efficiency.

Referring now to FIG. 23, one embodiment of an algorithm 470 illustrating the "fine tuning" adaptive control of the PID portion of the pressure control method of the present disclosure is illustrated. FIG. 23, like FIG. 20, includes a measured pressure variable 426 and a desirable pressure set point 408. The pressure error 472 represents an error in either the overshoot area 412 or the oscillation area 414 illustrated in the pressure velocity profile 400 of FIG. 19. For each area, the algorithm 470 looks at two error components, namely, the error 474 determined in the current stroke and the error 476 stored for previous strokes. The controller 30 compares the two errors 476 and 478 and makes a decision as illustrated in decision block 478.

In the block 476, if the current stroke error 474 is less than the previous stroke error 476, the method uses the previous coefficient because the previous coefficient is currently having a desirable result. If the current stroke error 474 is greater than the previous strokes error 476, two possibilities exist. First, the coefficient or corrective measure taken is not large enough to overcome the error increase. Here, the coefficient or corrective setting can be increased or another tacetic may be employed. Second, the previous corrective procedure may be having an adverse impact, in which case the parameter connection can be reversed or another tactic can be employed. Obviously, to employ algorithm 470, the method provides that the controller 30 store the manner of the previous corrective attempts and outcomes of same. Based on what has happened previously, the controller decides to increment or decrease one or more of the parameters. The amount of increase or decrease is then applied to one or more coefficients stored in an increment table 480. The adjusted or non-adjusted increment is then summed together with the currently used one or more coefficients 482 to form an adjusted one or more coefficients 484.

Referring now to FIG. 24, table 500 illustrates various different coefficients and adaptive perimeters for the pressure control method of the present disclosure. Certain of the coefficients and parameters apply more to the motion control portion of the profiles illustrated above, i.e., the set acceleration, deceleration and velocity portions of the profiles. The motion control parameters, however, effect the error, which influences the adaptive parameters in the PID portion of the pressure control. Other parameters apply to the adaptive control portions of the profiles. Adjusting the beginning stroke acceleration parameter 486 (illustrated by the acceleration 394 of the velocity profile 390 of FIG. 19) affects the motion control portion of the present method. Acceleration as illustrated, affects overshoot and the efficient use of stroke time. That is, it is desirable to have a high acceleration to overcome compliance quickly, however, the cost may be that overshoot increases. On the other hand, a lower acceleration may reduce overshoot but require more time to overcome the compliance in the system.

The proximately threshold parameter 488 (illustrated by pressure line 402 in the pressure profile 400 of FIG. 19) also affects overshoot and undershoot. Here, setting the pressure threshold 488 too low may cause undershoot, whereas setting the parameter 488 too high may cause overshoot. The DP/dt parameter 490 is the change in pressure for a given period of time. This parameter seeks to achieve, for example in FIG. 19, a certain slope of the pressure curve 401.

The maximum travel velocity parameter 492, illustrated as line 396 in the velocity profile 390 of FIG. 19, also affects overshoot and subsequent resonance. Another corrective factor is the conversion to pressure deceleration 494 corresponding to line 410 of FIG. 19. The method includes running the system without changing back to motion control and instead leaving the system in the adaptive PID control. The conversion to deceleration can have a large impact on the residual pressure remaining in the pump chamber 210 after the valves close.

The PID factors Kp, Kd and Ki, labeled 496, 498 and 502, respectively, affect the adaptive control portion of the present method but also affect, to a lesser extent, the controlled declaration at the end of the stroke. Each of the PID factors or parameters can be changed and adapted in mid-stroke. Also as illustrated in FIG. 23, the factors can be changed so as to optimize the system over time.

Each of the above-described factors can be used to insulate the fluid pressure from changes in the environment outside of the system 10. For example, the factors can overcome changes due to physiological and chemical changes in the patient's abdomen. Also, the height of the patient supply bags 14 affects the initial loading of the fluid pump 20. The parameters illustrated in FIG. 24 automatically overcome the changes due to bag height. Further, as the patient sleeps through the night, the supply bags 14 become less and less full, while the drain bag 18 becomes more full, both of which affect the pump pressure. The parameters illustrated in FIG. 24 are automatically adjustable to compensate for these changes and keep the system running smoothly.

Certain of the above-described factors is changed more and used more during the overshoot area 412 illustrated in the pressure profile 400 of FIG. 19. Other factors and parameters are used and changed more during the oscillation portion 414 of the profile 400.

VII. In-Line Heater

In an embodiment, the inline heater 16 includes two electrical plate heaters, which are well known to those of skill in the art. The plate heaters of the heater 16 have a smooth and flat surface, which faces the disposable unit 160. In an alternative embodiment, the automated systems 10 and 100 provide an in-line heater 16 having a plate heater in combination with an infrared heater or other convective heater.

In the alternative dual mode type heater, both the plate heater and, for example, the infrared heater are in-line heaters that heat the medical fluid that flows through the fluid heating path 180 of the disposable unit 160. The radiant energy of the infrared heater is directed to and absorbed by the fluid in the fluid heating path 180. The radiant energy or infrared heater in an embodiment is a primary or high capacity heater, which can heat a relatively large volume of cold fluid to a desired temperature in a short period of time.

The plate heater of the alternative dual mode heater in an embodiment is a secondary or maintenance heater which has a relatively lower heating capacity relative to the infrared heater. As described above, the plate heater uses electrical resistance to increase the temperature of a plate that in turn heats the fluid flowing though the path 180 adjacent to the plate.

The dual mode heater is particularly useful for quickly heating cool dialysate (high heat energy demand) supplied from one of the supply bags 14 to the automated system 10 or 100. Initial system fills can be cooler than later fills, and the system can lose heat during the dwell phase. The temperature of the dialysate at initial system fill can therefore be quite low, such as 5° C. to 10° C. if the supply bags 14 are stored in cold ambient temperature.

The plate heater and the infrared heater of the dual mode heater embodiment of the heater 16 can be arranged in various configurations relative to each other. The dual mode heaters in an embodiment are arranged so that the fluid passes by the heaters sequentially (e.g., first the plate heater and then the radiant or infrared heater). In another embodiment, the fluid passes by the heaters simultaneously (both heaters at the same time). The fluid flow path past the heaters can be a common flow path for both heaters, such as in the fluid heating path 180, or include independent flow paths for each heater.

VIII. Fuzzy Logic for Heater Control

Similar to the controlling of the fluid pressure, the control of the plate heater 16 is also subject to a number of environmental variables. For example, the ambient temperature inside the patient's home affects the amount of heat that is needed to raise the temperature of the medical fluid to a desired temperature. Obviously, the temperature of the dialysate in the supply bags 14 affects the amount of heat that is needed to raise the fluid temperature to a desired temperature. Plate heater efficiency also affects the amount of heating needed. Further, the voltage provided by the patient's home is another factor. Typically, a doctor or caregiver prescribes the temperature of the dialysate for the patient to be controlled to around a temperature of 37° C. It is, therefore, desirable to have a method of controlling the heater 16 to correct for outside temperature gradients so as to maintain the proper patient fluid temperature.

Figure 25:
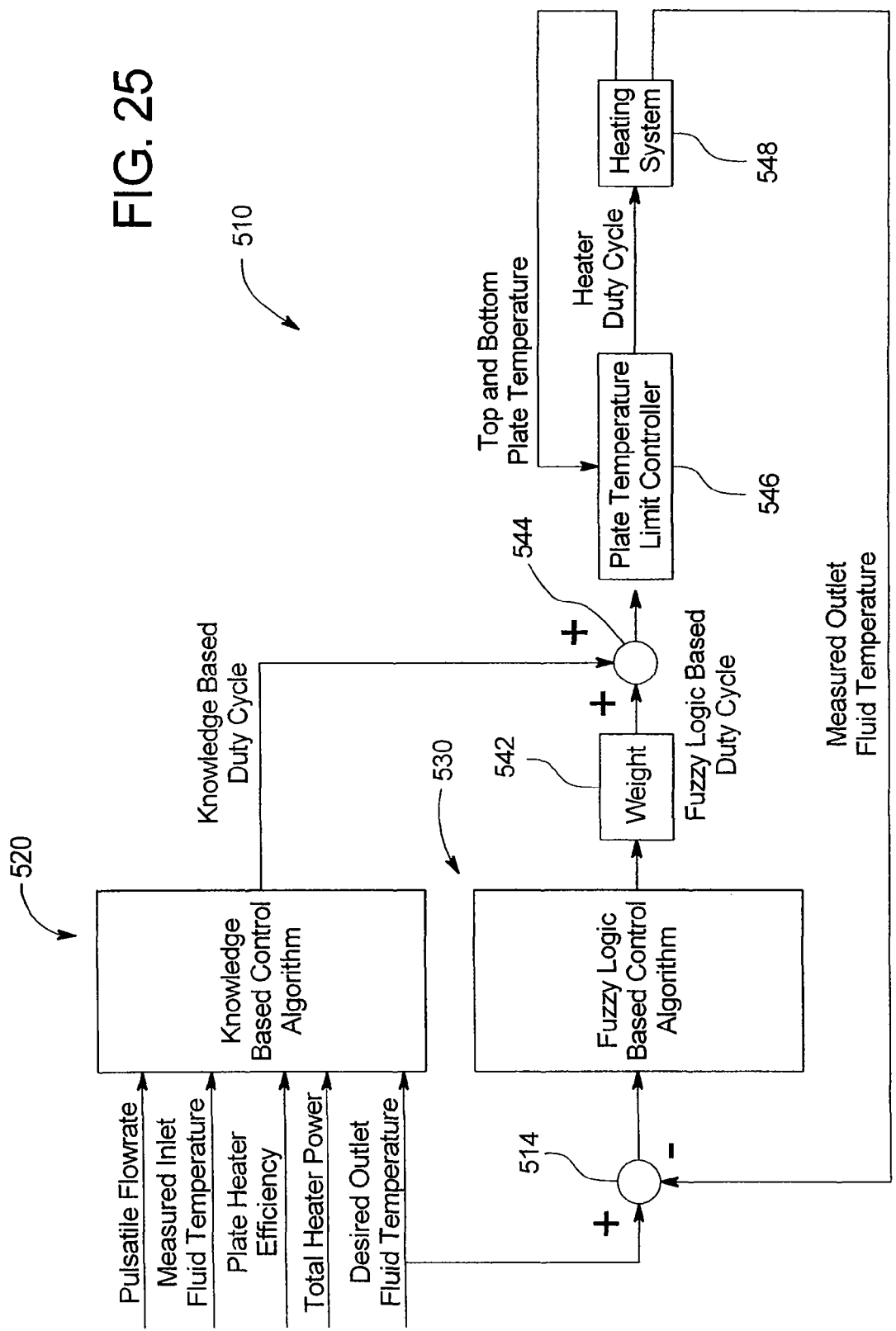
FIG. 25 is a schematic representation of one embodiment of a heater control method of the present disclosure.

Referring now to FIG. 25, one embodiment of a heating control method 510 is illustrated. The method 510 includes two separately performed algorithms 520 and 530 that operate in parallel to form an overall output 544. The algorithm 520 is termed a "knowledge-based" control algorithm. The knowledge-based control algorithm is based on knowledge, such as empirical data, flow mechanics, laws of physics and lab data, etc.

The knowledge-based algorithm 520 requires a number of inputs as well as a number of constant settings. For example, the control algorithm 520 requires an input pulsatile flowrate. As illustrated below, the pulsatile flowrate is actually calculated from a number of input variables. The system 10, 100 of the present disclosure provides fluid to the patient 12 in pulses, rather than on a continuous basis. It should be readily apparent from the discussion based on FIGS. 16A and 16B, that when all valve heads in the disposable are closed, no fluid can flow through the fluid heating pathway to the patient. The flowrate of fluid to the patient is therefore a pulsatile flowrate, wherein the patient receives the dialysate in spurts or pulses. It is difficult to control fluid temperature with this type of flowrate. To this end, the method 510 provides the dual algorithms 520 and 530.

Besides the pulsatile flowrate, the knowledge-based control algorithm 520 also receives a measured, i.e., actual, fluid inlet temperature signal. Further, the algorithm 520 stores the plate heater efficiency, which is based on empirical data. In one embodiment, the upper and lower plates of the plate heater 16 are around 95% efficient. Algorithm 520 also inputs the total heater power, which is derived from the voltage input into the system 10, 100. Residential voltage may vary in a given day or over a period of days or from place to place.

The algorithm 520 also inputs the desired outlet fluid temperature, which is a constant setting but which may be modified by the patient's doctor or caregiver. As illustrated in FIG. 25, the desired outlet fluid temperature is inputted into both the knowledge-based control algorithm 520 and the fuzzy logic based control algorithm 530. As discussed in more detail below, the knowledge-based control algorithm 520 outputs a knowledge-based duty cycle into a summation point 544.

With respect to the fuzzy logic-based control algorithm 530, the desired fluid temperature is inputted into a comparison point 514. The comparison point 514 outputs the difference between the desired fluid temperature and the actual measured fluid temperature exiting the heating system 548. The fuzzy logic-based control algorithm 530 therefore receives a change in temperature ΔT as an input. As described below, the fuzzy logic-based control algorithm 530 employs the concepts and strategies of fuzzy logic control to output a fuzzy logic duty cycle.

In the method 510, the knowledge-based duty cycle is adaptively weighted against the fuzzy logic-based duty cycle. In an alternative embodiment, the system predetermines a relative weight. In the method 510, the fuzzy logic-based duty cycle is weighted, i.e., provided a weight factor as illustrated in block 542. For example, if the fuzzy logic-based duty cycle is given a weight factor of one, then the fuzzy logic-based duty cycle is weighted equally with the knowledge-based duty cycle. If the fuzzy logic-based duty cycle is given a weight factor of two, the fuzzy logic-based duty cycle is given twice the weight as the knowledge-based duty cycle. The weight factor in block 542 can change over time and/or be optimized over time.

It should be appreciated that the weighting block 542 could alternatively be placed in the knowledge-based duty cycle output. As discussed below, however, the update rate of the fuzzy logic control loop is substantially higher than the update rate of the input signals entered into the knowledge-based control algorithm 520. It is therefore advantageous to weight the fuzzy logic-based duty cycle, as opposed to the knowledge-based duty cycle.

The weighted fuzzy logic-based duty cycle and the knowledge-based duty cycle are summed together at summing point 544 to produce an overall heater duty cycle. Duty cycle is one way to control the power input and, thus, the plate temperature of the heater. Controlling the duty cycle means controlling the percentage of a time period that full power is applied to the heater, for example, plate heater 16. In an alternative embodiment, the output of the parallel control algorithms 520 and 530 could be a percentage of full power applied at all times. Still further, the output of the parallel control algorithms 520 and 530 could be a percentage of full power applied for a percentage of a time period. For purposes of illustration, the method 510 is described using a duty cycle output which, as explained, is the percent of a time period that full power is applied to the heater.

As described herein, the heating system 548 (i.e., heater 16) in one embodiment is a plate heater, wherein upper and lower plates are disposed about a fluid heating path of the disposable unit 160. It should be appreciated, however, that the method 510 is equally applicable to the infrared heater previously described. Further, the method 510 is equally applicable to the combination of different types of heaters, such as, the combination of a plate heater and an infrared heater.

The method 510 uses multiple temperature sensors, such as the sensors 62 illustrated in FIGS. 1 and 2, which sense the temperature at different times within the method 510 and places within system 10,100. One sensor senses the fluid outlet temperature, which feeds back from the heating system 548 to the comparison point 514. Another two temperature sensors sense the temperature of the top plate and the bottom plate and feed back to the temperature limit controller 546, located in software.

As illustrated, before the summed heater duty cycle is inputted into the heating system 548, the system determines whether the top and bottom heating plates are already at a maximum allowable temperature. There exists a temperature above which it is not safe to maintain the plates of the plate heater. In a situation where one or both of the plates is currently at the temperature limit, the method 510 outputs a zero duty cycle, regardless of the calculations of the knowledge-based control system 520 and the fuzzy logic-based algorithm 530. To this end, the temperature of the top and bottom plates is fed back into the block 546, wherein the software only allows a heater duty cycle to be applied to the heating system 548 if the current temperature of the top and bottom plates is less than the temperature limit.

In an embodiment, if one of the plates is at the limit temperature, the method 510 provides a zero duty cycle to both plate heaters, even though one of the plate heaters may be below the temperature limit. Further, the software may be adapted so that if the actual temperature of the plate heater is very close to the limit temperature, the method 510 only allows the duty cycle be at or below a predetermined set point. In this manner, when the actual temperature is very near the limit temperature, the method 510 goes into a fault-type condition and uses a safe duty cycle.

Assuming the actual plate temperatures are below the safe temperature limit, the method 510 applies the combined heater duty cycle from the parallel control algorithms at summation point 544. The heater duty cycle applies full power for a certain percentage of a given amount of time. The given amount of time is the update speed of the fuzzy logic control loop. The fuzzy logic control loop, including the fuzzy logic control algorithm 530, updates about nine times per second in one embodiment. It should be appreciated that the update rate of the fuzzy logic control loop is an important parameter and that simply increasing the update rate to a certain value may deteriorate the accuracy of the system. One range of update rates that provide good results is from about 8.5 times per second to about 9.5 times per second.

The update rate should not be evenly divisible into the frequency of the input power. For example, an update rate of nine times per second works when the AC frequency is held steady at 50 or 60 hertz. However, as is the case in some countries, the frequency may be 63 hertz. In such a case, an update rate of nine hertz will cause inaccuracy. Therefore, in one embodiment, an update rate of a fraction of 1 hertz is suitable, such as 9.1 hertz. Assuming the update rate to be nine times per second, the time per update is approximately 110 milliseconds. Therefore, if the duty cycle is 0.5, i.e., half on, half off, the time at which full power is applied is 55 milliseconds. During the other 55 milliseconds, no power is applied. If the duty cycle is 90%, then full power is applied for 90% of 110 milliseconds.

The update speed of the knowledge-based control algorithm 520 is not as critical as the update speed of the fuzzy logic control loop. For one reason, the signal inputs to the algorithm 520 change gradually over time so that they do not need to be checked as often as the comparison between the desired fluid temperature and the actual fluid temperature. An update rate of about two seconds is sufficient for the signal inputs. The inputs of the control algorithm 520 can be updated from about once every half second to about once every four seconds. The knowledge-based control algorithm 520 can run on the main processor of the system 10, 100, for example, an Intel StrongARM™ Processor. To facilitate the update rate of the fuzzy logic control loop, a high speed processor, such as a Motorola Digital Signal Processor is used. The fuzzy logic-based control algorithm 530 runs, in one embodiment, on a delegate processor, e.g., a Motorola Digital Processor.

Figure 26:
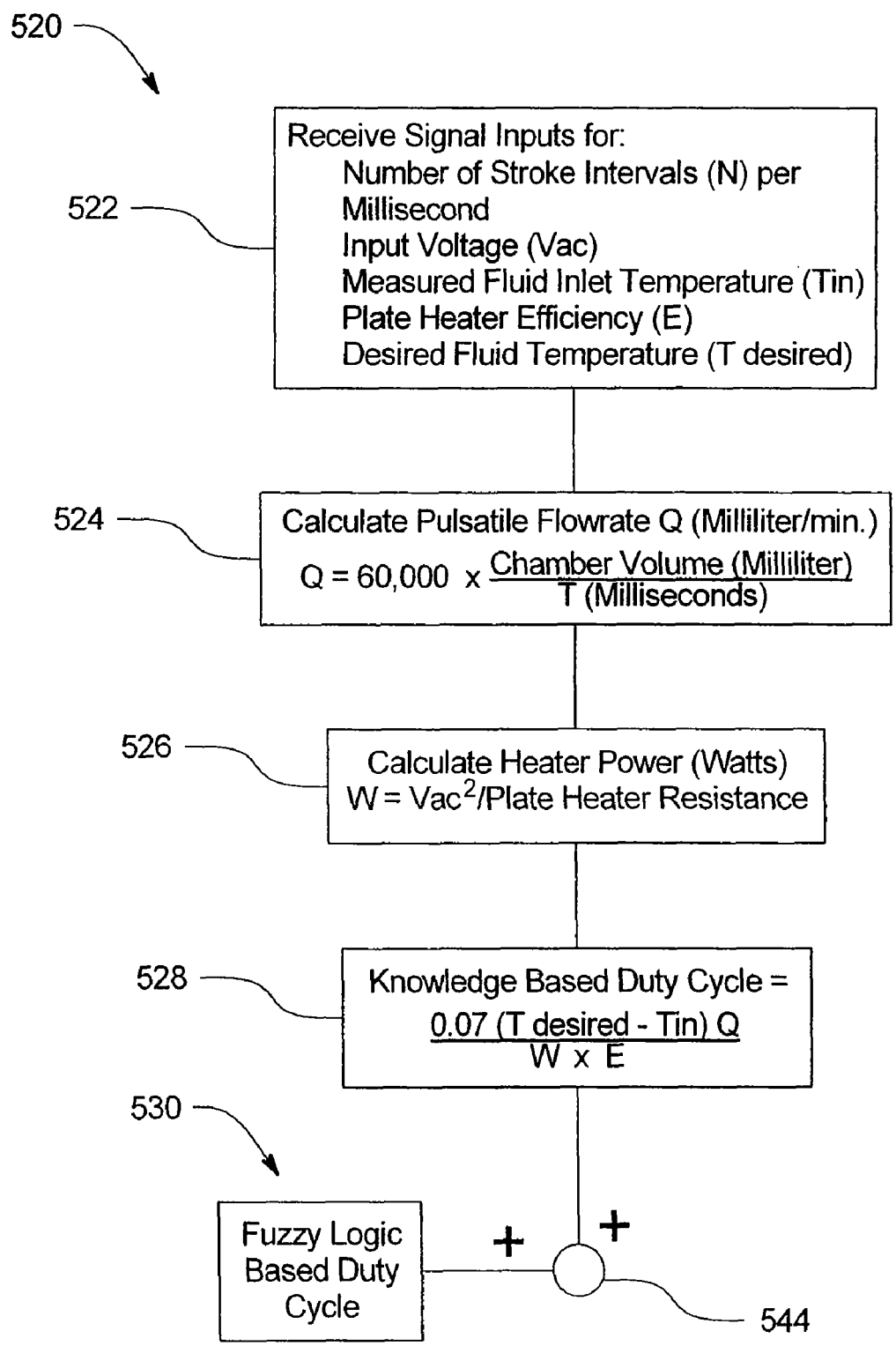
FIG. 26 is a flow diagram of a knowledge based algorithm of the method discussed in connection with FIG. 25.

Referring now to FIG. 26, the knowledge-based control algorithm 520 is illustrated in more detail. As discussed above, in a first step, the knowledge-based control algorithm receives a number of signal inputs, as indicated by block 522. Some of these inputs are updated at the main processor level of about once every two seconds. Other inputs are set in software as constants. One of the input signals that varies over time, is the number of stroke intervals ("N") per millisecond. The pump piston moves over a certain period of time, stops and dwells, and then moves again for a certain period of time. The pump makes N number of strokes per millisecond, which is inputted into the knowledge-based control algorithm.

Another input signal that varies over time is the input voltage ("Vac"). The input voltage Vac changes over time in a single house or in different locations. Another input signal that changes over time is the measured fluid inlet temperature ("Tin"). Fluid temperature Tin is measured by one of the numerous sensors of the method 510 described above. An input which will like not change over time is the plate heater efficiency ("E"). The heater efficiency E is determined empirically. The heater efficiency E could change depending upon the pressure inside the disposable unit during heating, the material of the disposable unit and the gap tolerance between the top and bottom plate. The heater efficiency E for a particular dialysis device therefore remains substantially constant. As described above, the desired fluid temperature ("Tdesired") may vary, depending on doctor's orders. However, for any given therapy session, Tdesired is a constant.

The knowledge-based control algorithm 520 calculates a pulsatile flowrate ("Q") in millimeters per minute according to the formula of block 524. The formula for Q can change based on the desired units for the flowrate. In the illustrated embodiment, the formula for Q is 60,000 multiplied by the chamber volume in milliliters, the product of which is divided by T in milliseconds. Once again, the chamber volume is a constant that is a function of pump chamber wall geometry.

The knowledge-based control algorithm 520 also calculates the total heater power in Watts, as indicated by block 526. In the illustrated embodiment, the method 510 calculates the heater power by dividing $V_{ac}^2$ by a plate heater resistance. The knowledge-based control algorithm 520 then uses the above calculations to calculate the knowledge-based duty cycle, as indicated by block 528. The knowledge-based duty cycle equals, in one embodiment, a factor, e.g., of 0.07, multiplied by the temperature differences ΔT, which equals $T_{desired}$ minus the $T_{in}$. This product is then multiplied by the pulsatile flowrate Q. The latter product is then divided by the product of the total heater power W times the heater efficiency E. The knowledge-based duty cycle is then fed into summation point 544 in combination with the fuzzy logic-based duty cycle output as illustrated by FIG. 26.

Figure 27:
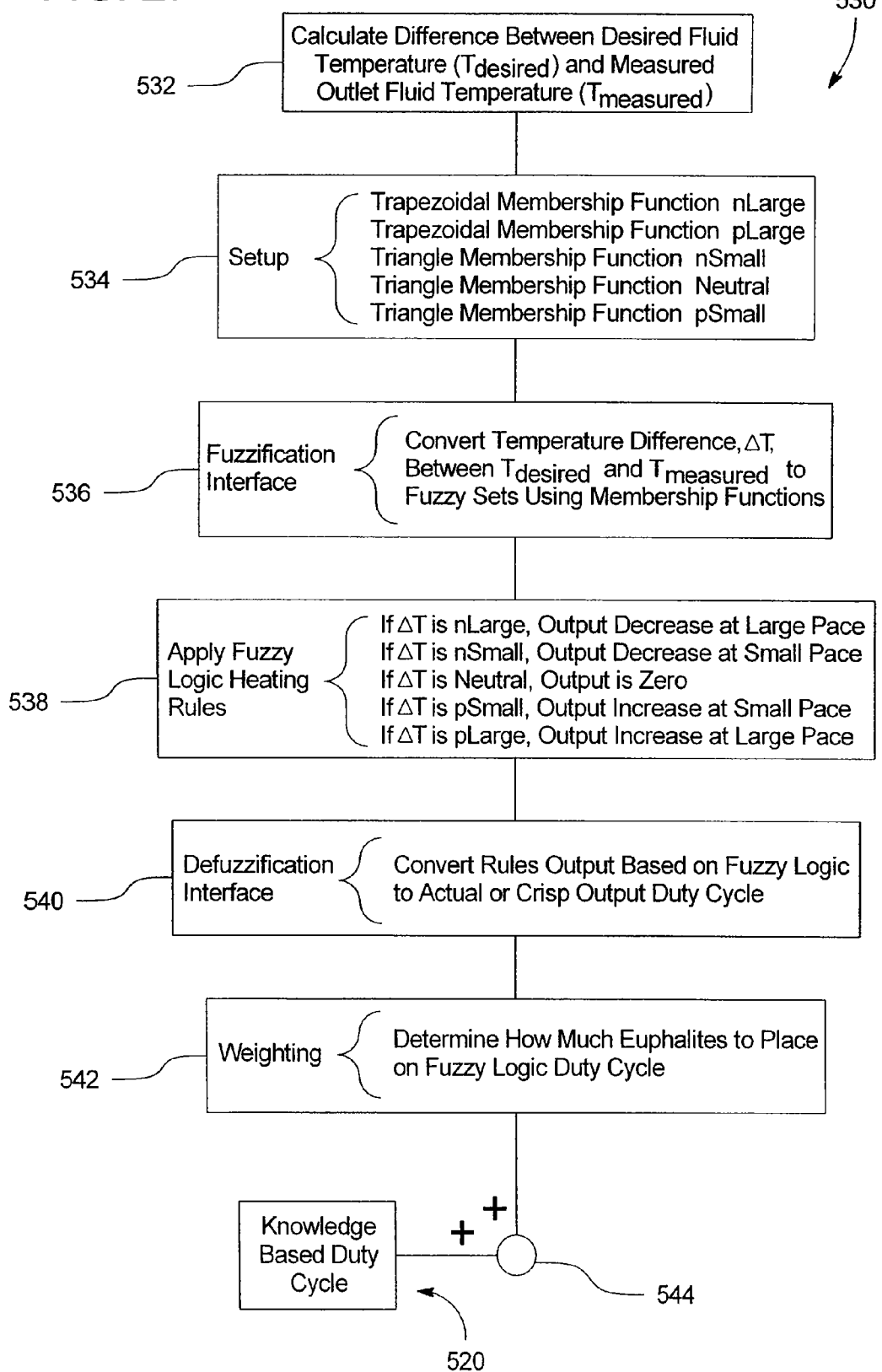
FIG. 27 is a flow diagram of a fuzzy logic based algorithm of the method discussed in connection with FIG. 25.

Referring now to FIG. 27, one embodiment for the fuzzy logic control algorithm 530 is illustrated. It should be appreciated that fuzzy logic is known generally to systems engineers and in the field of system and process control. The fuzzy logic algorithm described herein is merely one method of implementing fuzzy logic to perform the task of accepting an error input, which is the difference between the desired fluid temperature and the actual fluid temperature, and attempting to minimize this number to zero. Regardless of the method in which fuzzy logic is employed, the method inputs a temperature, sums a ΔT, and outputs a power limiter, such as the duty cycle. The first step in the fuzzy logic control logic algorithm 530 is to therefore calculate the difference between $T_{desired}$ and $T_{in}$, as indicated by block 532.

Next, a number of membership functions are implemented, as indicated by block 534. In this embodiment, the algorithm 530 implements five measurement functions. Two of the measurement functions, namely, nlarge and plarge, are trapezoidal membership functions. As is known in the art of fuzzy logic, the trapezoidal membership function consists of four nodes. Three other membership functions, namely nsmall, neutral and psmall, are set up as triangle membership functions, which consists of three nodes. After setting up the membership functions as indicated by block 534, the fuzzy logic control algorithm 530 performs a fuzzification interface as indicated by block 536. In the fuzzification interface, the control algorithm 530 converts the temperature difference, ΔT, between $T_{desired}$ and $T_{in}$ to a number of fuzzy sets based on the membership functions set up as indicated in block 534.

Next, the control algorithm 530 applies a number of fuzzy logic heating rules as indicated by block 538. In an embodiment, the control algorithm 530 employs five fuzzy logic rules. One rules says that, if ΔT is nlarge, the output should decrease at a large pace. Another rules says that, if ΔT is nsmall, the output should decrease at a small pace. The third rule states that if ΔT is neutral, the output should be zero. A further rules states that if ΔT is psmall, the output should increase at a small pace. The final rule states that if ΔT is plarge, the output should increase at a large pace.

The next step in the fuzzy logic control algorithm 530 is to perform a defuzzification interface, as indicated by block 540. In the defuzzification interface, the output of the rules is converted to an actual or "crisp" output, which can then be translated into a duty cycle. In the defuzzification step indicated by block 590, the output of the fuzzy logic rules is converted to a "crisp" or exact number. This number is then converted to the proper output for the heater which, in this embodiment, is the fuzzy heater duty cycle.

As indicated by block 542, the next step is to determine how much weight to place on the fuzzy logic duty cycle with respect to the knowledge-based duty cycle. The weighting factor is decided by the fuzzy logic rules and the update rates of both the knowledge based and fuzzy logic based control algorithms. The weighted fuzzy logic duty cycle is then summed in summation point 544 with the knowledge-based duty cycle yielded by the knowledge-based control algorithm 520.

IX. Electrical Insulation for the System

Medical equipment and in particular equipment in intimate contact with a patient needs to be properly electrically insulated against leakage currents. Class I type of equipment provides basic insulation and a means of connecting to a protective earthing conductor in the building in which the equipment resides, which dissipates hazardous voltages if the equipment insulation fails. One primary use for the system 10, 100 of the present disclosure however is in a patient's home. This presents two problems for Class I devices and in particular for dialysis machines. First, in many countries and older homes, the earthing ground is faulty, unreliable or completely absent. Second, many people bypass grounding systems that do exist. The present disclosure overcomes this problem by providing an automated dialysis system 10, 100 that requires no earth ground. The system 10, 100 does not simply rely on the basic insulation provided by Class I devices but provides either double insulation or reinforced insulation.

Double insulation includes two layers of insulation. One layer of insulation can be the basic insulation. At 240 VAC, basic insulation typically requires four millimeters of "creepage" or 2.5 millimeters of "air clearance". Creepage is the shortest distance between two conductive parts when both are disposed along a surface of insulation. Creepage is also the shortest distance between a conductive part and a bounding surface of a piece of equipment, wherein the conductive part and the equipment contact a piece of insulation. Air clearance is the shortest distance between two conductive parts or between a conductive part and a piece of equipment, measured through air.

The additional layer of insulation is called supplemental insulation. Supplemental insulation is independent insulation applied in addition to the basic insulation to ensure protection against electric shock if the basic insulation fails. The supplemental insulation can also be in the form of creepage and clearance.

Reinforced insulation, on the other hand, is a single layer of insulation offering the same degree of protection as double insulation. Reinforced insulation provides the electrical protection equivalent to double insulation for the rated voltage of the double insulation. For 240 VAC, used as the mains voltage of the system 10, 100, the basic insulation can withstand 1500 VAC and the supplemental insulation can withstand 2500 VAC. The single layer of reinforced insulation must therefore withstand at least 4000 VAC.

Figure 28:
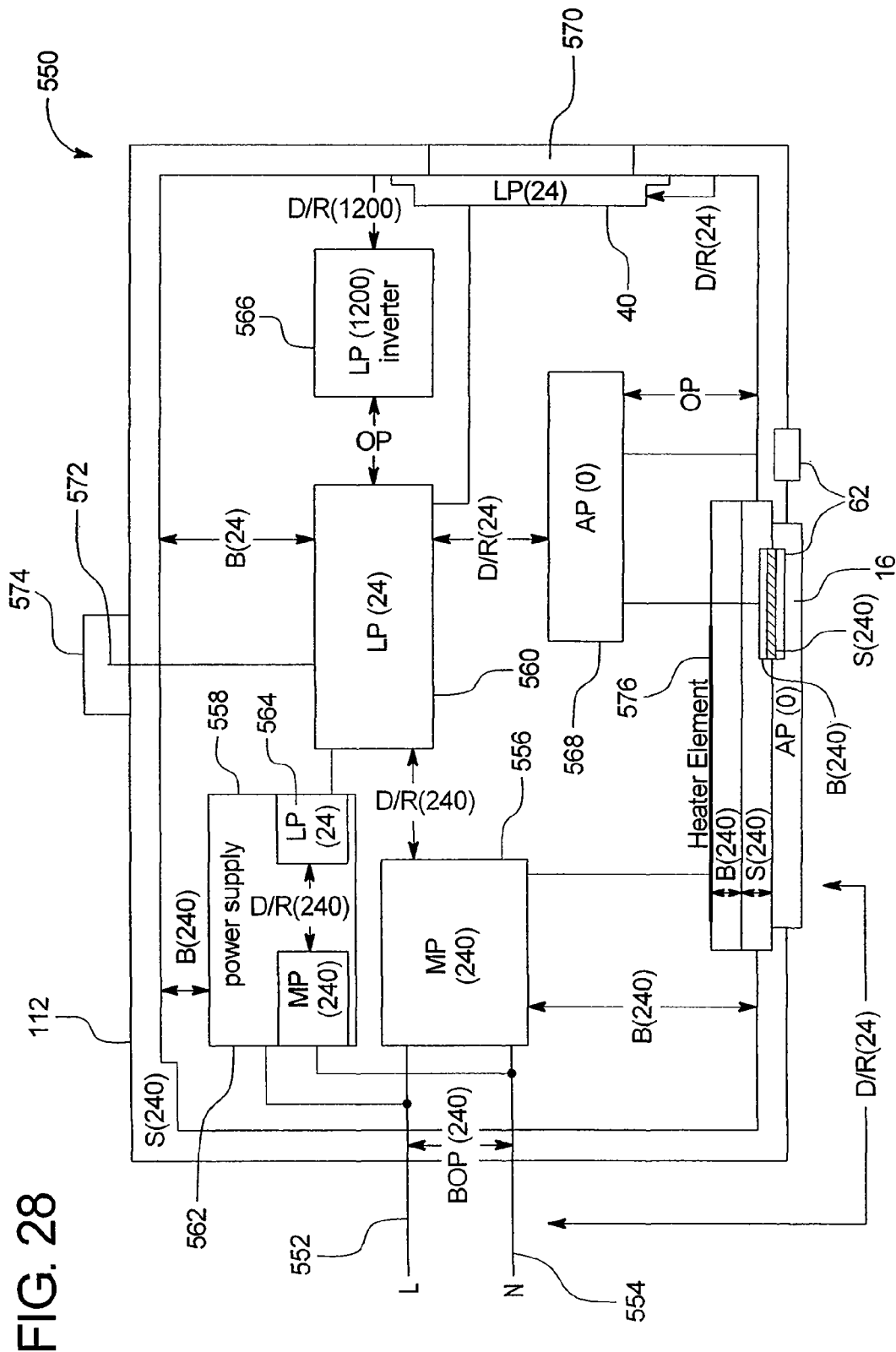
FIG. 28 is an electrical insulation diagram illustrating one embodiment for providing double electrical insulation in the medical fluid unit of the present disclosure.

Referring now to FIG. 28, one embodiment of an electrically insulated system 550 of the present disclosure is illustrated. The system 550 is illustrated schematically, however, certain components of the system 550 are identifiable as components illustrated in the hardware drawings discussed above. For example, the system 550 includes the housing or enclosure 112, illustrated above in FIGS. 3A to 4B, which includes the base 114 and the lid 116 of the hardware unit 110. The system 550 also includes the heater 16, which in an embodiment includes upper and lower heating plates illustrated in FIG. 3A and discussed in connection with FIGS. 25 to 27. Further, the system 550 includes the display device 40 and temperature sensors 62 illustrated and discussed in connection with FIGS. 1 and 2.

In FIG. 28, the numbers in parenthesis indicate the working or operating voltage of the respective component. As illustrated, the line 552 and neutral 554 supply a mains voltage of 240 VAC, single phase, in an embodiment, which is the standard voltage used residentially in many countries throughout the world. The line 552 and neutral 554 could otherwise supply the United States residential standard of 120 VAC, single phase, and indeed could provide a voltage anywhere in the range of 90 to 260 VAC. The line 552 and neutral 554 feed the 240 VAC into a mains part 556. It is worth noting that the system 550 does not include or provide a protective earth conductor.

The mains part 556 feeds 240 VAC to a power supply printed circuit board ("PCB") 558. Power supply PCB 558 includes a mains part 562 and a live part 564. For purposes of the present disclosure, a "mains part" is the entirety of all parts of a piece of equipment intended to have a conductive connection with the supply mains voltage. A "live part" is any part that if a connection is made to the part, the part can cause a current exceeding the allowable leakage current for the part concerned to flow from that part to earth or from that part to an accessible part of the same equipment.

As illustrated, the live parts 560 and 564 step down in voltage from the mains parts 556 and 562, respectively, to 24 VDC. Obviously, the voltage may be stepped down to other desired levels. Live part 560 feeds live part 566. Live part 566 is an inverter having a step-up transformer that outputs a voltage of 1200 Vpeak. The inverter 566 powers a number of cathode fluorescent lights, which provide backlighting for the display device 40.

Live part 560 is also electrically isolated from applied part 568, which is maintained at a zero potential. An "applied part" for purposes of the present disclosure is any part of the system 550 that: (i) comes into physical contact with the patient or operator performing the dialysis treatment; (ii) can be brought into contact with the patient or operator; or (iii) needs to be touched by the patient. For instance, it is possible for the patient to touch the upper or lower plates of the plate heater 16, the temperature sensors 62 and the enclosure or housing 112. The applied part 568 represents schematically the casing or insulation around the temperature sensors 62.

In an embodiment, which only includes a display device 40 and not a touch screen 42 (discussed in FIGS. 1 and 2), the housing 112 includes a window 570, such as a glass or clear plastic window. The glass or plastic window provides the same level of insulation as the rest of the, e.g., plastic housing or enclosure 112. In an embodiment which does include a touch screen 42, the touch screen is properly electrically insulated, preferably by the manufacturer of same. Alternatively, one or more layers of insulation discussed below could be added to system 550 to properly insulate the touch screen 42.

The system 550 makes available an input/output port 572, which can be a serial port or an Ethernet port to connect the system 550 to an external computer, a local area network, a wide area network, an internet and the like. To electrically insulate input/output port 572, the system provides a protective covering or casing 574.

The mains part 556 powers the heater element 576, which is positioned and arranged to heat both the upper and lower plates of the plate heater 16. In an alternative embodiment (not illustrated), the mains part 556 powers the infrared heater discussed above. As illustrated, double insulation is maintained between the heater element 576 and the heater plate 16. The double insulation includes basic insulation B(240), rated for 240 VAC, and supplemental insulation S(240), rated for 240 VAC.

For the heater plate 16 and element 576, at least, the basic and supplemental insulation needs to be electrically insulative but thermally conductive. Polyimides, such as a Kapton®, work very well. In an embodiment, therefore, the B(240) and S(240) layers each include Kapton® tape or sheet of about 0.3 millimeters thickness. As further illustrated, another layer of basic insulation B(240), rated for 240 VAC, and another layer of supplemental insulation S(240), rated for 240 VAC, are disposed between the temperature sensor 62 and the heater plate 16. Thus the heater plate 16 is completely and doubly insulated from the remainder of the system 550. Alternatively, either of the double layers of insulation can be replaced by a single layer of reinforced insulation.

The line 552 and the neutral 554 are insulated by basic operation insulation BOP (240), rated for 240 VAC, which is the electrical insulation wrapped or extruded around the respective wires. Basic insulation B(240), rated for 240 VAC, is provided between the mains part 556 and the enclosure 112 and between the power supply PCB 558 and the enclosure. The basic insulation B(240) can be in the form of a properly separated air gap. The enclosure 112 itself provides supplemental insulation S(240) for 240 VAC. The mains part 556 is therefore doubly insulated from the outside of the enclosure 112.

Since applied part 568 is maintained at a zero operating voltage, there needs to be no additional insulation placed between the applied part 568 and the housing 112. Accordingly, there is simply an operational separation displayed figuratively as OP between the applied part 568 and the housing 112. Double insulation or reinforced insulation D/R (24) for 24 VDC is however provided between live part 560 and the applied part 568, so that applied part 568 maintains its zero potential. Basic insulation B(24), rated for 24 VDC, is provided between live part 560 and the enclosure 112. The basic insulation B(24) can be in the form of a properly separated air gap. As stated above, the enclosure 112 itself provides supplemental insulation S(240) for 240 VAC. Live part 560 is therefore doubly insulated from the outside of the enclosure 112.

No additional insulation is needed and only an operational separation OP is provided between live part 560 and the live part 566. Since live part 566 is stepped up to 1200 Vpeak, the supplemental insulation S(240) rated for only 240 VAC of the enclosure 112 should not be relied upon. Accordingly, double insulation or reinforced insulation D/R (1200) for 1200 Vpeak is provided between the live part 566 and the housing 112.

Double insulation or reinforced insulation D/R (240) for 240 VAC is provided between the mains part 556 and the live part 560. Double insulation or reinforced insulation D/R (240) for 240 VAC is also provided between the line and neutral line 554 and the upper and lower plates of plate heater 16. Still further, double insulation or reinforced insulation D/R (240) for 240 VAC is provided between the mains part 562 and the live part 564 of the power supply PCB 558. Here, in the case of double insulation, either the basic or supplementary insulation can be a properly separated creepage distance on the PCB 558.

Double insulation or reinforced insulation D/R (24) for 24 VDC is provided between the housing 112 and the display device 40. The separation between the display device 40, maintained at 24 VDC and the inverter, maintained at 1200 Vpeak is only required to be operational. Live part 566 must be separated from the outside of the housing 112 by D/R (1200) but not from the LP(24). The reason is that the LP(1200) is on the secondary side of the live part 566 and if it is shorted to the LP(24) due to a failure of the operational insulation, LP(1200) will become at most 24 VDC, providing no safety hazard.

X. Graphical User Interface

Figure 29:
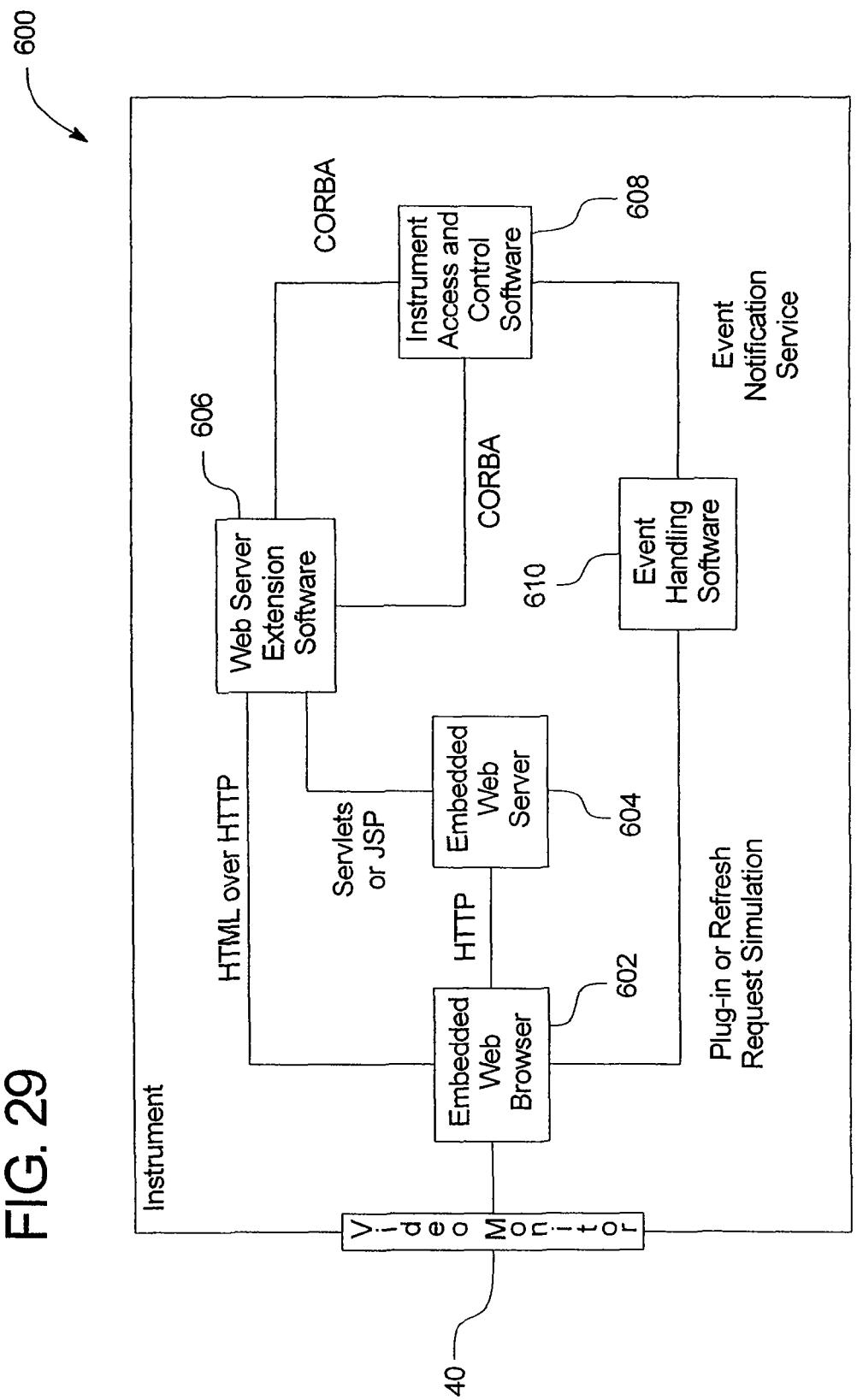
FIG. 29 is a schematic representation of one embodiment of the web based graphical user interface of the present disclosure.

Referring now to FIG. 29, one embodiment of a graphical user interface ("GUI") system 600 is illustrated. The GUI system 600 in an embodiment employs web-based software as well as other types of software. As discussed previously in connection with FIG. 28, the system 10, 100 of the present disclosure is provided with an input/output (e.g., serial or Ethernet) port 572, which is normally insulated from the patient by a cover 574. The port 572 allows the controller 30 of the system 10, 100 to access an internet and a variety of other networks. The GUI system 600 of the present disclosure takes advantage of this capability by enabling the controller 30 to interact with software on an internet or other network.

It should be appreciated that the GUI system 600 does not require the patient to have internet or network access in their home. Rather, the port 572 is for a maintenance person or installer to gain access to the controller 30 within the hardware unit 110. In this manner, the patient may bring their unit to a place having internet or network access, wherein the patient's software may be upgraded. The patient may then bring the unit home and operate it without having to gain internet or network access.

Using web-based software is advantageous because it is based on well established standards, so that the interface screens may be constructed using existing software components as opposed to being hand crafted. Web-based software allows for external communication and multiple access points. The software is portable. For each of these reasons, software constructed using existing software components reduces development time and cost.

The present disclosure includes the construction of a GUI using an embedded web browser 602. In an embodiment, the embedded web browser 602 is third party software. The embedded web browser 602 can include any third party browser that runs on a target platform and includes support for advanced features such as HTML 4.0, ECMAScript, and animated GIFs. The web browser 602 renders and supplies the various GUI screens to the video monitor 40. The web browser 602 also handles inputs made by the patient. When the operator interacts with the system (e.g., presses buttons 43, 124, 125 and 127 or turns knob 122, illustrated in FIG. 3B), the web browser 602 forwards information about the interaction to the embedded web server 604.

The web server 604 in turn uses a web server extension software 606 to process the interaction. The embedded web server 604 can also be any third party web server that runs on a target platform and includes support for the web server extension software 606 and that allows a dynamic definition of the information to be sent to the embedded web browser 602.

The web server extensions are developed internally using the web server extension software 606 and conform to the specification of a mechanism, such as a Servlet, which works in conjunction with the chosen embedded web server 604. The web server extension software 606 enables the web server 604 to retrieve back end and real time information from the instrument access and control software 608. There are a number of different existing web server extension technologies that may be used for the embedded web browser 602, the embedded web server 604 and the web server extension software 606, such as CGI, ASP, Servlets or Java Server Pages ("JSP").

The web server extension software 606 interacts with the instrument access and control software 608. The instrument access and control software 608 is an internally developed operating environment for controlling the various lower level components of the system 10, 100, such as the valve motor/actuator, pump motor/actuator and heater.

Depending on the operator input and the state of the automated dialysis system 10, 100, the web server extension software 606 can interact with the instrument access and control software 608 to obtain information from same and to cause one of the devices of the system 10, 100 to take action. The web server extension software 606 then sends information to the embedded web browser 602, which may then be displayed on the display device 40. The web server extension software 606 communicates with the instrument access and control software 608 using, in an embodiment, the CORBA standard. This communication, however, may take place using various different protocols known to those of skill in the art.

During the operation of the system 10, 100, an event may occur that requires high priority information to be displayed to the operator, for example, an alarm and corresponding message either on the display device 40 or on a separate dedicated alarm display. When a high priority event occurs, the instrument access and control software 608 generates an event that is handled by an event-handling software 610, which can be developed internally. The event-handing software 610 in turn notifies the embedded web browser 602, through the use of a plug-in or a refresh request simulation from the web server 604, to refresh whatever display the web browser is currently causing to be displayed on display device 40.

The event-handing software 610 enables information to flow from the instrument access and control software 608 to the embedded web browser 602 without a request by the embedded web browser 602, wherein the web browser thereafter requests a refresh. The web server 604 then forwards the request to the web server extension software 606. The web server extension software 606 determines what information should be displayed on the display device 40 based on the state of the system 10, 110. The web server extension software 606 then relays that information back to the embedded web browser 602, which updates the display device, e.g., to show an alarm condition.

In one embodiment of the GUI system 600, the web client is internal to the hardware unit 110 of the system 10, 100. As described above in connection with FIG. 1, the controller 10 includes a plurality of processors (referred to collectively herein as processor 34). A main microprocessor is provided that resides over a number of delegate processors. Each of the embedded web browser 602, web server 604, web server extension software 606 and event handling software 610 run on the main microprocessor. The instrument access and control software 608 runs on the main microprocessor and one or more of the delegate processors.

It is alternatively possible that a number of different external web clients may need to access information contained within the system 10, 100. It is therefore preferred that the HTTP commands to the embedded web server 604 not require predetermined passwords, but instead use a stronger and more flexible security system.

Referring now to FIGS. 30A-30M, a number of screen shots of the GUI 600 are illustrated that show the overall look and feel of the system 10, 100 as seen by the operator or patient. Further, these drawings illustrate various features provided by the GUI system 600. The goal of the automated dialysis system of the present disclosure is to make a simple and well operating system. The device only requires two supply bags 14, weighs less than 10 kg and can be powered virtually anywhere in the world without the risk of electrical shock to the patient. Similarly, the GUI system 600 is designed to be simple, intuitive, effective, repeatable and reliable.

As illustrated in FIG. 3B, the system 10, 100 includes a display device 40, a knob 122 that enables the user to interact with the GUI system 600 and a number of dedicated pushbuttons 43 that enable the patient to navigate between three different screens namely a parameter change screen, a log screen and a therapy screen. In an embodiment, a display device 40 is provided, wherein the input devices 43, 122, 124, 125 and 127 are each electromechanical. In an alternative embodiment, one or more of the input devices are provided by a touch screen 42 that operates with the display device 40 and a video controller 38.

A simulated or electromechanical "stop" input 124, an "OK" button 125 and a "back" button 127 are also provided. The OK button 125 enables the operator to indicate that a particular part of the set-up procedure has been completed and to prompt the GUI 600 to move on to a next step of the set-up stage or to the therapy stage. The stop button 124 enables the operator or patient to stop the set-up or therapy procedures. The system 600 may include a handshake type of response, such as "are you sure you want to stop the set-up". Other parts of the entire procedure, such as the patient fill or drain cycles immediately stop without further input from the operator. At certain points in the procedure, the system enables the operator to move back one or more screens using the back button 127.

Figure 30A:
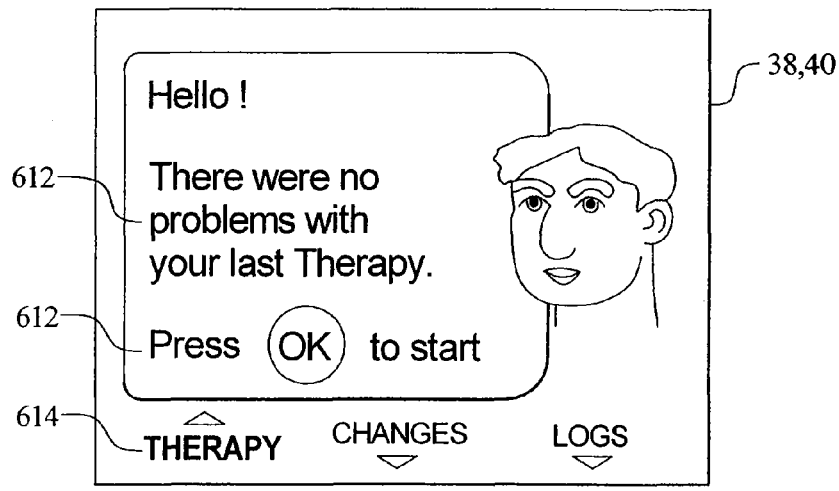
FIGS. 30A to 30M are screen shots from a display device employing the graphical user interface of the present disclosure.

Referring now to FIG. 30A, the display device 40 and the video controller 38 are adaptable to display animations, which provide the patient with information and instructions 612 in a comfortable format. As illustrated throughout the screen shots, the GUI system 600 waits for the patient to read and understand whatever is being displayed on the display device 40 before moving on to the next step or stage. FIG. 30A illustrates that the GUI system 600 is waiting until the patient is ready before beginning the therapy. The system 600 prompts the user to press an "OK" input to begin the therapy. FIG. 30A also illustrates that the therapy screen is being presently displayed by highlighting the word "therapy" at 614.

Figure 30B:
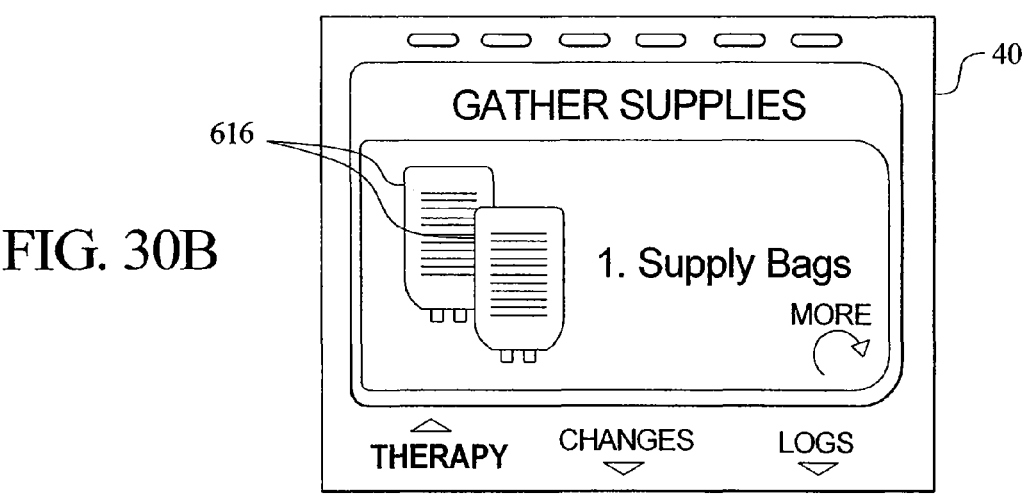
Figure 30C:
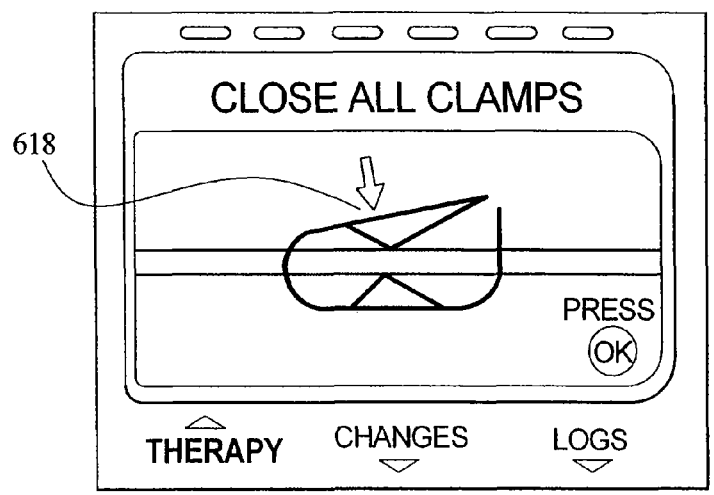

In FIG. 30B, the display device 40 of the GUI system 600 prompts the patient to gather the necessary supplies for the therapy, such as the supply bags 14. FIGS. 30B and 30C illustrate that the system 600 uses static images, such as static image 616 and animations, such as animation 618, which resemble the actual corresponding supplies or parts to aid the patient in easily, effectively and safely connecting to the system 10, 100. For example, the animation 618 of FIG. 30C looks like the actual hose clamp of the system 10, 100, which aids the patient in finding the proper piece of equipment to proceed with the therapy. The arrow of the animation 618 also illustrates the action that the patient is supposed to perform, reducing the risk that the patient will improperly maneuver the clamp or perhaps break the clamp.

Figure 30D:
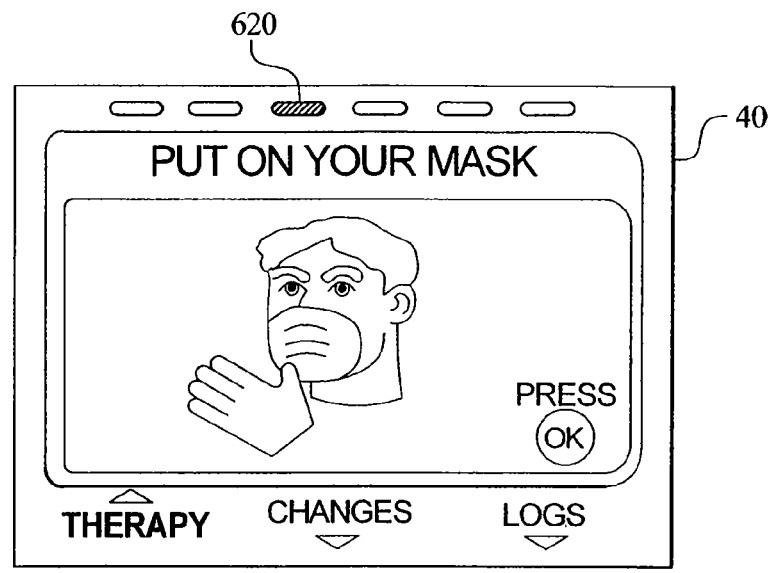
Figure 30E:
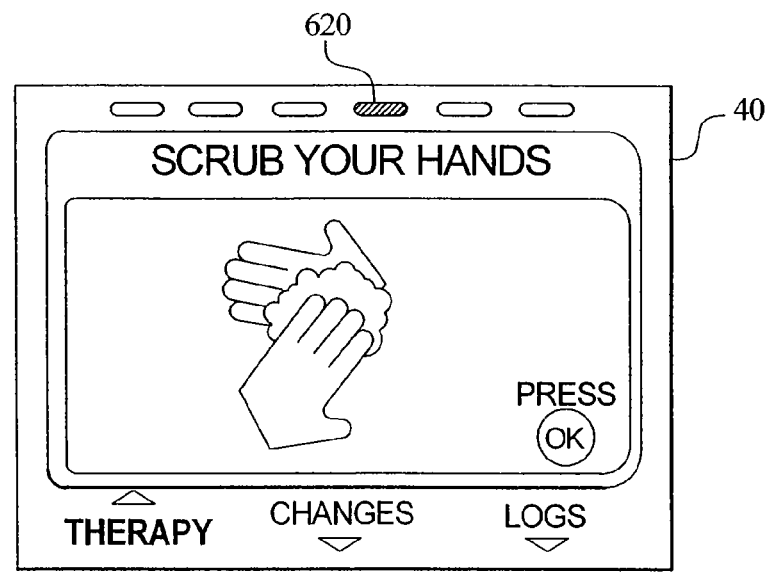

FIGS. 30D and 30E illustrate that the GUI system 600 promotes hygienic operation of the system 10, 100 by prompting the patient to: (i) take the steps of covering the patient's mouth and nose at the proper time; and (ii) wash the patient's hands before coming into contact with critical fluid connectors, such as the patient fluid connector and the supply bag connectors. The GUI system 600 waits for the patient to finish and press an OK input at each step before proceeding to the next step. As illustrated in FIGS. 30D and 30E, software LEDs 620 located at the top of the display device 40 indicate where the user is in the set-up procedure.

Figure 30F:
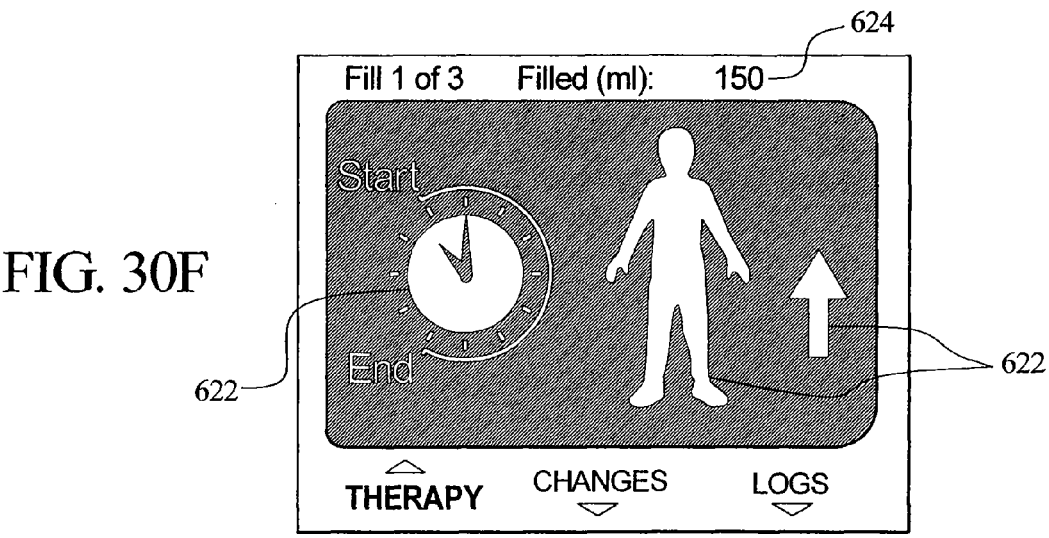
Figure 30G:
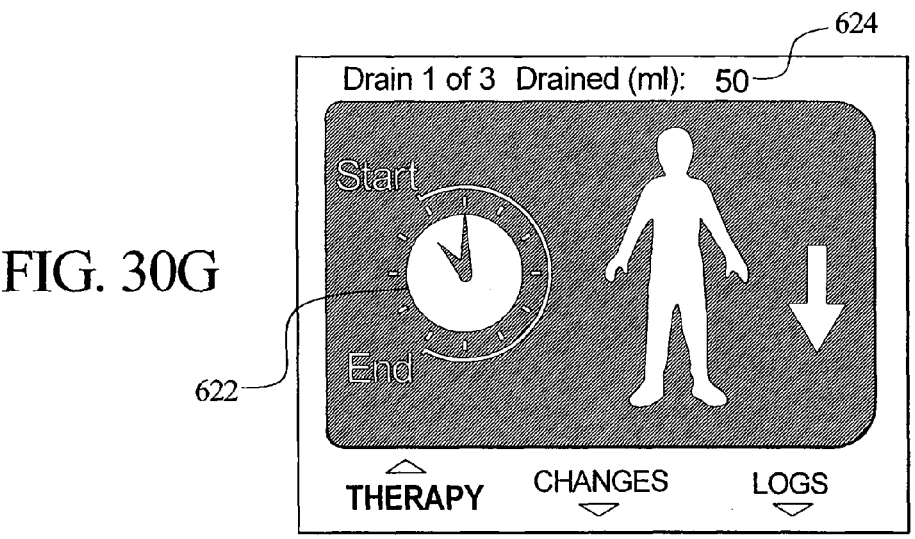

Screen shots of FIGS. 30A to 30E and 30H to 30M each present procedural set-up steps of the therapy. Accordingly, the colors of the screen shots of FIGS. 30A to 30E and 30H to 30M are chosen so that they are more visible when viewed during the day or with lights on. In one embodiment, the screens are different shades of blue, wherein the static images and animations and inner lettering are white and the outer lettering and borders are black. As illustrated by FIGS. 30F and 30G however, the screen shots that illustrate the active stages of the therapy are chosen so that they are more visible when viewed at night or with lights off. In one embodiment, the screen shots of FIGS. 30A to 30F are black with ruby red lettering, diagrams and illustrations, etc. The red letting is configured so as not to be intrusive to a sleeping patient but still visible at distances of about 10 to 25 feet (3 to 7.6 meters).

FIGS. 30F and 30G illustrate that during active stages of the therapy, the therapy status information is displayed on the screen shots in the form of both graphics 622 and numerical data 624. Therapy status information is displayed in real time or in substantially real time with a slight time delay. FIG. 30F illustrates a screen shot during a fill portion of the therapy. In particular, FIG. 30F illustrates the first fill of three total fills. The graphical clock 622 illustrates that the fill cycle time is approximately ⅛th elapsed. The arrow graphic 622 indicates that the therapy is in a fill cycle. Also the graphical representation of the body 622 has a very low percentage of dialysate. The numerical data 624 illustrates that the system 10, 100 has pumped 150 ml of dialysate into the patient.

FIG. 3G illustrates that the patient is currently undergoing the first drain cycle of three drain cycles that will take place overnight. The graphical representation of the clock illustrates that the drain cycle time is approximately ⅛th elapsed. The graphical arrow is pointing downward indicating a drain cycle. The body is shown as being substantially full of dialysate. The numerical data 624 illustrates that 50 ml of dialysate has been removed from the patient.

Figure 30H:
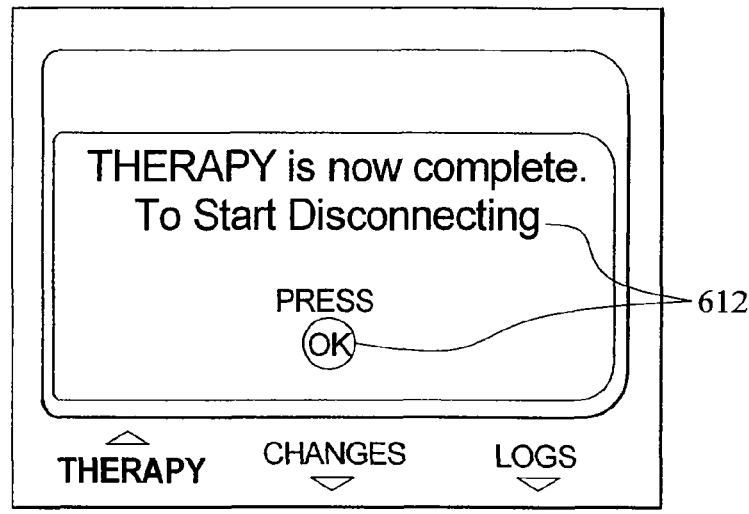
Figure 30I:
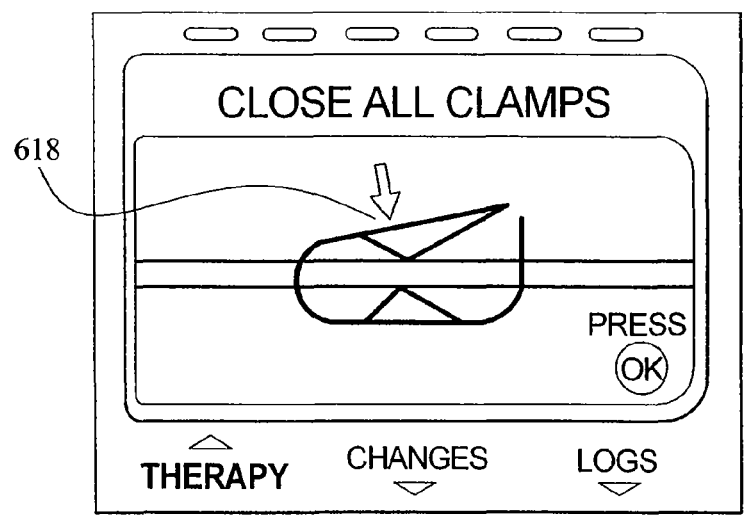

FIGS. 30H and 30I illustrate that in the morning when the therapy is complete, the screen reverts back to the daytime colors, or colors which are more easily seen in a lighted room. FIG. 30H includes information and instructions 612 that prompt the patient to disconnect from the system 10, 100. The system waits for the patient to select the OK button 125 (FIG. 3B) before proceeding. FIG. 30I includes an animation 618, which illustrates an action and equipment that the patient while disconnecting from the system. For each action in the disconnection sequence, system 600 waits for the patient to select the OK button 125 (FIG. 3B) before proceeding.

Figure 30J:
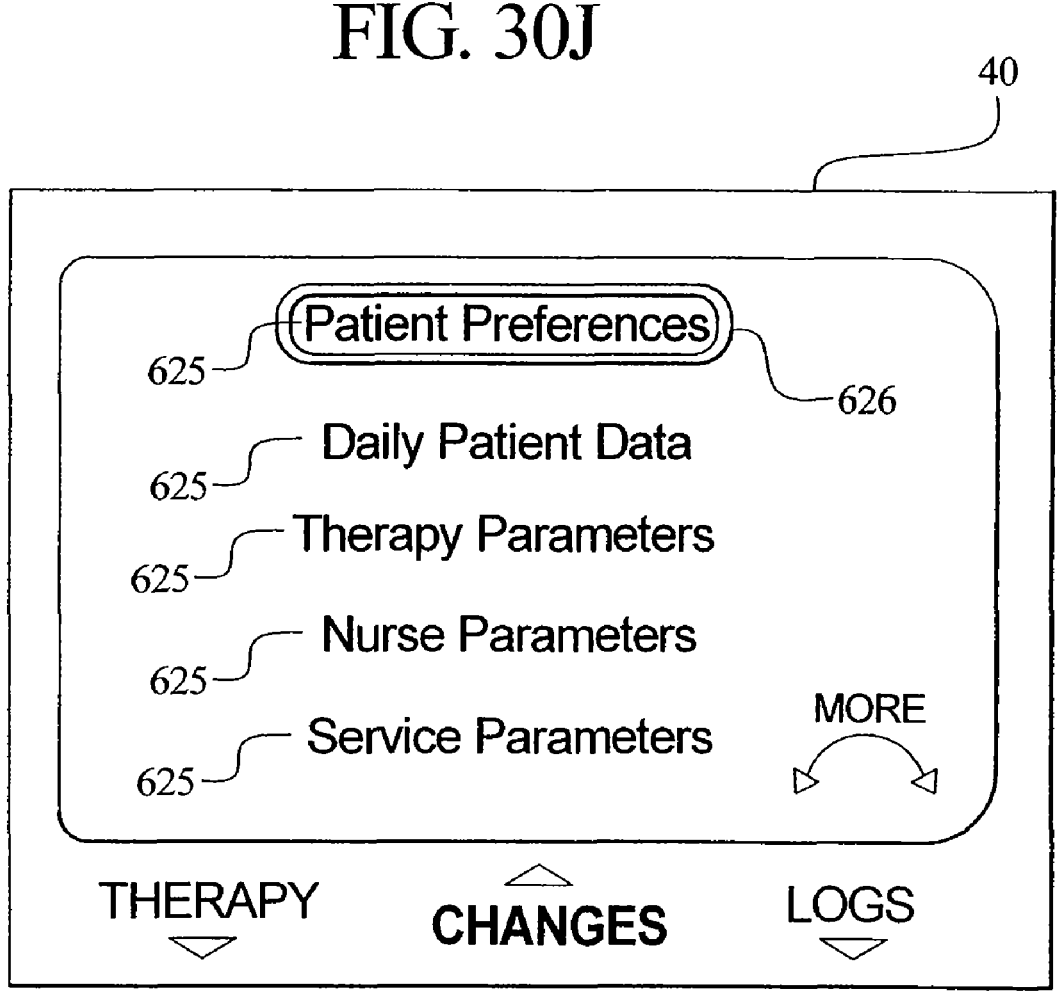

FIGS. 30J to 30M illustrate that in an embodiment, the user navigates between the therapy, parameter changes and log information by selecting one of the dedicated inputs 43 illustrated in FIG. 3B. FIG. 30J illustrates that the patient has selected the input 43 associated with the parameter changes information. The screen 40 in FIG. 30J now highlights the word "changes" instead of the word "therapy."

The parameter screen presents parameter information to the patient in a hierarchy format. First, as in FIG. 30J, the system 600 presents categories 625 of parameters, such as patient preferences, daily patient data, therapy parameters, nurse parameters and service parameters. The patient can scroll through the various categories 625 using the adjustment knob 122 of FIG. 3B, so that a desired category 625 is displayed in a highlighted display area 626. FIG. 30H illustrates that the patient preferences category 625 is currently displayed in the highlighted display area 626.

Figure 30K:
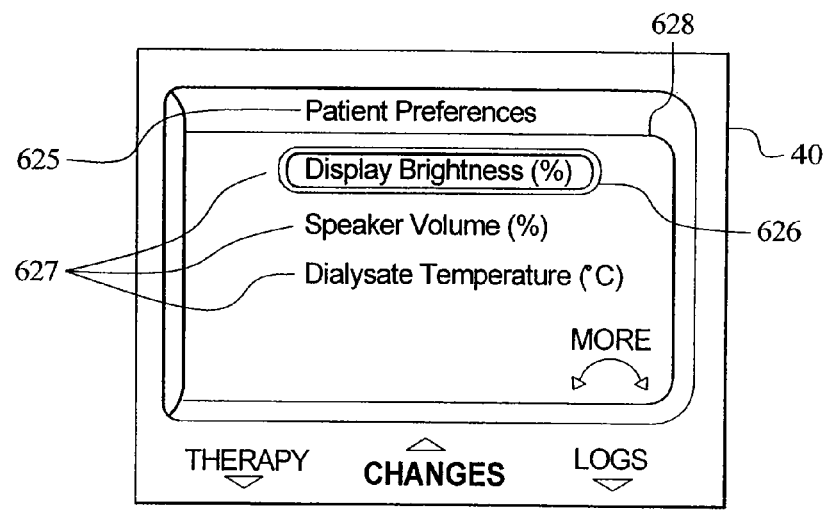

Once the user selects a highlighted category 625 by pressing the OK button 125 (FIG. 3B), a first door 628 slides open and presents the user with a list of the parameters 627 for the selected category 625 (e.g., the patient preferences category), as illustrated by the screen 40 of FIG. 30K. FIG. 30K illustrates that the patient preferences category 625 is displayed above the door 628, so that the patient knows which category 625 of parameters 627 is being displayed. At the same time, the highlighted display area 626 now displays one of a select group of the parameters 627 belonging to the patient preferences category 625.

The parameters 627 illustrated in FIG. 30K as belonging to the patient preferences category 625 include a display brightness percent, a speaker volume percent and a dialysate temperature in degree Celsius. Obviously, the patient preferences category 625 may include other parameters 627. The other categories 625 illustrated in FIG. 30J include different parameters 627 than those illustrated in FIG. 30K.

The patient can scroll through and select one of the parameters 627 for the patient preferences category 625 by rotating knob 122. In this manner, it should be appreciated that the signal knob 122 is used over and over again. This feature is in accordance with the goal of providing a simple system, wherein the patient only has to turn one knob instead of remembering which knob from a plurality of knobs applies to a particular feature. The knob 122 also enables the lettering to be bigger because the patient can scroll through to see additional parameter selections that are not displayed when the door 628 is initially displayed. That is, the functionality of the knob 122 provides freedom to the GUI 600 to not have to display all the possible parameters at once. It should be appreciated that this benefit also applies to the category selection screen of FIG. 30J, wherein each of the categories 625 does not have to be displayed simultaneously.

Figure 30L:
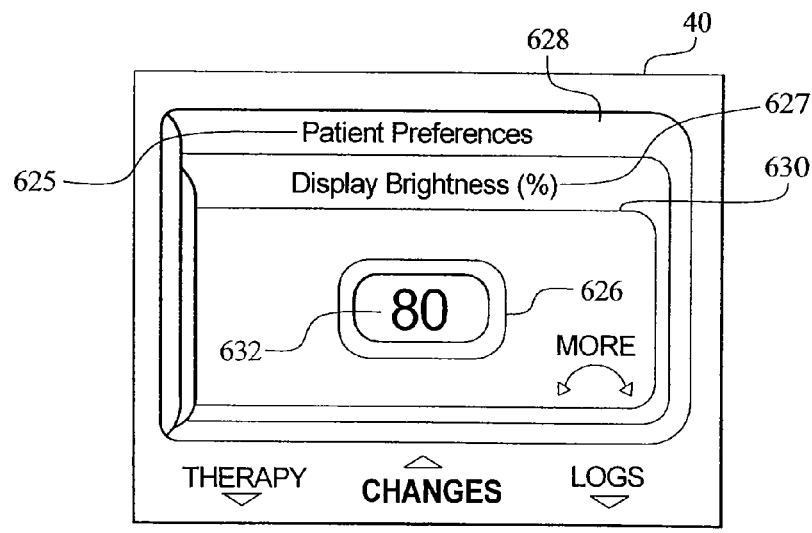

Once the patient selects one of the parameters of the patient preferences category, e.g., by pressing the OK button 125, a second door 630 slides open, wherein the display device 40 illustrates that the patient has selected the display brightness parameter 627 of the patient preferences category 625, which is still displayed by the first door 628 in FIG. 30L. The highlighted area 626 now displays one of the range of possible values 632 for the selected parameter 627 of the selected category.

Figure 30M:
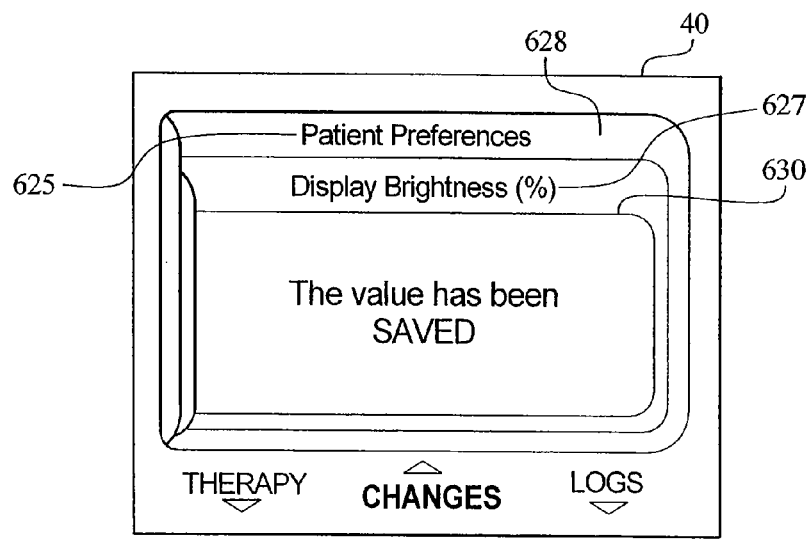

In FIG. 30L display device 40 illustrates that the highlighted display area 626 currently shows a value 632 of eighty for the display brightness parameter 627 of the patient preferences category. Once again, the patient changes the value 632 of the selected parameter 627 by rotating the knob 122. When the patient selects a value 632 (by pressing the OK input 125 illustrated in FIG. 3B while the desired value is displayed) for the parameter of the chosen category, the GUI system 600 saves the value as indicated by the display device 40 in FIG. 30M. FIG. 30M illustrates that the system 600 provides a feedback message to the patient that the selected value has been saved.

The system 600 in an embodiment presents information and instructions to the operator through the various visual tools discussed above. In an alternative embodiment, in addition to the visual information and instructions 612, static images 616, animations 618, parameter information, etc., one, or more or all of the above disclosed methods of communication is presented audibly to the patient or operator through speakers 129 (FIG. 3B) and a sound card (not illustrated) that cooperate with the controller 30 of the system 10, 100.

The various programs that run on the main microprocessor can also include one or more programs that activate a certain sound file at a certain time during the therapy or upon a certain event initiated by the system 600, e.g., an alarm, or upon a patient or operator input. The sound files can contain the sound of a human voice or any other type of sound. The sound files walk the patient through the set-up portion of the therapy in an embodiment. The sound files can alert a patient who has made an inappropriate input into the GUI 600, etc. The system does not activate a sound during the cycles, e.g., while the patient sleeps, in an embodiment.

If the operator selects the dedicated input 43 corresponding to the log information (not illustrated), the GUI 600 displays a screen or screens that show therapy data. In an embodiment, the therapy data is presented in a number of operator selectable logs. One of the logs can be a default log that is displayed initially, wherein the operator can switch to another log via, e.g., the knob 122. The logs may pertain to the most recent therapy and/or can store data over a number of days and a number of therapies. The logs can store any type of operating parameter information such as cycle times, number of cycles, fluid volume delivered, fluid temperature information, fluid pressure information, concentration of dialysate constituents, any unusual or alarm type of events, etc.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of making a peritoneal dialysis therapy machine having a tubing set comprising:
   packaging an end of each of a plurality of tubes of the set in a body;
   arranging the tubes according to a sequence of steps of a dialysis treatment set-up procedure so that a user is urged to remove the tubes from the single body in a desired order; and
   configuring the body to plug connectors attached to each of the ends of the tubes.

2. The method of claim 1, which includes configuring the body to be held in place by an enclosure of the dialysis therapy machine.

3. The method of claim 1, which includes configuring the body and the dialysis therapy machine so that the body can slide into the machine from only a desired direction.

4. The method of claim 1, which includes configuring an enclosure of the dialysis therapy machine to hold the body sturdily to aid the user in removing the tubes from the body.

5. The method of claim 1, which includes configuring an enclosure of the dialysis therapy machine and the body so that the body is removable from the enclosure after the tubes have been removed the body.

6. The method of claim 1, wherein the end of each of the tubes is a first end, and which includes configuring a second end of each of the tubes to be attachable to a disposable pumping cassette.

7. The method of claim 6, which includes aiding a location of the cassette via at least one alignment apparatus located on the dialysis therapy machine.

8. The method of claim 1, which includes sequencing the tubes in order, drain tube, at least one supply tube and patient tube.

9. The method of claim 1, which includes aiding a patient line prime by placing a hydrophobic membrane in the body at a patient line plug.

10. The method of claim 1, which includes arranging the body and the machine so that the tubes are mounted vertically on the machine.

11. A method of making a peritoneal dialysis therapy machine having a tubing set comprising:
packaging an end of each of a plurality of tubes of the set in a body;
arranging the tubes according to a sequence of steps of a dialysis treatment set-up procedure so that a user is urged to remove the tubes from the body in a desired order; and
configuring the body and the machine so that the tubes are mounted in a vertical relationship to one another on the machine, such that a first tube of the sequence is located above a second tube of the sequence.

12. The method of claim 11, which includes configuring the body and the machine so that the drain tube is located vertically above at least one supply tube, the at least one supply tube located vertically above a patient tube.

13. The method of claim 11, which includes tapering the body so that it slides downwardly and removably into the machine.

14. The method of claim 11, which includes configuring the body to plug connectors attached to each of the ends of the tubes.

15. The method of claim 11, wherein the end of each of the tubes is a first end, and which includes configuring a second end of each of the tubes to be attachable to a disposable pumping cassette.

16. A method of making a peritoneal dialysis therapy machine comprising:
packaging an end of each of the dialysis tubes in a body;
arranging the tubes in the body according to a sequence of steps of a dialysis treatment set-up procedure so that a user is urged to remove the tubes from the body in a desired order; and
configuring an enclosure of the dialysis therapy machine such that the tubes are held via the body on the machine in vertical order according to the set-up procedure.

17. The method of claim 16, which includes tapering the body and a mating apparatus on the enclosure for ready insertion of the body.

18. The method of claim 16, which includes arranging the enclosure so that the drain tube is located vertically above at least one supply tube, which is located vertically above a patient tube.

19. The method of claim 16, wherein the end of each of the tubes is a first end, and which includes configuring a second end of each of the tubes to be attachable to a disposable pumping cassette.

20. The method of claim 19, wherein the set-up procedure includes loading the disposable pumping cassette into the machine.

* * * * *